(12) United States Patent
Beutler et al.

(10) Patent No.: US 11,098,054 B2
(45) Date of Patent: Aug. 24, 2021

(54) ENGLERIN DERIVATIVES FOR TREATMENT OF CANCER

(71) Applicants: The United States of America, as represented by the Secretary, Department of Health and Human Services, Bethesda, MD (US); Fundacio Institut Catala D'Investigacio Quimica, Tarragona (ES); University of Delaware, Newark, DE (US); University of Leeds, Leeds (GB); Universitat Rovira I Virgili, Tarragona (ES)

(72) Inventors: John A. Beutler, Union Bridge, MD (US); Antonio Echavarren, Tarragona (ES); William Chain, Newark, DE (US); David Beech, Leeds (GB); Zhenhua Wu, Newark, DE (US); Jean-Simon Suppo, Tarragona (ES); Fernando Bravo, Tarragona (ES); Hussein Rubaiy, Leeds (GB)

(73) Assignees: The United States of America, as represented by the Secretary, Department of Health and Human Sciences, Bethesda, MD (US); Fundacio Institut Catala D'Investigacio Quimica, Tarragona (ES); University of Delaware, Newark, DE (US); University of Leeds, Leeds (GB); Universitat Rovira I Virgili, Tarragona (ES)

(*) Notice: Subject to any disclaimer, the term of this patent is extended or adjusted under 35 U.S.C. 154(b) by 0 days.

(21) Appl. No.: 16/628,768

(22) PCT Filed: Jul. 5, 2018

(86) PCT No.: PCT/US2018/040910
§ 371 (c)(1),
(2) Date: Jan. 6, 2020

(87) PCT Pub. No.: WO2019/010298
PCT Pub. Date: Jan. 10, 2019

(65) Prior Publication Data
US 2020/0140451 A1  May 7, 2020

Related U.S. Application Data

(60) Provisional application No. 62/529,063, filed on Jul. 6, 2017.

(51) Int. Cl.
*C07D 493/08* (2006.01)
*A61P 35/00* (2006.01)
(Continued)

(52) U.S. Cl.
CPC ............ *C07D 493/08* (2013.01); *A61P 35/00* (2018.01); *C07D 471/08* (2013.01); *C07D 495/08* (2013.01)

(58) Field of Classification Search
None
See application file for complete search history.

(56) References Cited

U.S. PATENT DOCUMENTS

| 2014/0057950 A1* | 2/2014 | Christmann ............ A61P 35/00 514/337 |
| 2016/0347764 A1* | 12/2016 | Chain ..................... A61K 45/06 |
| 2018/0127433 A1* | 5/2018 | Beutler ..................... A61P 3/10 |

FOREIGN PATENT DOCUMENTS

| EP | 2474550 A1 | 7/2012 |
| WO | 2012/084267 A1 | 6/2012 |

(Continued)

OTHER PUBLICATIONS

Wu ("Englerins: A Comprehensive Review" J. Nat. Prod. 2017, 80, p. 771-781, including Supporting Information p. S1-S21) (Year: 2017).*

(Continued)

*Primary Examiner* — Amy C Bonaparte
(74) *Attorney, Agent, or Firm* — Leydig, Voit & Mayer, Ltd.

(57) ABSTRACT

Disclosed is a compound of formula (I) in which a, $R^1$-$R^5$ and $X^1$ are as described herein. Also disclosed are a pharmaceutical composition containing the compound and a method of using the compound for treating cancer, such as renal cancer.

21 Claims, 35 Drawing Sheets

(51) Int. Cl.
　　C07D 495/08　　(2006.01)
　　C07D 471/08　　(2006.01)

(56) References Cited

FOREIGN PATENT DOCUMENTS

| WO | 2013/106226 A2 | 7/2013 |
| WO | 2014/078350 A1 | 5/2014 |
| WO | 2016/168281 A1 | 10/2016 |

OTHER PUBLICATIONS

Fash ("Synthesis of a stable and orally bioavailable englerin analogue" Bioorganic and Medicinal Chemistry Letters, 26, 2016, p. 2641-2644) (Year: 2016).*
Akbulut et al., "(−)-Englerin A is a Potent and Selective Activator of TRPC4 and TRPC5 Calcium Channels," *Angew. Chem. Int. Ed. Engl.*, 54(12): 3787-3791 (2015).
Akee et al. "Chlorinated Englerins With Selective Inhibition of Renal Cancer Cell Growth," *J. Nat. Prod.*, 75(3): 459-463 (2012).
Amijs et al., "Gold(I)-Catalyzed Intermolecular Addition of Carbon Nucleophiles to 1,5- and 1,6-Enynes," *J. Org. Chem.*, 73(19): 7721-7730 (2008).
Carson et al., "Englerin A agonizes the TRPC4/C5 cation channels to inhibit tumor cell line proliferation," *PLoS One*, 10(6): e0127498 (2015).
Chan et al., "Chemical Synthesis and Biological Evaluation of the Englerin Analogues," *ChemMedChem.*, 6(3): 420-423 (2011).
Fash et al., "Synthesis of a stable and orally bioavailable englerin analogue," *Bioorg. Med. Chem. Lett.*, 26(11): 2641-2644 (2016).
Gaunt et al., "Transient receptor potential canonical 4 and 5 proteins as targets in cancer therapeutics," *Eur. Biophys. J.*, 45(7): 611-620 (2016).
López-Suarez et al., "Synthesis and biological evaluation of new (−)-englerin analogues," *ChemMedChem.*, 11(9): 1003-1007 (2016).
Ludlow et al., "(−)-Englerin A-evoked cytotoxicity is mediated by $Na^+$ influx and counteracted by $Na^+/K^+$-ATPase," *J. Biol. Chem.*, 292(2): 723-731 (2016).
Molawi et al., "Enantioselective Synthesis of (−)-Englerins A and B," *Angew. Chem. Int. Ed.*, 49(20): 3517-3519 (2010).
Muraki et al., "$Na^+$ Entry Through Heteromeric TRPC4/C1 Channels Mediates (−)Englerin A-induced Cytotoxicity in Synovial Sarcoma Cells," *Scientific Reports*, 7(1): 16988 (2017).
Nakatsuji et al., "General, Robust, and Stereocomplementary Preparation of β-Ketoester Enol Tosylates as Cross-Coupling Partners Utilizing TsCl-N-Methylimidazole Agents," *Org. Lett.*, 10(11): 2131-2134 (2008).
Nicolaou et al., "Total Synthesis of Englerin A," *J. Am. Chem. Soc.*, 132(23): 8219-8222 (2010).
Radtke et al., "Total Synthesis and Biological Evaluation of (−)-Englerin A and B: Synthesis of Analogues with Improved Activity Profile," *Angew. Chem. Int. Ed.*, 50(17): 3998-4002 (2011).
Ratnayake et al., "Englerin A, a Selective Inhibitor of Renal Cancer Cell Growth, from *Phyllanthus engleri*," *Organic Letters*, 11(1): 57-60 (2009).
Riou et al., "De Novo Synthesis of (+)-Isofregenedol," *J. Org. Chem.*, 73(18): 7436-7439 (2008).
Sourbier et al., "Englerin A Stimulates PKCθ to Inhibit Insulin Signaling and to Simultaneously Activate HSF1: Pharmacologically Induced Synthetic Lethality," *Cancer Cell*, 23(2): 228-237 (2013).
Xu et al., "Formal Synthesis of (−)-Englerin A and Cytotoxicity Studies of Truncated Englerins," *Chem. Asian J.*, 7(5): 1052-1060 (2012).
European Patent Office, International Preliminary Report on Patentability in International Patent Application No. PCT/US2018/040910 (dated Jan. 16, 2020).
European Patent Office, International Search Report in International Patent Application No. PCT/US2018/040910 (dated Sep. 5, 2018).
European Patent Office, Written Opinion of the International Searching Authority in International Patent Application No. PCT/US2018/040910 (dated Sep. 5, 2018).
Wu et al., "Bridgehead Modifications of Englerin A Reduce TRPC4 Activity and Intravenous Toxicity but not Cell Growth Inhibition," *ACS Med. Chem. Lett.*, 11(9): 1711-1716 (2020).
Wu et al., "Bridgehead Modifications of Englerin A Reduce TRPC4 Activity and Intravenous Toxicity but not Cell Growth Inhibition," *ACS Med. Chem. Lett.*, Supporting Information, pp. 1-123 (2020).

\* cited by examiner

ENGLERIN DERIVATIVES FOR TREATMENT OF CANCER

CROSS-REFERENCE TO RELATED APPLICATIONS

This patent application is a U.S. national phase of International Patent Application No. PCT/US2018/040910, filed Jul. 5, 2018, which claims the benefit of U.S. Provisional Patent Application No. 62/529,063, filed Jul. 6, 2017, the disclosures of which are incorporated by reference for all purposes.

STATEMENT REGARDING FEDERALLY SPONSORED RESEARCH AND DEVELOPMENT

This invention was made with Government support under project number ZIA BC011470 05 funded by the National Institutes of Health, National Cancer Institute. The Government has certain rights in this invention.

BACKGROUND OF THE INVENTION

Cancer is a major cause of death; for example, renal cancer is an important contributor to morbidity and mortality. Current therapies are lacking due to incomplete therapeutic responses and potential adverse side effects, so new therapies are always sought after (Ratanyake et al., *Organic Letters* 2008, 11, 1, 57-60). Attempts have been made to identify and isolate medicinal products for cancer treatment from plant materials. For example, a large number of *Phyllanthus* species have been found in tropical and subtropical regions of the world and some have been used in traditional medicines. Englerin A and englerin B have been isolated and purified from the root bark and stem bark of the plant *Phyllanthus engleri* Pax (Euphorbiaceae). Since then, englerin compounds and derivatives thereof have been studied as potential therapeutics. See, e.g., International Patent Application WO 2013/106226, International Patent Application WO 2014/078350, International Patent Application WO 2012/084267, Radtke et al., *Angew. Chem. Int. Ed.* 2011, 50, 3998, 49, 3517-3519, Nicolaou et al., *J. Am. Chem. Soc.* 2010, 132, 8219-8222, Akee et al., *J. Nat. Prod.* 2012, 75, 459-463, Xu et al., *Chem. Asian J.* 2012, 7, 1052-1060, and Chan et al., *Chem. Med. Chem.* 2011, 6(3), 420-423.

In one possible mechanism, englerin compounds are believed to bind to and activate protein kinase C theta (PKCθ), an isoform found in T cells, muscle, and kidney cancers. The ability to stimulate PKCθ by englerin compounds leads to, e.g., cell cytotoxicity, insulin inhibition, and selective activation of viral replication in T cells. See, e.g., International Patent Application WO 2014/078350 and Sourbier et al., *Cancer Cell*, 2013, 23(2), 228-337.

There continues to exist an unmet need for additional englerin derivatives to provide treatments for cancer associated with PKCθ, such as renal cancer.

BRIEF SUMMARY OF THE INVENTION

The invention provides a compound of formula (I)

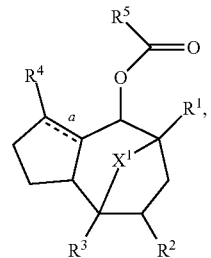

in which "a," $R^1$-$R^5$, and $X^1$ are as described herein.

The present invention further provides a pharmaceutical composition comprising a compound of the invention and a pharmaceutically acceptable carrier.

In one possible mechanism, englerin A activates transient receptor potential canonical (TRPC) ion channels on kidney cancer cell surfaces, thereby increasing the influx of $Ca^{2+}$ and killing the cancer cells (Akbulut et al., *Angew. Chem. Int. Ed.*, 2015, 54, 3787-3791). However, more recently, Beech has shown that sodium influx, not calcium influx, kills the cancer cells (Muraki et al., *Scientific Reports*, 2017, 7, 16988). Englerin A has been shown to be an agonist of TRPC4/C5, but englerin A is lethal in rodents at doses required to activate the TRPC4 channel (Carson et al., *PLoS One*, 2015, 10(6), 1-21). It was surprisingly discovered that compounds of formula (I) are therapeutically active in killing cancer cells, which was particularly unexpected, because the compounds of formula (I) were inactive as agonists of TRPC4. Without wishing to be bound by any theory, it is believed that TRPC4 agonism accounts for the lethality of englerin A. Because the compounds of formula (I) are not agonists of TRPC4, it is believed that the englerin analogs of formula (I) are less toxic to a subject in treating cancer. Accordingly, the present invention also provides a method of treating cancer in a subject in need thereof comprising administering to the subject an effective amount of the compound.

BRIEF DESCRIPTION OF THE SEVERAL VIEWS OF THE DRAWINGS

FIG. 5A depicts the dose response curves against leukemia cell lines. FIG. 5B depicts the dose response curves against non-small cell lung cancer cell lines. FIG. 5C depicts the dose response curves against colon cancer cell lines. FIG. 5D depicts dose response curves against central nervous system (CNS) cancer cell lines. FIG. 5E depicts dose response curves against melanoma cell lines. FIG. 5F depicts dose response curves against ovarian cancer cell lines. FIG. 5G depicts dose response curves against renal cancer cell lines. FIG. 5H depicts dose response curves against prostate cancer cell lines. FIG. 5I depicts dose response curves against breast cancer cell lines.

FIG. 6A depicts the dose response curves against leukemia cell lines. FIG. 6B depicts the dose response curves against non-small cell lung cancer cell lines. FIG. 6C depicts the dose response curves against colon cancer cell lines. FIG. 6D depicts dose response curves against central nervous system (CNS) cancer cell lines. FIG. 6E depicts dose response curves against melanoma cell lines.

FIG. 6F depicts dose response curves against ovarian cancer cell lines. FIG. 6G depicts dose response curves against renal cancer cell lines. FIG. 6H depicts dose response curves against prostate cancer cell lines. FIG. 6I depicts dose response curves against breast cancer cell lines.

FIG. 7A depicts the dose response curves against leukemia cell lines. FIG. 7B depicts the dose response curves against non-small cell lung cancer cell lines. FIG. 7C depicts the dose response curves against colon cancer cell lines. FIG. 7D depicts dose response curves against central nervous system (CNS) cancer cell lines. FIG. 7E depicts dose response curves against melanoma cell lines. FIG. 7F depicts dose response curves against ovarian cancer cell lines. FIG. 7G depicts dose response curves against renal cancer cell lines. FIG. 7H depicts dose response curves against prostate cancer cell lines. FIG. 7I depicts dose response curves against breast cancer cell lines.

FIG. 8A depicts the dose response curves against leukemia cell lines. FIG. 8B depicts the dose response curves against non-small cell lung cancer cell lines. FIG. 8C depicts the dose response curves against colon cancer cell lines. FIG. 8D depicts dose response curves against central nervous system (CNS) cancer cell lines. FIG. 8E depicts dose response curves against melanoma cell lines. FIG. 8F depicts dose response curves against ovarian cancer cell lines. FIG. 8G depicts dose response curves against renal cancer cell lines. FIG. 8H depicts dose response curves against prostate cancer cell lines. FIG. 8I depicts dose response curves against breast cancer cell lines.

FIG. 9A depicts the dose response curves against leukemia cell lines. FIG. 9B depicts the dose response curves against non-small cell lung cancer cell lines. FIG. 9C depicts the dose response curves against colon cancer cell lines. FIG. 9D depicts dose response curves against central nervous system (CNS) cancer cell lines. FIG. 9E depicts dose response curves against melanoma cell lines. FIG. 9F depicts dose response curves against ovarian cancer cell lines. FIG. 9G depicts dose response curves against renal cancer cell lines. FIG. 9H depicts dose response curves against prostate cancer cell lines. FIG. 9I depicts dose response curves against breast cancer cell lines.

FIG. 10A depicts the dose response curves against leukemia cell lines. FIG. 10B depicts the dose response curves against non-small cell lung cancer cell lines. FIG. 10C depicts the dose response curves against colon cancer cell lines. FIG. 10D depicts dose response curves against central nervous system (CNS) cancer cell lines. FIG. 10E depicts dose response curves against melanoma cell lines. FIG. 10F depicts dose response curves against ovarian cancer cell lines. FIG. 10G depicts dose response curves against renal cancer cell lines. FIG. 10H depicts dose response curves against prostate cancer cell lines. FIG. 10I depicts dose response curves against breast cancer cell lines.

FIG. 11A depicts the dose response curves against leukemia cell lines. FIG. 11B depicts the dose response curves against non-small cell lung cancer cell lines. FIG. 11C depicts the dose response curves against colon cancer cell lines. FIG. 11D depicts dose response curves against central nervous system (CNS) cancer cell lines. FIG. 11E depicts dose response curves against melanoma cell lines. FIG. 11F depicts dose response curves against ovarian cancer cell lines. FIG. 11G depicts dose response curves against renal cancer cell lines. FIG. 11H depicts dose response curves against prostate cancer cell lines. FIG. 11I depicts dose response curves against breast cancer cell lines.

DETAILED DESCRIPTION OF THE INVENTION

Figure 1:
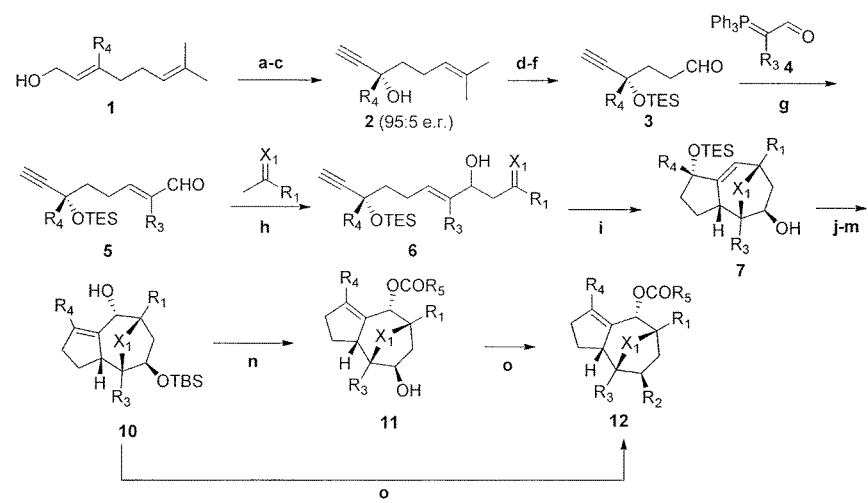
FIG. 1 is a chemical scheme of the synthesis of a compound of formula (I). Reagents and conditions: a) L-(+)-diethyl tartrate, Ti(OiPr)$_4$, tert-butylhydroperoxide, CH$_2$Cl$_2$, −40° C., 4 h, 9:1 e.r.; b) CCl$_4$, PPh$_3$, 80° C., 6 h; c) nBuLi (3.5 equiv), THF, −40° C., 2 h; d) TESOTf, Et$_3$N, CH$_2$Cl$_2$, 23° C., 3 h; e) AD-mix-α, tBuOH/H$_2$O (1:1), 23° C., 10 h; f) NaIO$_4$/SiO$_2$, CH$_2$Cl$_2$, 23° C., 10 h; g) 4 (1.6 equiv), benzene, reflux, 2 days. h) lithium diisopropylamide (LDA), R$_1$COMe, THF, −78° C., 15 h; i) [IPrAuNCPh]SbF$_6$ (3 mol %), CH$_2$Cl$_2$, 23° C., 5 h; j) TBAF, THF, 23° C., 12 h; k) 4-dimethylaminopyridine (DMAP), imidazole, TBDMSCl, 23° C.; l) CrO$_3$, pyridine, CH$_2$Cl$_2$, 23° C., 1 h and CeCl$_3$ (H$_2$O)$_7$, NaBH$_4$, MeOH, 23° C., 5 min; m) WCl$_6$ (2 equiv), nBuLi (4 equiv), THF, 0 to 50° C., 2 h; n) R$_5$COCl, DMAP, Et$_3$N, CH$_2$Cl$_2$, 45° C. 4-12 h and TBAF, THF, 23° C., 12 h; o) R$_2$COOH, DMAP, NEt$_3$, 2,4,6-trichlorobenzoyl chloride, toluene, 23° C., 1 h and TBAF, AcOH, THF, 4 h, 23° C.

The invention provides a compound of formula (I)

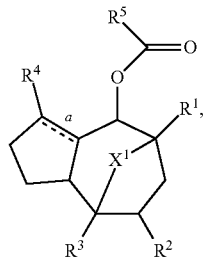

(I)

wherein

"a" represents a single bond or double bond;

$R^1$ is $C_3$-$C_6$ cycloalkyl, heterocycloalkyl, aryl, or heteroaryl, each of the foregoing is optionally substituted;

$R^2$ is selected from hydroxy, alkoxy, $-X^2-(CX^3)-(CR^6R^7)_m-X^2-(CX^3)-R^8$, $-X^2-(CX^3)-(CR^6R^7)_m-R^8$, and $-X^2-(CX^3)-(CR^6R^7)_m-X^2-R^{18}$;

$R^6$ and $R^7$ are independently selected from hydrogen, hydroxy, fluorine, chlorine, and $C_1$-$C_6$ alkyl;

$R^8$ is selected from $C_1$-$C_6$ alkyl, fluoro $C_1$-$C_6$ alkyl, heterocycloalkyl, aryl, heteroaryl, alkoxy, and aryloxy, each of the foregoing is optionally substituted, hydroxy, and $-NR^{15}R^{16}$;

$R^{15}$ and $R^{16}$ are independently selected from hydrogen and $C_1$-$C_6$ alkyl; or $R^{16}$ is $COOR^{17}$;

$R^{17}$ is $C_1$-$C_6$ alkyl;

$R^{18}$ is selected from $C_1$-$C_6$ alkyl, fluoro $C_1$-$C_6$ alkyl, aryl, and heteroaryl, each of which is optionally substituted;

each $X^2$ is independently selected from O, S and $NR^{15}$;

$X^3$ is selected from O and S;

$R^3$ and $R^4$ are independently a $C_1$-$C_6$ alkyl;

$R^5$ is selected from $-(CR^9R^{10})_n-R^{11}$ and $-(CR^{12}=CR^{13})_n-R^{14}$;

$R^9$ and $R^{10}$ are independently selected from hydrogen and $C_1$-$C_6$ alkyl; or alternatively $R^9$ and $R^{10}$, together with the carbon to which they are attached, form a $C_3$-$C_6$ cycloalkyl;

$R^{11}$ and $R^{14}$ are independently selected from $C_1$-$C_6$ alkyl, $C_3$-$C_6$ cycloalkyl, aryl, and heteroaryl, each of which is optionally substituted;

$R^{12}$ and $R^{13}$ are independently selected from hydrogen, halogen, and $C_1$-$C_6$ alkyl;

$X^1$ is selected from O, $NR^{15}$, and S; and n and m are independently selected from 0 and an integer of 1-3, provided that when "a" is a double bond, $R^1$ is heterocycloalkyl, which is optionally substituted;

or a pharmaceutically acceptable salt thereof.

The compound of formula (I) can have any suitable stereochemistry and can be in the form of a single stereoisomer, a mixture of two or more stereoisomers (e.g., an epimer, a mixture of diastereomers and/or enantiomers, a racemic mixture). In an embodiment, the compound of formula (I) has the stereochemistry of formula (I'):

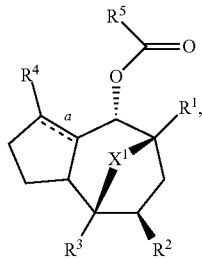

(I')

In any of the embodiments of the invention, $X^1$ preferably is O.

In any of the embodiments, $R^2$ can be selected from hydroxy, alkoxy, radicals of formula $-X^2-(CO)-(CR^6R^7)_m-X^2-(CO)-R^8$, radicals of formula $-X^2-(CO)-R^8$, radicals of formula $-X^2-CO-X^2-R^{18}$, and radicals of formula $-X^2-C(O)-(CR^6R^7)_m-R^8$. In certain embodiments, $R^2$ is selected from hydroxy, alkoxy, and radicals of formula $-X^2-C(O)-(CR^6R^7)_m-R^8$. In some aspects, $R^2$ is selected from hydroxy and a radical of formula $-X^2-C(O)-(CR^6R^7)_m-R^8$, in which $R^6$ is hydrogen, $R^7$ is selected from hydrogen and $C_1$-$C_6$ alkyl; $R^8$ is selected from $C_1$-$C_6$ alkyl, hydroxy, $-NH_2$, and $-NHCOOC_4H_9$, in which $X^2$ is O or NH; and m is 0 or 1. More specifically, in some embodiments of the invention, $R^2$ is selected from $-OH$, $-OCOMe$, $-OCOCH_2OH$, $-NHC(O)CH_2OH$, $-OCOCH(CH_3)OH$, $-NHCOCH(CH_3)OH$, $-OCOCH_2NH_2$, $-NHCOCH_2NH_2$, $-OCOCH(CH_3)NH_2$, $-NHCOCH(CH_3)NH_2$, $-OCOCH(CH_3)NHCOC_4H_9$, and $-NHCOCH(CH_3)NHCOC_4H_9$.

In any of the embodiments of the invention, $R^5$ is selected from $-(CR^9R^{10})_n-R^{11}$ and $-(CR^{12}=CR^{13})_n-R^{14}$; in which $R^9$ and $R^{10}$ are independently selected from hydrogen and $C_1$-$C_6$ alkyl, or alternatively, $R^9$ and $R^{10}$, together with the carbon to which they are attached, form a $C_3$-$C_6$ cycloalkyl; $R^{11}$ and $R^{14}$ are independently selected from $C_1$-$C_6$ alkyl and aryl, each of which is optionally substituted; and $R^{12}$ and $R^{13}$ are independently selected from hydrogen and optionally substituted $C_1$-$C_6$ alkyl.

In any of the embodiments of the invention, $R^5$ is $-(CR^9R^{10})_n-R^{11}$, $R^9$ and $R^{10}$ are each hydrogen, $R^{11}$ is phenyl, and n is 1-3. Preferably, n is 3 so as to form a radical of formula $-(CH_2)_3Ph$.

Alternatively, in any of the embodiments of the invention, $R^5$ is $-(CR^9R^{10})_n-R^{11}$, n is 0, and $R^{11}$ is $C_1$-$C_6$ alkyl or aryl (e.g., phenyl, naphthyl), which of which is optionally substituted. More preferably, $R^5$ is methyl, phenyl, naphthyl, or methyl-substituted naphthyl.

Alternatively, in any of the embodiments of the invention, $R^5$ is $-(CR^9R^{10})_n-R^{11}$, $R^9$ and $R^{10}$, together with the carbon to which they are attached, form a $C_3$-$C_6$ cycloalkyl, $R^{11}$ is phenyl, and n is 1 or 2. The $C_3$-$C_6$ cycloalkyl is optionally substituted cyclopropyl, optionally substituted cyclobutyl, optionally substituted cyclopentyl, or optionally substituted cyclohexyl. In particular, $R^9$ and $R^{10}$, together with the carbon atom to which they are attached, form a cyclopropyl (e.g., attached at the 1- and 2-positions). More particularly, $R^5$ is 2-phenylcyclopropyl.

$R^9$, $R^{10}$, and the carbon to which they are attached can be attached to the carbonyl (C=O) and $R^{11}$ at any suitable positions (e.g., any combination of the 1-position, the 2-position, the 3-position, the 4-position, the 5-position, and the 6-position). For example, $R^9$, $R^{10}$, and the carbon to which they are attached can be attached to the carbonyl (C=O) and $R^{11}$ at the 1- and 2-positions, the 1- and 3-positions, the 1- and 4-positions, the 1- and 5-positions, the 2- and 3-positions, the 2- and 4-positions, the 3- and 4-positions, etc.

Alternatively, in any of the embodiments of the invention, $R^5$ is —(CR$^{12}$=CR$^{13}$)$_n$—R$^{14}$, $R^{12}$ and $R^{13}$ are each hydrogen or $C_1$-$C_6$ alkyl (e.g., methyl, ethyl), $R^{14}$ is cycloalkyl or phenyl, and n is 1-3. Preferably, n is 1 so as to form a radical of formula —(CH=CH)cyclohexyl, —(CH=C(alkyl))cyclohexyl, —(CH=CH)Ph, or —(CH=C(alkyl))Ph.

In any of the foregoing embodiments, "a" is a single bond or a double bond.

In certain embodiments, "a" is a double bond and $R^1$ is heterocycloalkyl, which is optionally substituted. In such embodiments, the heterocycloalkyl can be, for example, aziridinyl, oxiranyl, thiazolinyl, imidazolidinyl, piperazinyl, homopiperazinyl, pyrrolinyl, pyrrolidinyl, tetrahydrofuranyl, tetrahydrothiofuranyl, pyranyl, tetrahydropyranyl, piperidinyl, morpholinyl, or thiomorpholinyl, each of which is optionally substituted. In a preferred embodiment, the heterocycloalkyl is a piperidinyl of the formula

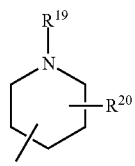

wherein $R^{19}$ is hydrogen, $C_1$-$C_6$ alkyl or $C_1$-$C_6$ alkylcarbonyl, each of which, other than hydrogen, is optionally substituted; and $R^{20}$ is hydrogen, halo, $C_1$-$C_6$ alkyl, $C_1$-$C_6$ alkenyl, $C_1$-$C_6$ alkynyl, hydroxy, nitro, cyano, amino, $C_1$-$C_6$ alkylamino, $C_1$-$C_6$ alkoxy, aryloxy, $C_1$-$C_6$ aralkoxy, carboxyl, carboxy-$C_1$-$C_6$ alkyl, carboxy-$C_1$-$C_6$ alkyloxy, amido, $C_1$-$C_6$ alkylamido, halo-$C_1$-$C_6$ alkylamido, aryl, heteroaryl, or heterocycloalkyl, or a pharmaceutically acceptable salt thereof. The piperidinyl can attach to the core structure of formula (I) at any suitable position (e.g., 1-, 2-, 3-, or 4-position), but preferably, the piperidinyl group attaches to the core structure at the 4-position.

In certain embodiments, "a" is a single bond and $R^1$ is $C_3$-$C_6$ cycloalkyl, heterocycloalkyl, aryl, or heteroaryl, each of which is optionally substituted. In some of these embodiments, $R^1$ is cyclopropyl, cyclobutyl, cyclopentyl, cyclohexyl, phenyl, naphthyl, aziridinyl, oxiranyl, thiazolinyl, imidazolidinyl, piperazinyl, homopiperazinyl, pyrrolinyl, pyrrolidinyl, tetrahydrofuranyl, tetrahydrothiofuranyl, pyranyl, tetrahydropyranyl, piperidinyl, morpholinyl, thiomorpholinyl, pyridinyl, furanyl, pyrrolyl, quinolinyl, thiophenyl, indolyl, oxazolyl, isoxazolyl, pyrazolyl, imidazolyl, thiazolyl, isothiazolyl, 1,3,4-thiadiazolyl, pyridazinyl, pyrimidinyl, pyrazinyl, or triazinyl, each of which is optionally substituted. In preferred embodiments, $R^1$ is $C_3$-$C_6$ cycloalkyl (e.g., cyclopropyl or cyclohexyl) or phenyl, any of which is optionally substituted.

Specific examples of the compound of formula (I) are:

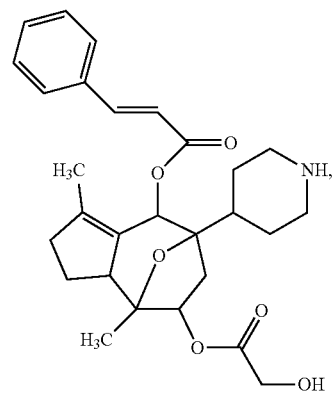

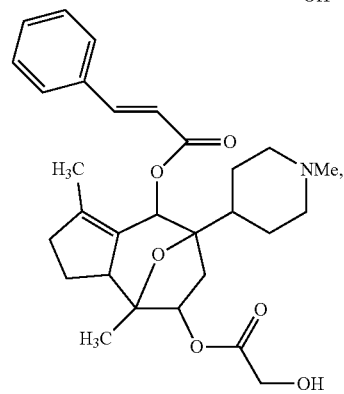

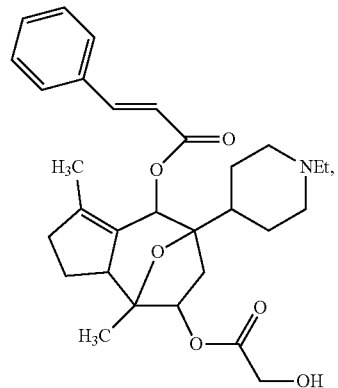

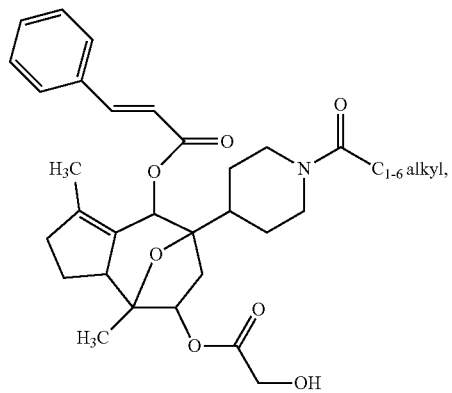

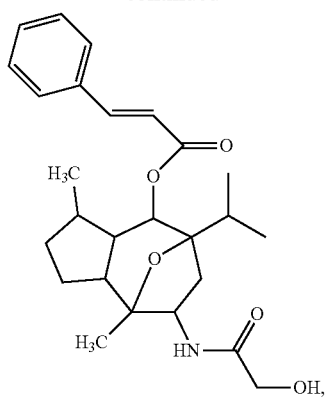
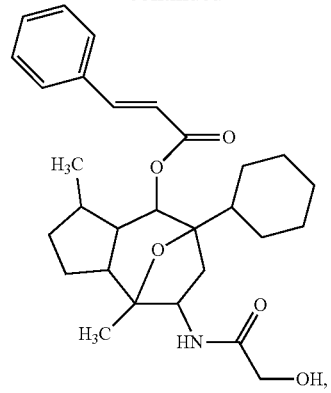
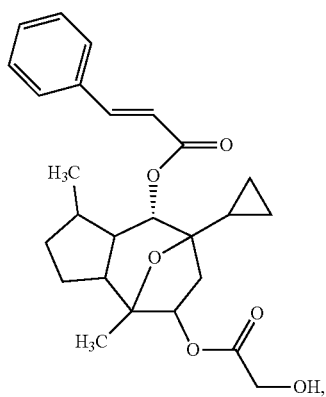
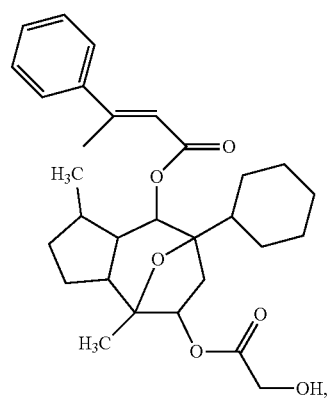
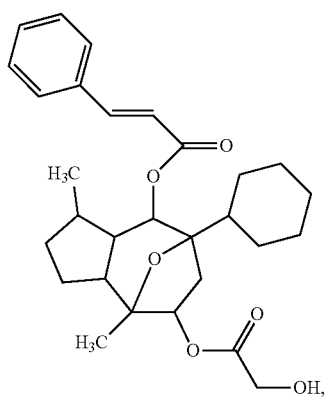
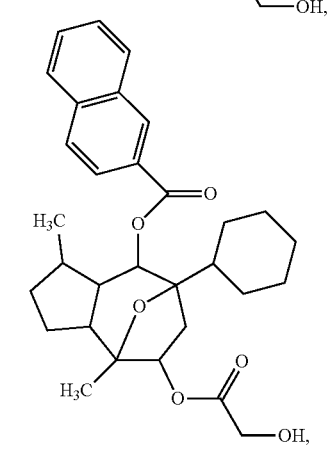

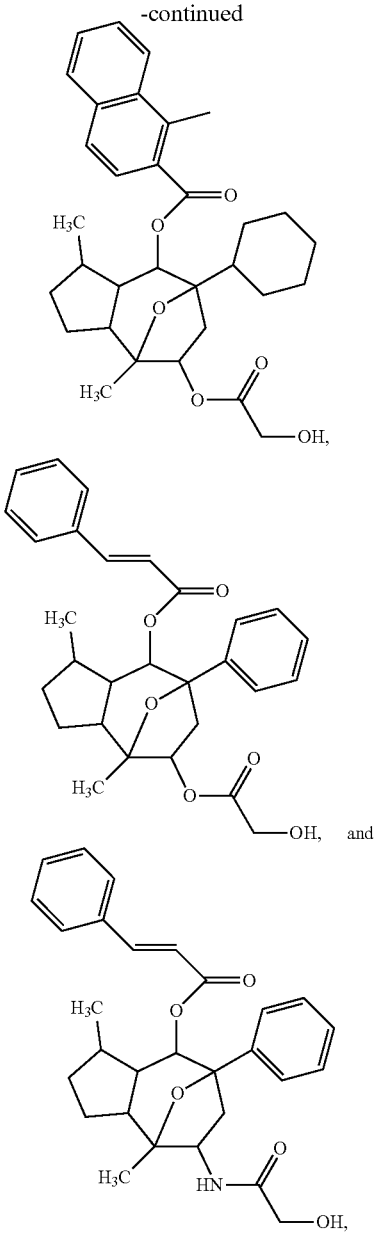
or a pharmaceutically acceptable salt thereof.
Specific examples of the compound of formula (I') are:
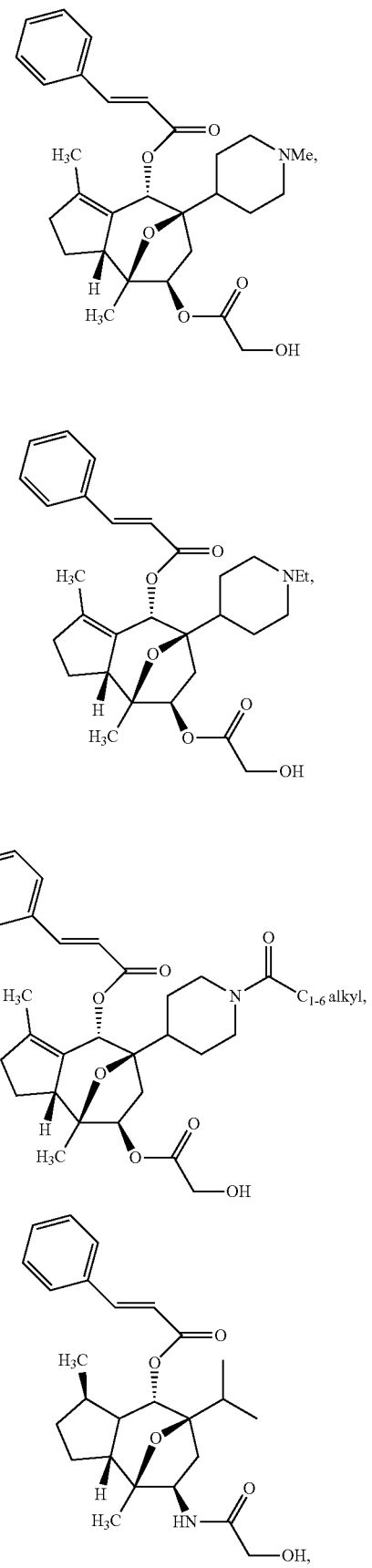

13
-continued
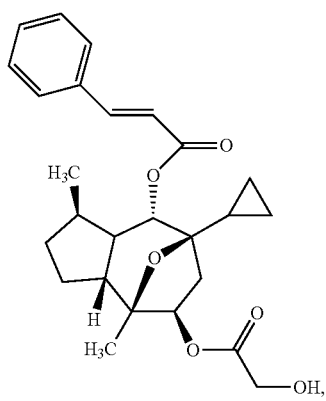
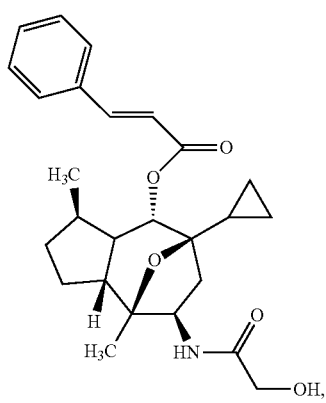
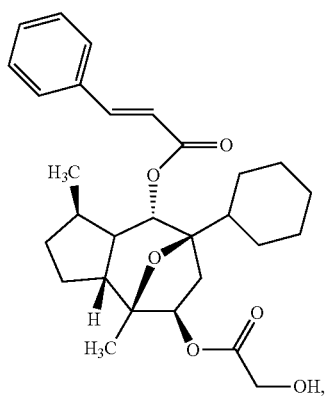
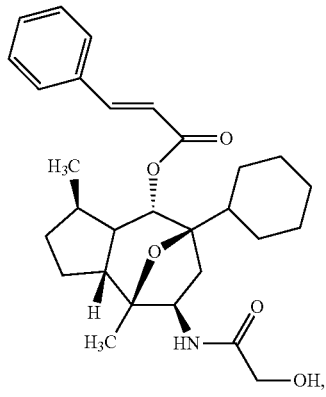
14
-continued
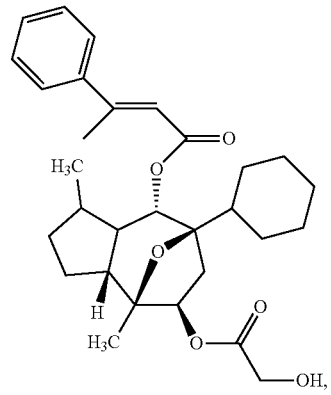
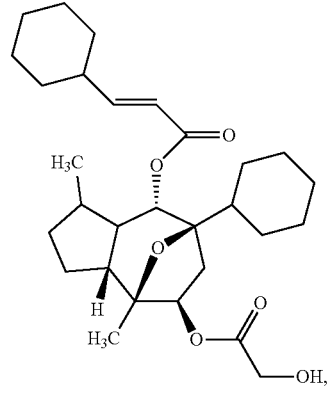
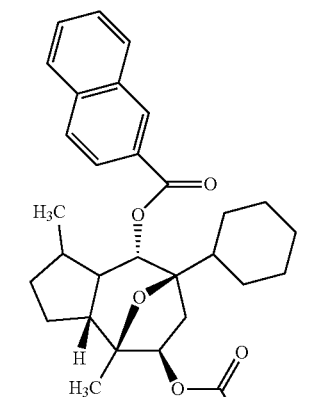
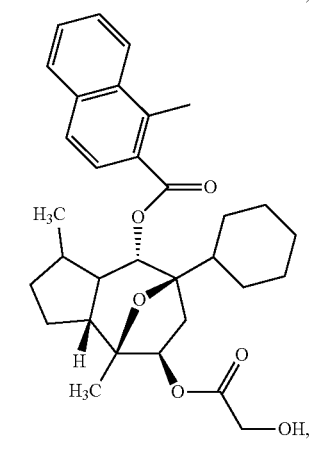

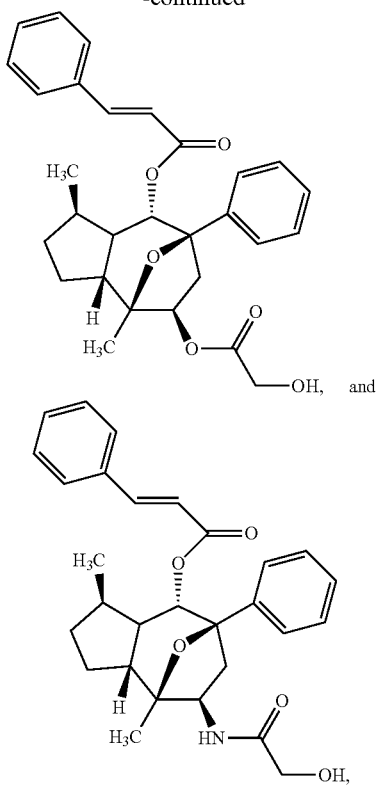

or a pharmaceutically acceptable salt thereof.

In any of the embodiments above, the term "alkyl" implies a straight-chain or branched alkyl substituent containing from, for example, from about 1 to about 6 carbon atoms, e.g., from about 1 to about 4 carbon atoms or about 1 to about 3 carbons. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs as part of a group, such as, e.g., fluoro $C_1$-$C_6$ alkyl. The alkyl can be substituted or unsubstituted, as described herein.

In any of the embodiments above, the term "alkenyl," as used herein, means a linear alkenyl substituent containing from, for example, 2 to about 6 carbon atoms (branched alkenyls are about 3 to about 6 carbons atoms), e.g., from about 3 to about 6 carbon atoms (branched alkenyls are about 3 to about 6 carbons atoms). In accordance with an embodiment, the alkenyl group is a $C_2$-$C_4$ alkenyl. Examples of alkenyl group include ethenyl, allyl, 2-propenyl, 1-butenyl, 2-butenyl, 1-pentenyl, 2-pentenyl, 3-pentenyl, 1-hexenyl, and the like. The alkenyl can be substituted or unsubstituted, as described herein.

In any of the embodiments above, the term "cycloalkyl," as used herein, means a cyclic alkyl moiety containing from, for example, 3 to 6 carbon atoms or from 5 to 6 carbon atoms. Examples of such moieties include cyclopropyl, cyclobutyl, cyclopentyl, cyclohexyl, and the like. The cycloalkyl can be substituted or unsubstituted, as described herein.

The term "heterocycloalkyl" means a stable, saturated, or partially unsaturated monocyclic, bicyclic, and spiro ring system containing 3 to 7 ring members of carbon atoms and other atoms selected from nitrogen, sulfur, and/or oxygen. In an aspect, a heterocycloalkyl is a 5, 6, or 7-membered monocyclic ring and contains one, two, or three heteroatoms selected from nitrogen, oxygen, and sulfur. The heterocycloalkyl may be attached to the parent structure through a carbon atom or through any heteroatom of the heterocycloalkyl that results in a stable structure. Examples of such heterocycloalkyl rings are aziridinyl, oxiranyl, thiazolinyl, imidazolidinyl, piperazinyl, homopiperazinyl, pyrrolinyl, pyrrolidinyl, tetrahydrofuranyl, tetrahydrothiofuranyl, pyranyl, tetrahydropyranyl, piperidinyl, and morpholinyl. The heterocycloalkyl can be substituted or unsubstituted, as described herein.

In any of the embodiments above, the term "hydroxy" refers to the group —OH.

In any of the embodiments above, the terms "alkoxy" and "aryloxy" embrace linear or branched alkyl and aryl groups that are attached to a divalent oxygen. The alkyl and aryl groups are the same as described herein.

In any of the embodiments above, the term "halo" refers to a halogen selected from fluorine, chlorine, bromine, and iodine.

In any of the embodiments above, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, from 6 to 18 carbon atoms, from 6 to 14 carbon atoms, or from 6 to 10 carbon atoms. It is understood that the term aryl includes carbocyclic moieties that are planar and comprise 4n+2 π electrons, according to Hückel's Rule, wherein n=1, 2, or 3. The aryl can be substituted or unsubstituted, as described herein.

In any of the embodiments above, the term "heteroaryl" refers to an aryl as defined above in which at least one, preferably 1 or 2, of the carbon atoms of the aromatic carbocyclic ring is replaced by N, O, or S atoms. In particular, "heteroaryl" includes aromatic 5 or 6 membered monocyclic groups, 9 or 10 membered bicyclic groups, and 11 to 14 membered tricyclic groups, which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. In other words, heteroaryl groups that are bicyclic or tricyclic must include at least one fully aromatic ring but the other fused ring or rings may be aromatic or non-aromatic. The nitrogen and sulfur atoms can optionally be oxidized, and the nitrogen atoms may optionally be quaternized. The heteroaryl group can be attached at any available nitrogen or carbon atom of any ring. Examples of heteroaryl include pyridinyl, furanyl, pyrrolyl, quinolinyl, thiophenyl, indolyl, oxazolyl, isoxazolyl, pyrazolyl, imidazolyl, thiazolyl, isothiazolyl, 1,3,4-thiadiazolyl, pyridazinyl, pyrimidinyl, pyrazinyl, and triazinyl.

In other aspects, any substituent that is not hydrogen (e.g., $C_1$-$C_6$ alkyl, $C_2$-$C_6$ alkenyl, $C_3$-$C_6$ cycloalkyl, heterocycloalkyl, aryl, or heteroaryl) can be an optionally substituted moiety. The substituted moiety typically comprises at least one substituent (e.g., 1, 2, 3, 4, 5, 6, etc.) in any suitable position (e.g., 1-, 2-, 3-, 4-, 5-, or 6-position, etc.). When a group, such alkyl, cycloalkyl, aryl, heteroaryl, etc., is substituted with a substituent, e.g., halo, amino, alkyl, OH, alkoxy, cyano, nitro, and others, a hydrogen on the group is replaced with the substituent and this can take place in any of the available hydrogens, e.g., 2, 3, 4, 5, and/or 6-position wherein the 1-position is the point of attachment of the group in the compound of the present invention. Suitable substituents include, e.g., halo, alkyl, alkenyl, alkynyl, hydroxy, nitro, cyano, amino, alkylamino, alkoxy, aryloxy, aralkoxy, carboxyl, carboxyalkyl, carboxyalkyloxy, amido, alkylamido, haloalkylamido, aryl, heteroaryl, and heterocycloalkyl. In some instances, the substituent is one or more (e.g., 1 or 2) moieties selected from alkyl, halo, and/or haloalkyl.

In any of the embodiments above, whenever a range of the number of atoms in a structure is indicated (e.g., a $C_{1-6}$, or $C_{1-4}$ alkyl, $C_3$-$C_6$ cycloalkyl, etc.), it is specifically contemplated that any sub-range or individual number of carbon atoms falling within the indicated range also can be used. Thus, for instance, the recitation of a range of 1-6 carbon atoms (e.g., $C_1$-$C_6$), 1-4 carbon atoms (e.g., $C_1$-$C_4$), 1-3 carbon atoms (e.g., $C_1$-$C_3$), or 2-6 carbon atoms (e.g., $C_2$-$C_6$) as used with respect to any chemical group (e.g., alkyl, cycloalkyl, etc.) referenced herein encompasses and specifically describes 1, 2, 3, 4, 5, and/or 6 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 2-3 carbon atoms, 2-4 carbon atoms, 2-5 carbon atoms, 2-6 carbon atoms, 3-4 carbon atoms, 3-5 carbon atoms, 3-6 carbon atoms, 4-5 carbon atoms, 4-6 carbon atoms, etc., as appropriate).

The subscripts "m" and "n" represent the number of substituents (e.g., "$(CR^6R^7)$," "$(CR^9R^{10})$," or "$(CR^{12}=CR^{13})$"), in which each instance of a particular substituent (e.g., "$(CR^6R^7)$," "$(CR^9R^{10})$," or "$(CR^{12}=CR^{13})$") can be the same or different. The subscripts m and n can be the same or different and each is either 0 or an integer from 1-3 (i.e., 1, 2, or 3). When m or n is 0, then the corresponding substituent (e.g., "$(CR^6R^7)$," "$(CR^9R^{10})$," or "$(CR^2=CR^{13})$") is not present in the compound of formula (I).

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. For example, an inorganic acid (e.g., hydrochloric acid, sulfuric acid, phosphoric acid, or hydrobromic acid), an organic acid (e.g., oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid), an inorganic base (e.g., sodium hydroxide, potassium hydroxide, calcium hydroxide, magnesium hydroxide, or ammonium hydroxide), an organic base (e.g., methylamine, diethylamine, triethylamine, triethanolamine, ethylenediamine, tris(hydroxymethyl)methylamine, guanidine, choline, or cinchonine), or an amino acid (e.g., lysine, arginine, or alanine) can be used. Generally, nonaqueous media such as ether, ethyl acetate, ethanol, isopropanol, or acetonitrile are typical. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium of salt.

The compounds of formula (I), including a compound of formula (I'), can be prepared by any suitable synthetic methodology. Suitable methods are set forth in the general procedures described below and in FIGS. 1-4.

The methods described herein comprise administering a compound of formula (I), including a compound of formula (I'), or a pharmaceutically acceptable salt thereof in the form of a pharmaceutical composition. In particular, a pharmaceutical composition will comprise at least one compound of formula (I) or (I') or a pharmaceutically acceptable salt thereof and a pharmaceutically acceptable carrier. The pharmaceutically acceptable excipients described herein, for example, vehicles, adjuvants, carriers or diluents, are well-known to those who are skilled in the art and are readily available to the public. Typically, the pharmaceutically acceptable carrier is one that is chemically inert to the active compounds and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously.

In accordance with any of the embodiments, the compound of formula (I), including a compound of formula (I'), or a pharmaceutically acceptable salt thereof can be administered orally to a subject in need thereof. Formulations suitable for oral administration can consist of (a) liquid solutions, such as an effective amount of the compound dissolved in diluents, such as water, saline, or orange juice and include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I) or (I') or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the compound of formula (I) in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compound of formula (I), including a compound of formula (I'), can be made into an injectable formulation. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topically applied compositions are generally in the form of liquids (e.g., mouthwash), creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution, such as a mouthwash. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The compound of formula (I), including a compound of formula (I'), or a pharmaceutically acceptable salt thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

It will be appreciated by a person of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.* 1980, 9, 467 and U.S. Pat. Nos. 4,235,871, 4,501,728, 4,837,028, and 5,019,369.

The dose administered to the subject, particularly a human and other mammals, in accordance with the present invention should be sufficient to affect the desired response. One skilled in the art will recognize that dosage will depend upon a variety of factors, including the age, condition or disease state, predisposition to disease, genetic defect or defects, and body weight of the subject. The size of the dose will also be determined by the route, timing and frequency of administration as well as the existence, nature, and extent of any adverse side-effects that might accompany the administration of a particular inhibitor and the desired effect. It will be appreciated by one of skill in the art that various conditions or disease states may require prolonged treatment involving multiple administrations.

The inventive methods comprise administering an effective amount of a compound of formula (I), including a compound of formula (I'), or a pharmaceutically acceptable salt thereof. An "effective amount" means an amount sufficient to show a meaningful benefit in an individual, e.g., promoting at least one aspect of tumor cell cytotoxicity (e.g., inhibition of growth, inhibiting survival of a cancer cell, reducing proliferation, reducing size and/or mass of a tumor (e.g., solid tumor)), or treatment, healing, prevention, delay of onset, inhibiting, halting, or amelioration of other relevant medical condition(s) and/or symptom associated with cancer (e.g., renal cancer, prostate cancer, breast cancer, bladder cancer, or Ewing's sarcoma). The meaningful benefit observed in the mammal can be to any suitable degree (e.g., 10%, 20%, 30%, 40%, 50%, 60%, 70%, 80%, 90%, 95%, 99% or more). In some aspects, one or more symptoms of the cancer is prevented, reduced, ameliorated, inhibited, halted, or eliminated subsequent to administration of a compound of formula (I), including a compound of formula (I'), or a pharmaceutically acceptable salt thereof, thereby effectively treating the cancer to at least some degree.

Effective amounts may vary depending upon the biological effect desired in the individual, condition to be treated, and/or the specific characteristics of the compound of formula (I) or (I') or a pharmaceutically acceptable salt thereof, and the individual (e.g., a 70 kg patient on average). In this respect, any suitable dose of the compound of formula (I) or (I') or a pharmaceutically acceptable salt thereof can be administered to the subject (e.g., human), according to the type of cancer to be treated. Various general considerations taken into account in determining the "effective amount" are known to those of skill in the art and are described, e.g., in Gilman et al., eds., Goodman And Gilman's: *The Pharmacological Bases of Therapeutics,* 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I) or (I') or a pharmaceutically acceptable salt thereof desirably comprises about 0.001 mg per kilogram (kg) of the body weight of the subject (mg/kg) to about 400 mg/kg. The minimum dose is any suitable amount, such as about 0.001 mg/kg, about 0.005 mg/kg, about 0.0075 mg/kg, about 0.01 mg/kg, about 0.05 mg/kg, about 0.075 mg/kg, about 0.1 mg/kg, about 0.15 mg/kg, about 0.2 mg/kg, about 0.4 mg/kg, about 0.75 mg/kg, about 1 mg/kg, about 2 mg/kg, about 3 mg/kg, about 5 mg/kg, about 10 mg/kg, about 15 mg/kg, about 20 mg/kg, about 30 mg/kg, about 50 mg/kg, about 60 mg/kg, about 75 mg/kg, about 100 mg/kg, about 150 mg/kg, about 175 mg/kg, about 200 mg/kg, about 250 mg/kg, about 275 mg/kg, or about 300 mg/kg). The maximum dose is any suitable amount, such as about 350 mg/mg, about 300 mg/kg, about 275 mg/kg, about 250 mg/kg, about 200 mg/kg, about 175 mg/kg, about 150 mg/kg, about 100 mg/kg, about 75 mg/kg, about 60 mg/kg, about 50 mg/kg, about 30 mg/kg, about 20 mg/kg, about 15 mg/kg, about 10 mg/kg, about 5 mg/kg, about 3 mg/kg, about 2 mg/kg, about 1 mg/kg, about 0.75 mg/kg, about 0.4 mg/kg, or about 0.2 mg/kg). Any two of the foregoing minimum and maximum doses can be used to define a close-ended range or can be used singly to define an open-ended range.

The invention also provides a method of treating cancer in a subject comprising administering to the subject an effective amount of a compound of formula (I), including a compound of formula (I'), or a pharmaceutically acceptable salt thereof. The cancer can be any suitable cancer, such as cancers of the head and neck, eye, skin, mouth, throat, esophagus, chest, bone, lung, colon, sigmoid, rectum, stomach, prostate, breast, ovaries, kidney, liver, pancreas, brain, intestine, heart, or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's sarcoma (tumor), leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-borne tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, hairy cell leukemia, or multiple myeloma. See, e.g., *Harrison's Principles of Internal Medicine,* Eugene Braunwald et al., eds., pp. 491 762 (15th ed. 2001).

In some aspects, the cancer is leukemia, non-small cell lung cancer, colon cancer, melanoma, prostate cancer, renal cancer, breast cancer, bladder cancer, CNS cancer, ovarian cancer, or Ewing's sarcoma, particularly renal cancer, prostate cancer, breast cancer, bladder cancer, or Ewing's sarcoma. In a preferred embodiment, the cancer is renal cancer.

In accordance with an embodiment of the invention, the compounds of formula (I), including compounds of formula (I'), are active against, e.g., decrease the growth of, renal cancer that is associated with renal cancer cell lines, e.g., 786-0, A-498, ACHN, CAKI-1, RXF 393, SN 12C, TK-10, and UO-31. For example, these compounds have a GI$_{50}$ or IC$_{50}$ of 1 µM or less, preferably 0.1 µM or less. Accordingly, the compounds of formula (I) are considered useful in treating renal cancer in a subject, particularly renal cancer that exhibits characteristics of a renal cancer cell line selected from 786-0, A-498, ACHN, CAKI-1, RXF 393, SN 12C, TK-10, and UO-31.

As used herein, the term "treat" does not necessarily imply complete elimination of cancer. Rather, there are varying degrees of treatment of which a person of ordinary skill in the art recognizes as having a benefit or therapeutic effect. In this respect, the cancer can be treated to any extent through the present inventive method. For example, in a method of treating cancer, at least 10% (e.g., at least 20%, 30%, or 40%) of the growth of a cancerous tumor desirably is inhibited upon administration of a compound described herein. Preferably, at least 50% (e.g., at least 60%, 70%, or 80%) of the growth of a cancerous tumor is inhibited upon administration of a compound described herein. More preferably, at least 90% (e.g., at least 95%, 99%, or 100%) of the growth of a cancerous tumor is inhibited upon administration of a compound described herein. In addition or alternatively, the inventive method may be used to inhibit metastasis of a cancer.

In an aspect, a compound formula (I), including a compound of formula (I'), agonizes TRPC4 to a level that is lower than the same amount (e.g., dose) of englerin A. In an embodiment, a compound of formula (I) does not activate (e.g., agonize) TRPC4. Thus, the method of treating cancer, as described herein, can include the feature that the method is free or substantially free of activation of a TRPC4 receptor in the subject. As used herein, the term "substantially free" means that a concentration of 1 μmol of a compound of formula (I) has 15% or less (e.g., 12% or less, 10% or less, 8% or less, 6% or less, 5% or less, 4% or less, 3% or less, 2% or less, or 1% or less) TRPC4 activation. Alternatively, or in addition, a concentration of 1 μmol of a compound of formula (I) has 15% or less (e.g., 12% or less, 10% or less, 8% or less, 6% or less, 5% or less, 4% or less, 3% or less, 2% or less, or 1% or less) TRPC5 activation.

For purposes of the present invention, the term "subject" typically is directed to a mammal. Mammals include, but are not limited to, the order Rodentia, such as mice, and the order Logomorpha, such as rabbits. In some aspects, the mammals are from the order Carnivora, including Felines (cats) and Canines (dogs), Artiodactyla, including Bovines (cows) and Swines (pigs) or of the order Perssodactyla, including Equines (horses). In some aspects, the mammals are of the order Primates, Ceboids, or Simioids (monkeys) or of the order Anthropoids (humans and apes). In embodiments of the invention, the subject to be treated is a human.

The invention is further illustrated by the following embodiments.

(1) A compound of formula (I)

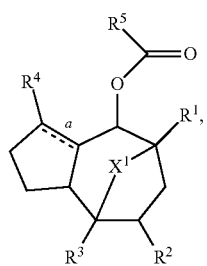

wherein
"a" represents a single bond or double bond;
$R^1$ is $C_3$-$C_6$ cycloalkyl, heterocycloalkyl, aryl, or heteroaryl, each of the foregoing is optionally substituted;
$R^2$ is selected from hydroxy, alkoxy, —$X^2$—$(CX^3)$—$(CR^6R^7)_m$—$X^2$—$(CX^3)$—$R^8$, —$X^2$—$(CX^3)$—$(CR^6R^7)_m$—$R^8$, and —$X^2$—$(CX^3)$—$(CR^6R^7)_m$—$X^2$—$R^{18}$;
  $R^6$ and $R^7$ are independently selected from hydrogen, hydroxy, fluorine, chlorine, and $C_1$-$C_6$ alkyl;
  $R^8$ is selected from $C_1$-$C_6$ alkyl, fluoro $C_1$-$C_6$ alkyl, heterocycloalkyl, aryl, heteroaryl, alkoxy, aryloxy, each of the foregoing is optionally substituted, hydroxy, and —$NR^{15}R^{16}$;
  $R^{15}$ and $R^{16}$ are independently selected from hydrogen and $C_1$-$C_6$ alkyl; or
  $R^{16}$ is $COOR^{17}$;
  $R^{17}$ is $C_1$-$C_6$ alkyl;
  $R^{18}$ is selected from $C_1$-$C_6$ alkyl, fluoro $C_1$-$C_6$ alkyl, aryl, and heteroaryl, each of which is optionally substituted;
  each $X^2$ is independently selected from O, S and $NR^{15}$;
  $X^3$ is selected from O and S;
$R^3$ and $R^4$ are independently a $C_1$-$C_6$ alkyl;
$R^5$ is selected from —$(CR^9R^{10})_n$—$R^{11}$ and —$(CR^{12}$=$CR^{13})_n$—$R^{14}$;
  $R^9$ and $R^{10}$ are independently selected from hydrogen and $C_1$-$C_6$ alkyl; or alternatively $R^9$ and $R^{10}$, together with the carbon to which they are attached, form a $C_3$-$C_6$ cycloalkyl;
$R^{11}$ and $R^{14}$ are independently selected from $C_1$-$C_6$ alkyl, $C_3$-$C_6$ cycloalkyl, aryl, and heteroaryl, each of which is optionally substituted;
$R^{12}$ and $R^{13}$ are independently selected from hydrogen, halogen, and $C_1$-$C_6$ alkyl;
$X^1$ is selected from O, $NR^{15}$, and S; and
n and m are independently selected from 0 and an integer of 1-3,
provided that when "a" is a double bond, $R^1$ is heterocycloalkyl, which is optionally substituted;
or a pharmaceutically acceptable salt thereof.

(2) The compound of embodiment (1), wherein $X^1$ is O, or a pharmaceutically acceptable salt thereof.

(3) The compound of embodiment (1) or embodiment (2), wherein $R^2$ is —OC(O)CH$_2$OH or —NHC(O)CH$_2$OH, or a pharmaceutically acceptable salt thereof.

(4) The compound of any one of embodiments (1)-(3), wherein $R^3$ is methyl, or a pharmaceutically acceptable salt thereof.

(5) The compound of any one of embodiments (1)-(4), wherein $R^4$ is methyl, or a pharmaceutically acceptable salt thereof.

(6) The compound of any one of embodiments (1)-(5), wherein $R^5$ is —$(CR^{12}$=$CR^{13})_n$—$R^{14}$, $R^{12}$ and $R^{13}$ are each hydrogen or $C_1$-$C_6$ alkyl, $R^{14}$ is $C_3$-$C_6$ cycloalkyl or phenyl, and n is 1-3, or a pharmaceutically acceptable salt thereof.

(7) The compound of any one of embodiments (1)-(6), wherein "a" is a double bond and $R^1$ is heterocycloalkyl, which is optionally substituted, or a pharmaceutically acceptable salt thereof.

(8) The compound of embodiment (7), wherein the heterocycloalkyl is aziridinyl, oxiranyl, thiazolinyl, imidazolidinyl, piperazinyl, homopiperazinyl, pyrrolinyl, pyrrolidinyl, tetrahydrofuranyl, tetrahydrothiofuranyl, pyranyl, tetrahydropyranyl, piperidinyl, morpholinyl, or thiomorpholinyl, each of the foregoing is optionally substituted, or a pharmaceutically acceptable salt thereof.

(9) The compound of embodiment (8), wherein the heterocycloalkyl is piperidinyl of the formula

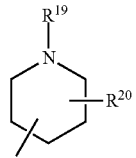

wherein
$R^{19}$ is hydrogen, $C_1$-$C_6$ alkyl or $C_1$-$C_6$ alkylcarbonyl, each of which, other than hydrogen, is optionally substituted; and
$R^{20}$ is hydrogen, halo, $C_1$-$C_6$ alkyl, $C_1$-$C_6$ alkenyl, $C_1$-$C_6$ alkynyl, hydroxy, nitro, cyano, amino, $C_1$-$C_6$ alkylamino, $C_1$-$C_6$ alkoxy, aryloxy, $C_1$-$C_6$ aralkoxy, carboxyl, carboxy-$C_1$-$C_6$ alkyl, carboxy-$C_1$-$C_6$ alkyloxy, amido, $C_1$-$C_6$ alkylamido, halo-$C_1$-$C_6$ alkylamido, aryl, heteroaryl, or heterocycloalkyl, or a pharmaceutically acceptable salt thereof.

(10) The compound of embodiment (9) that is selected from the group consisting of

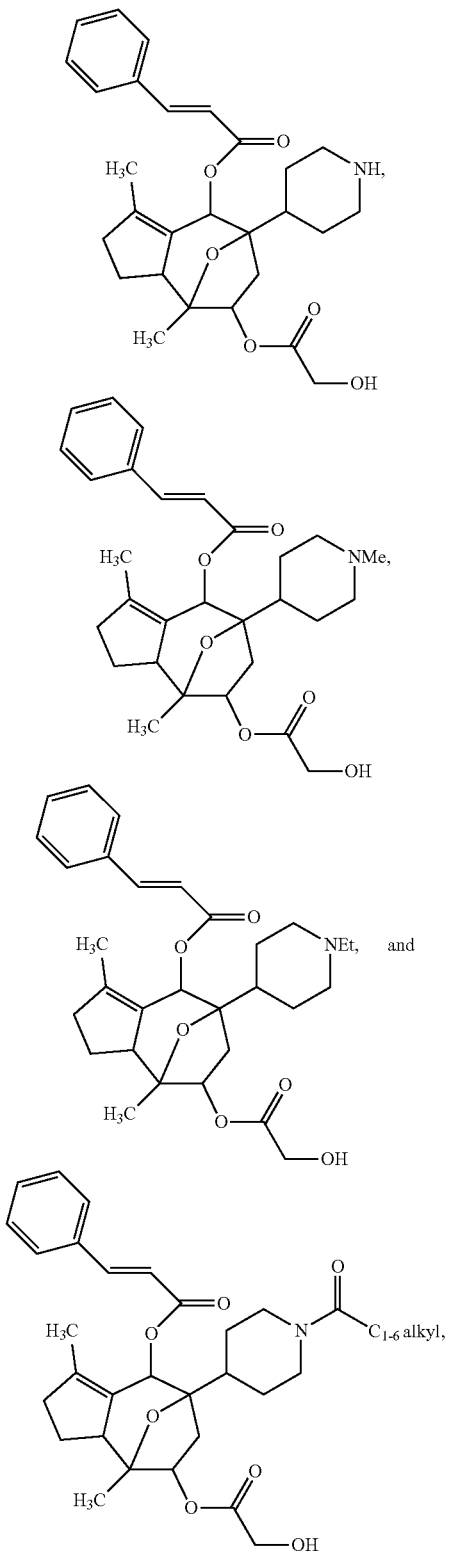

or a pharmaceutically acceptable salt thereof.

(11) The compound of any one of embodiments (1)-(6), wherein "a" is a single bond, or a pharmaceutically acceptable salt thereof.

(12) The compound of embodiment (11), wherein $R^1$ is $C_3$-$C_6$ cycloalkyl or phenyl, or a pharmaceutically acceptable salt thereof.

(13) The compound of embodiment (12) that is selected from the group consisting of

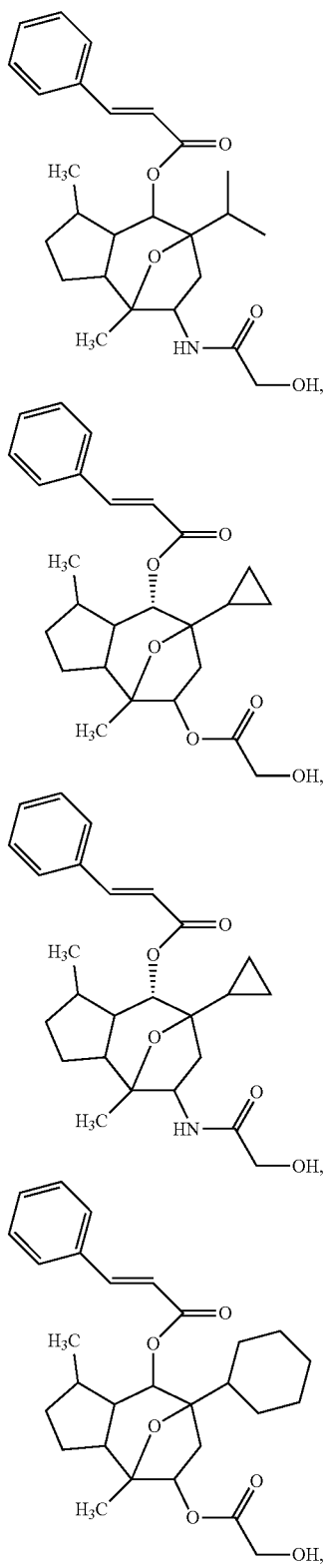

27
-continued

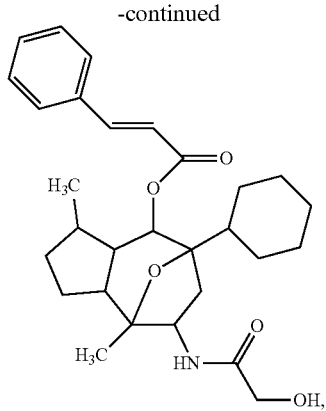

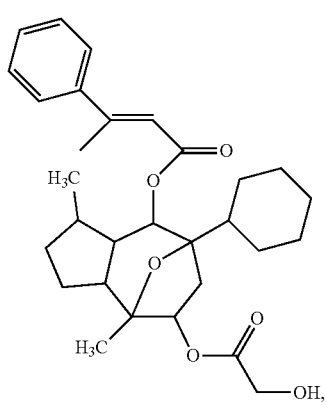

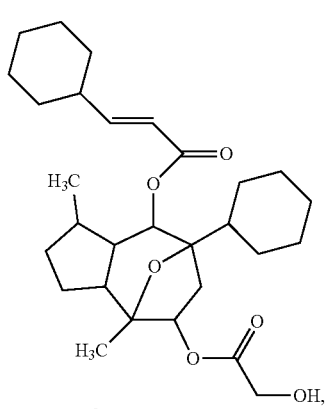

28
-continued

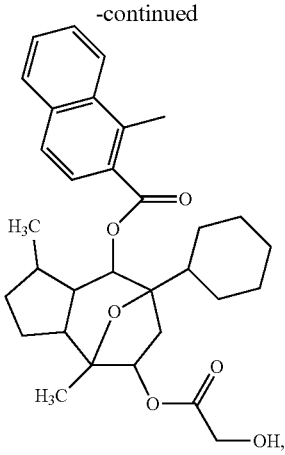

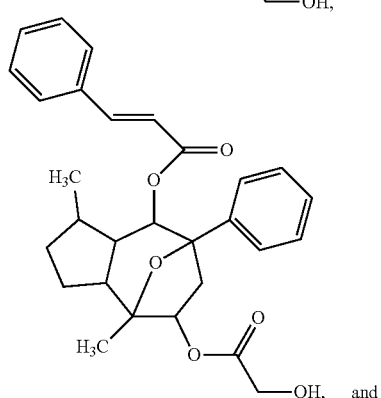

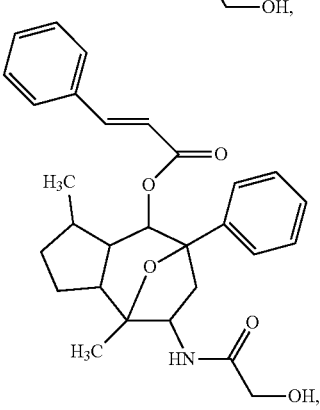

or a pharmaceutically acceptable salt thereof.

(14) A pharmaceutical composition comprising a pharmaceutically acceptable carrier and the compound or a pharmaceutically acceptable salt thereof of any one of embodiments (1)-(13).

(15) A method of treating cancer in a subject comprising administering to the subject an effective amount of the compound of any one of embodiments (1)-(13) or a pharmaceutically acceptable salt thereof.

(16) The method of embodiment (15), wherein the cancer is leukemia, non-small cell lung cancer, colon cancer, melanoma, prostate cancer, renal cancer, bladder cancer, breast cancer, central nervous system (CNS) cancer, ovarian cancer, or Ewing's sarcoma.

(17) The method according to embodiment (16), wherein the cancer is renal cancer.

(18) The method according to embodiment (16), wherein the cancer is prostate cancer.

(19) The method according to embodiment (16), wherein the cancer is Ewing's sarcoma.

(20) The method according to embodiment (16), wherein the cancer is bladder cancer.

(21) The method according to embodiment (16), wherein the cancer is breast cancer.

(22) The method of any one of embodiments 15-21, which is free or substantially free of activation of a transient receptor potential channel 4 (TRPC4) receptor in the subject.

The following examples further illustrate the invention but, of course, should not be construed as in any way limiting its scope.

EXAMPLES

All reactions were carried out under argon unless otherwise specified. Solvents were dried using standard procedures.

Example 1

The compounds of the invention can be prepared following the general synthetic scheme shown in FIG. 1. The reagents and conditions for the chemical scheme of FIG. 1 are as follows: a) L-(+)-diethyl tartrate, Ti(OiPr)$_4$, tert-butylhydroperoxide, CH$_2$Cl$_2$, −40° C., 4 h, 9:1 e.r.; b) CCl$_4$, PPh$_3$, 80° C., 6 h; c) nBuLi (3.5 equiv), THF, −40° C., 2 h; d) TESOTf, Et$_3$N, CH$_2$Cl$_2$, 23° C., 3 h; e) AD-mix-α, tBuOH/H$_2$O (1:1), 23° C., 10 h; f) NaIO$_4$/SiO$_2$, CH$_2$Cl$_2$, 23° C., 10 h; g) 4 (1.6 equiv), benzene, reflux, 2 days. h) LDA, R$_1$COMe, THF, −78° C., 15 h; i) [IPrAuNCPh]SbF$_6$ (3 mol %), CH$_2$Cl$_2$, 23° C., 5 h; j) TBAF, THF, 23° C., 12 h; k) DMAP, imidazole, TBDMSCl, 23° C.; l) CrO$_3$, pyridine, CH$_2$Cl$_2$, 23° C., 1 h and CeCl$_3$(H$_2$O)$_7$, NaBH$_4$, MeOH, 23° C., 5 min; m) WCl$_6$ (2 equiv), nBuLi (4 equiv), THF, 0 to 50° C., 2 h; n) R$_5$COCl, DMAP, Et$_3$N, CH$_2$Cl$_2$, 45° C. 4-12 h and TBAF, THF, 23° C., 12 h; o) R$^2$COOH, DMAP, NEt$_3$, 2,4,6-trichlorobenzoyl chloride, toluene, 23° C., 1 h and TBAF, AcOH, THF, 4 h, 23° C.

Example 2

The following examples describe the preparation of compounds of formula (I), in which "a" is a double bond, X$_1$ is O, R$^3$ is methyl, and R$^4$ is methyl. As will become apparent to the skilled in the art person, the careful selection of the starting materials will allow for the preparation of other compounds of formula (I). See FIGS. 2 and 3.

Figure 2:
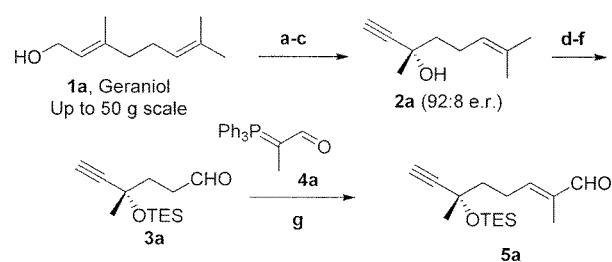
FIG. 2 is a chemical scheme of the synthesis of (S,E)-2, 6-dimethyl-6-(triethylsilyloxy)oct-2-en-7-ynal 5a via steps a-g.
Figure 3:
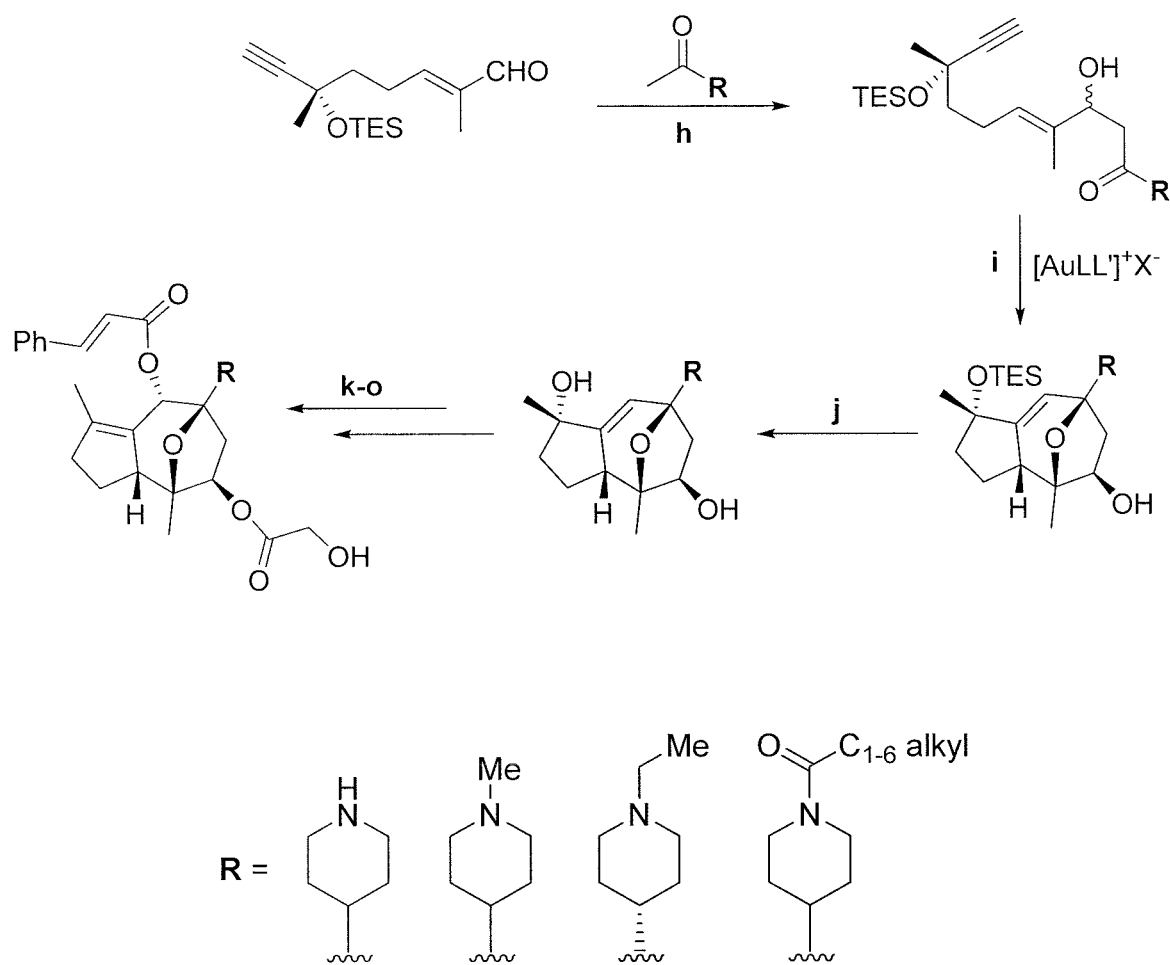
FIG. 3 is a chemical scheme of the synthesis of compounds of formula (I) starting from (S,E)-2,6-dimethyl-6-(triethylsilyloxy)oct-2-en-7-ynal via steps h-o.
Figure 4:
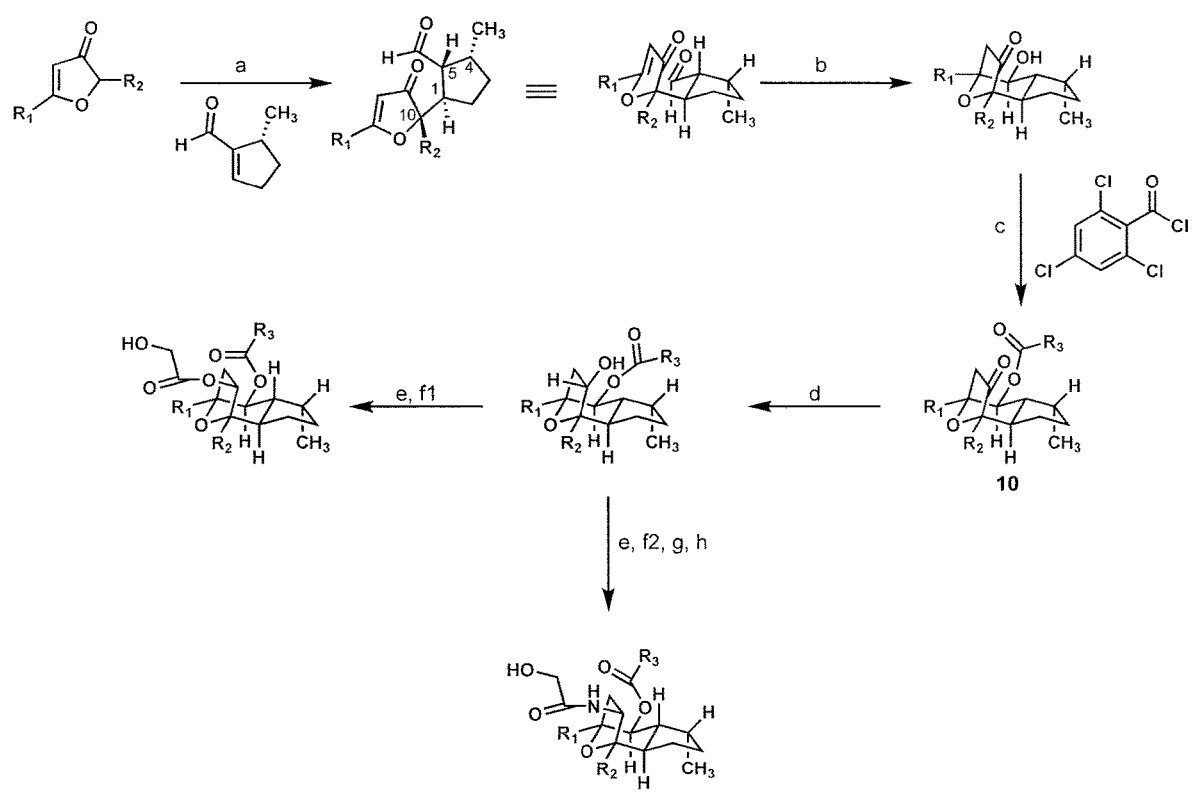
FIG. 4 is a chemical scheme of the synthesis of a compound of formula (I). Reagents and conditions: a) LDA in THF, followed by the addition of (R)-5-methylcyclopent-1-ene-1-carbaldehyde; b) $SmI_2$ and hexamethylphosphoramide (HMPA) in THF; c) carboxylic acid in DMAP and $Et_3N$; d) $NaBH_4$ in $CH_3OH$; e) lithium bis(trimethylsilyl) amide (LiHMDS), $(imid)_2SO_2$; f) either cesium hydroxyacetate, 18-crown-6 or $NaN_3$ in dimethylformamide (DMF); g) either Zn and $NH_4Cl$ or $H_2$ and Lindlar catalyst or $H_2$ and $Pd(OH)_2$; h) 1-ethyl-3-(3-dimethylaminopropyl)carbodiimide (EDC), DMAP, and glycolic acid.
Figure 5A:
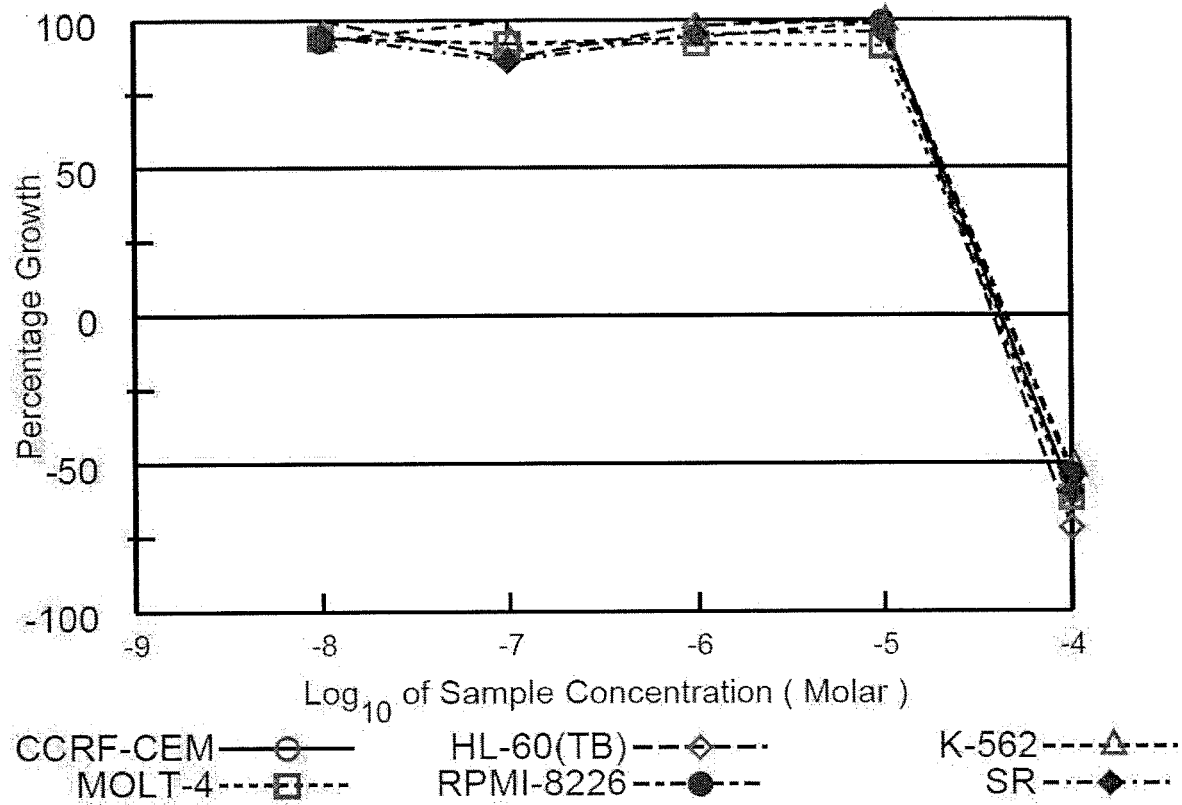
FIG. 5A-5I depict the dose response curves for a compound formula (I) (i.e., (Ia)) against various cancer cell lines in the NCI 60-cell test.
Figure 5B:
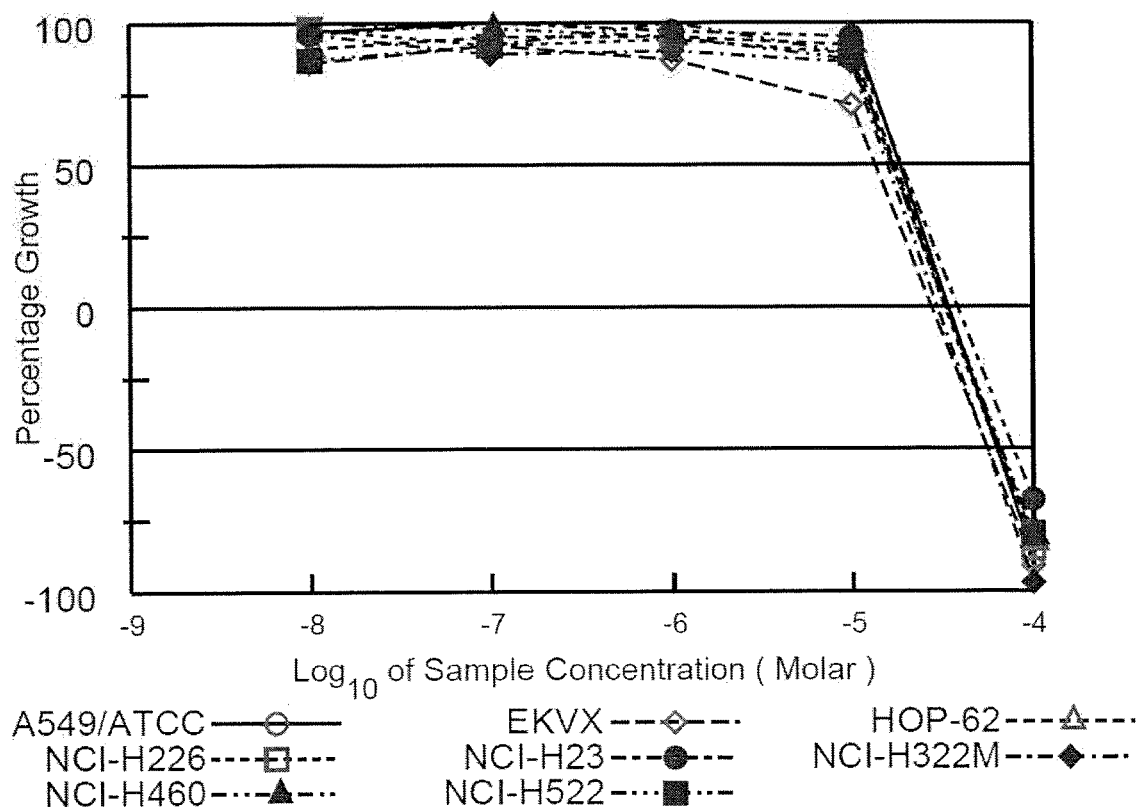
Figure 5C:
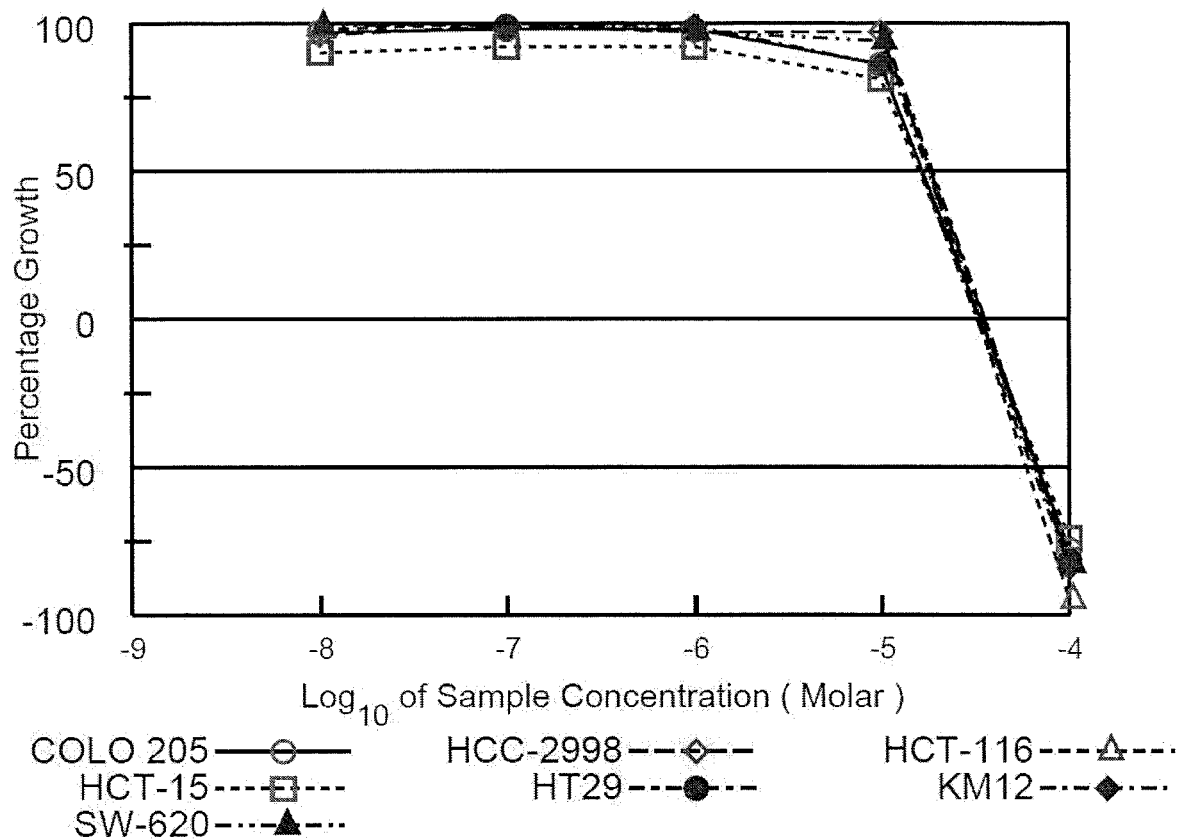
Figure 5D:
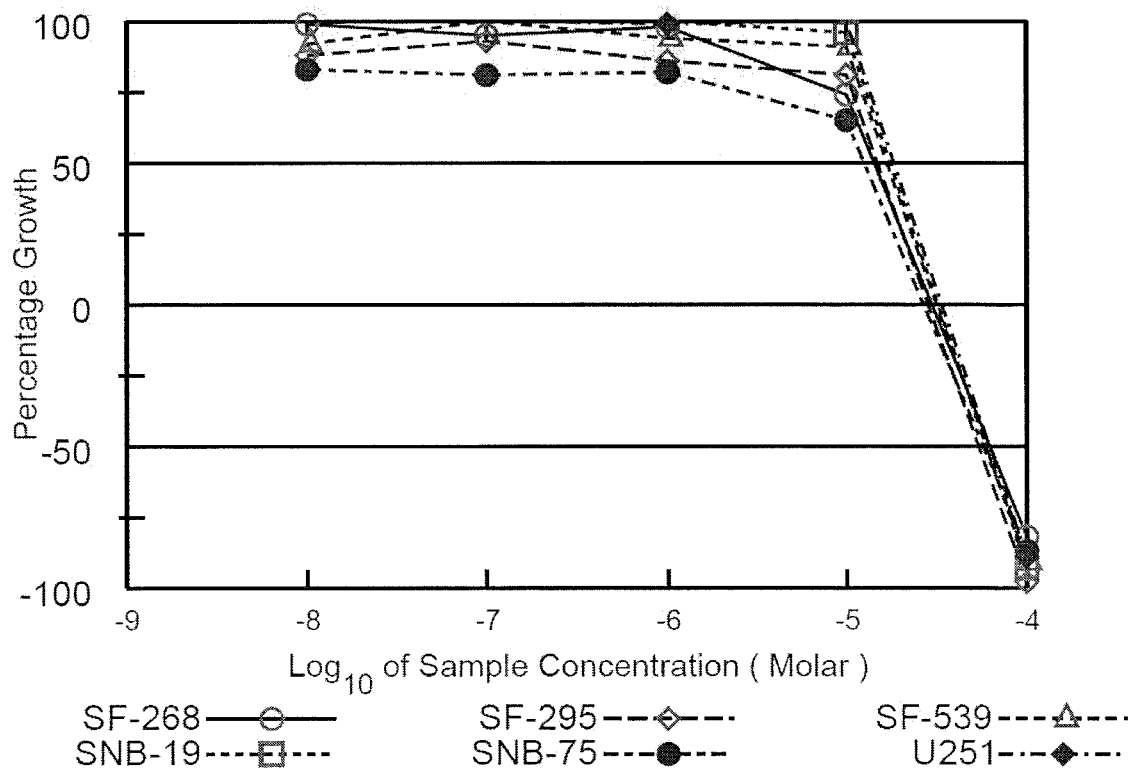
Figure 5E:
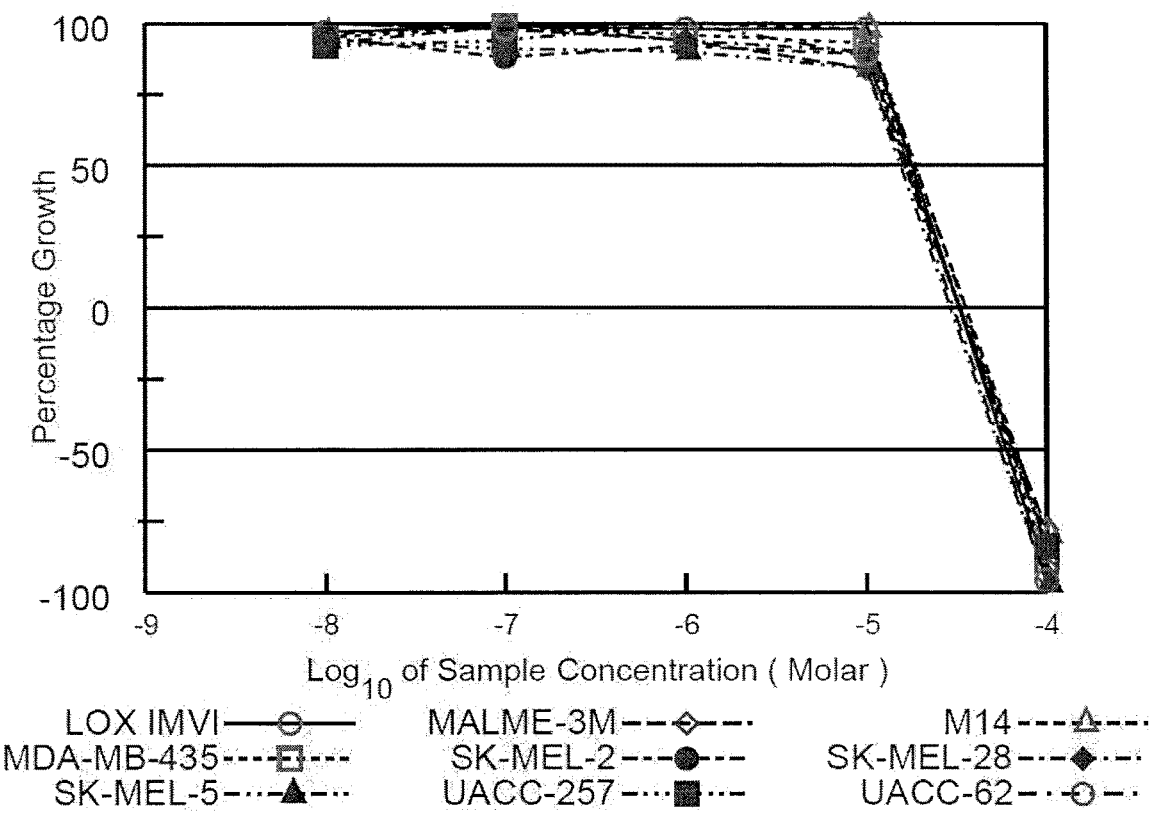
Figure 5F:
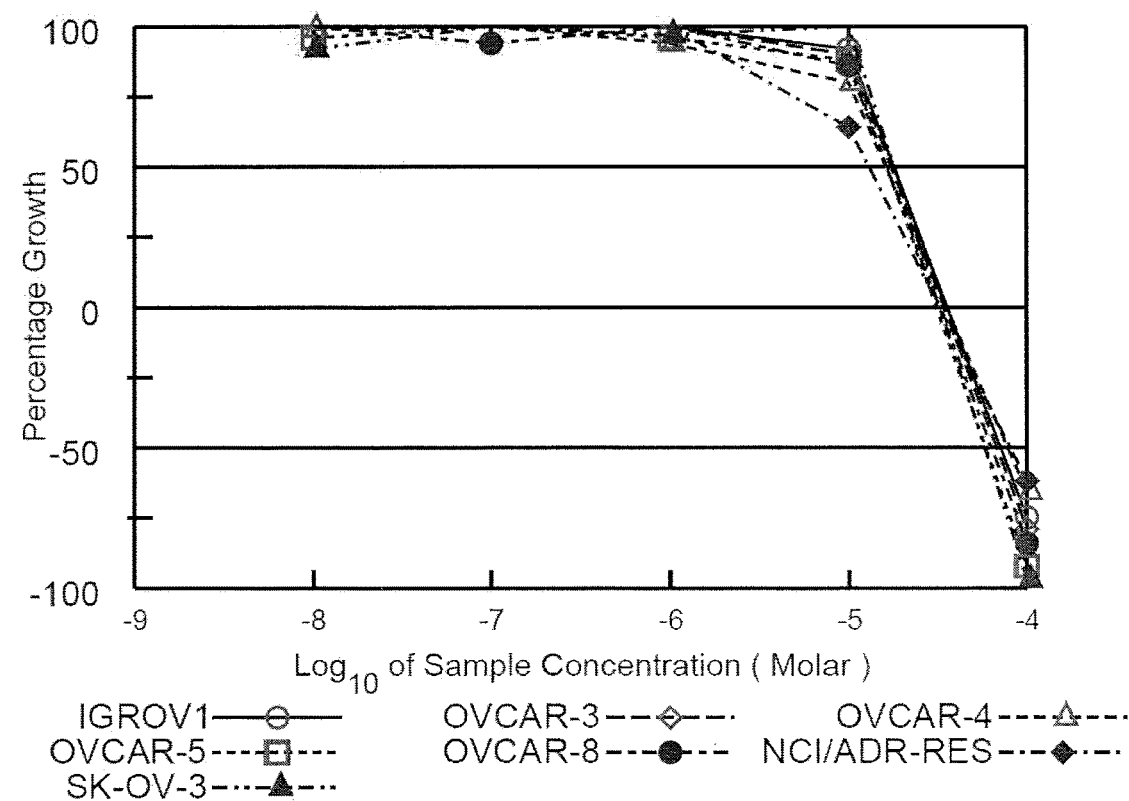
Figure 5G:
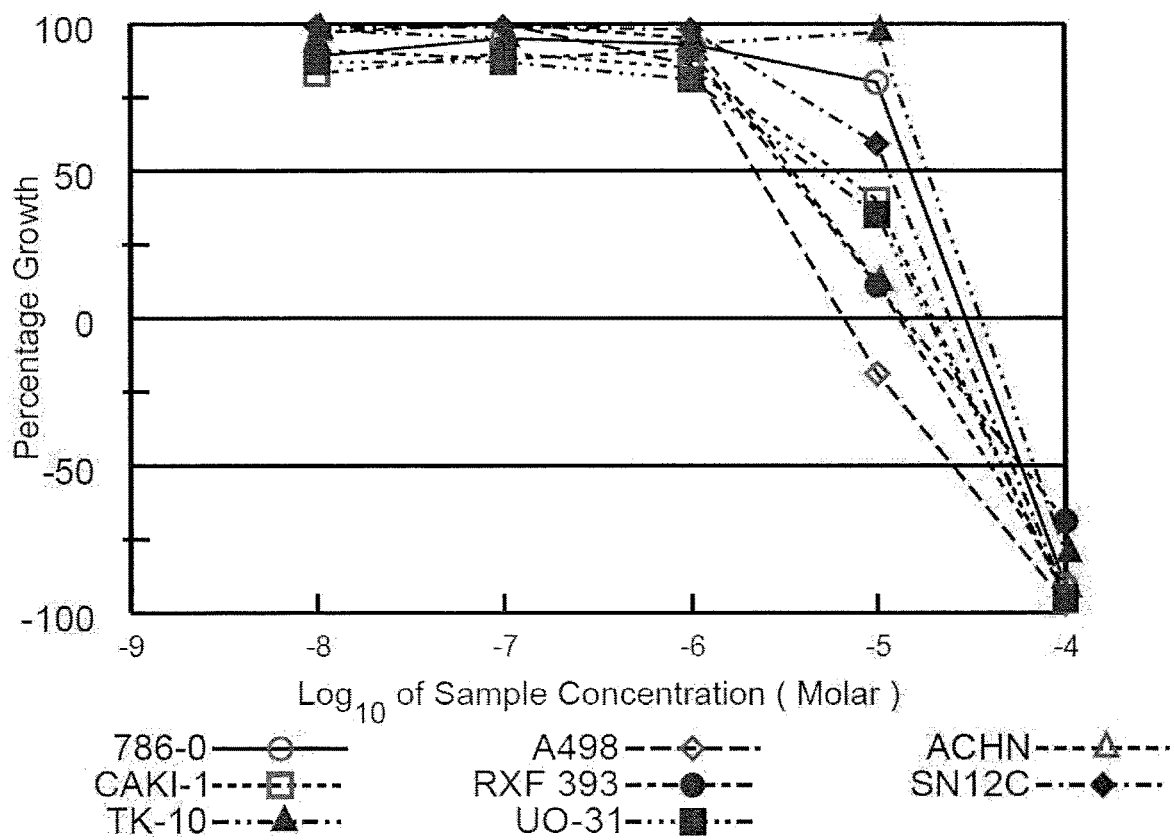
Figure 5H:
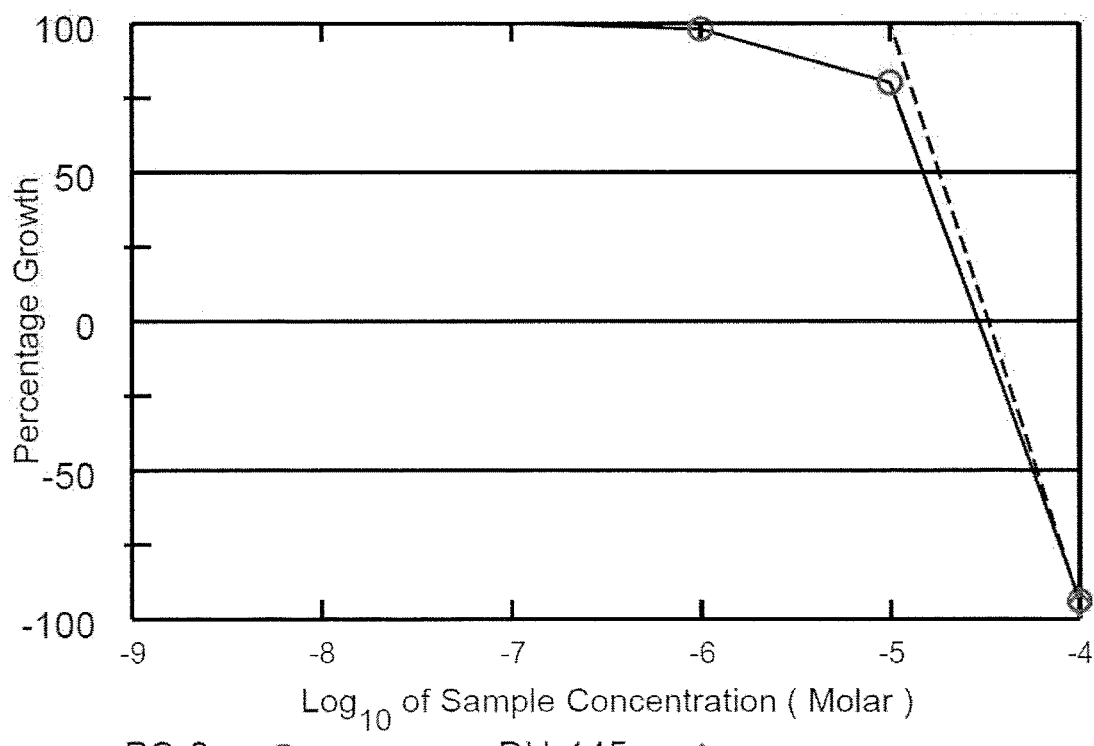
Figure 5I:
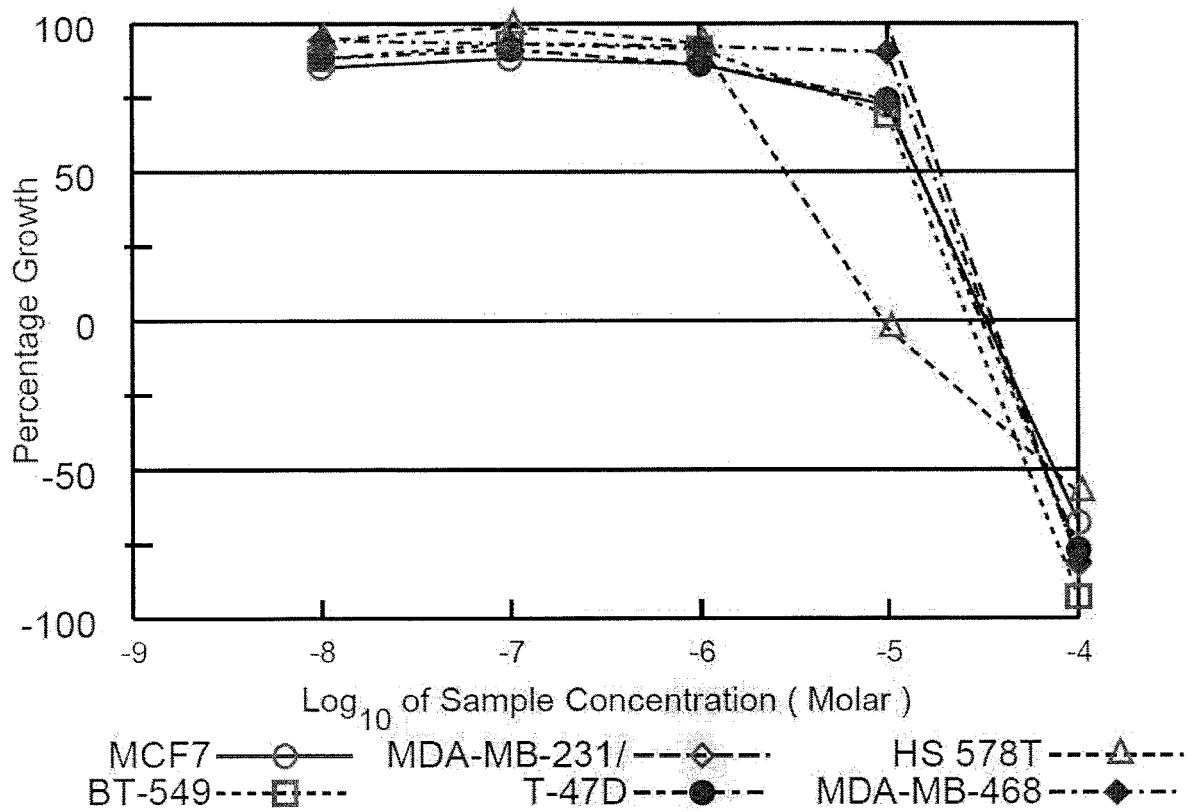
Figure 6A:
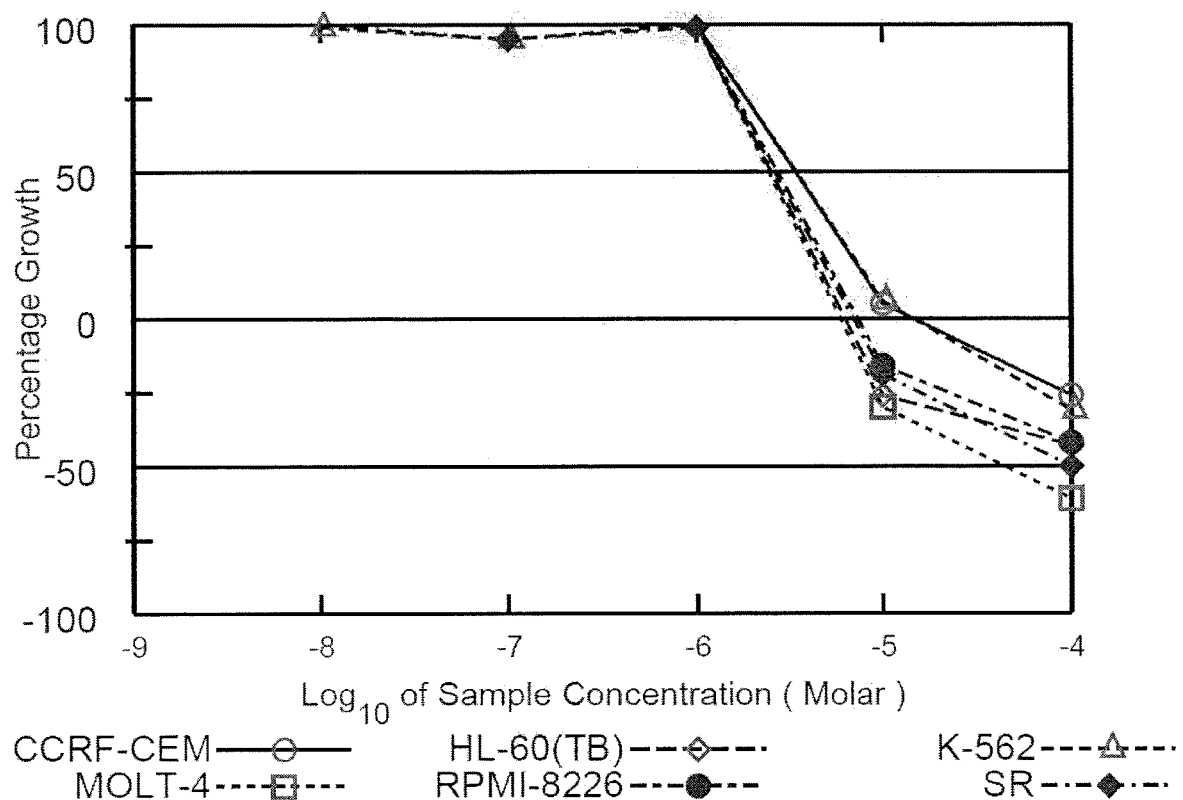
FIG. 6A-6I depict the dose response curves for a compound formula (I) (i.e., (Ib) against various cancer cell lines in the NCI 60-cell test.
Figure 6B:
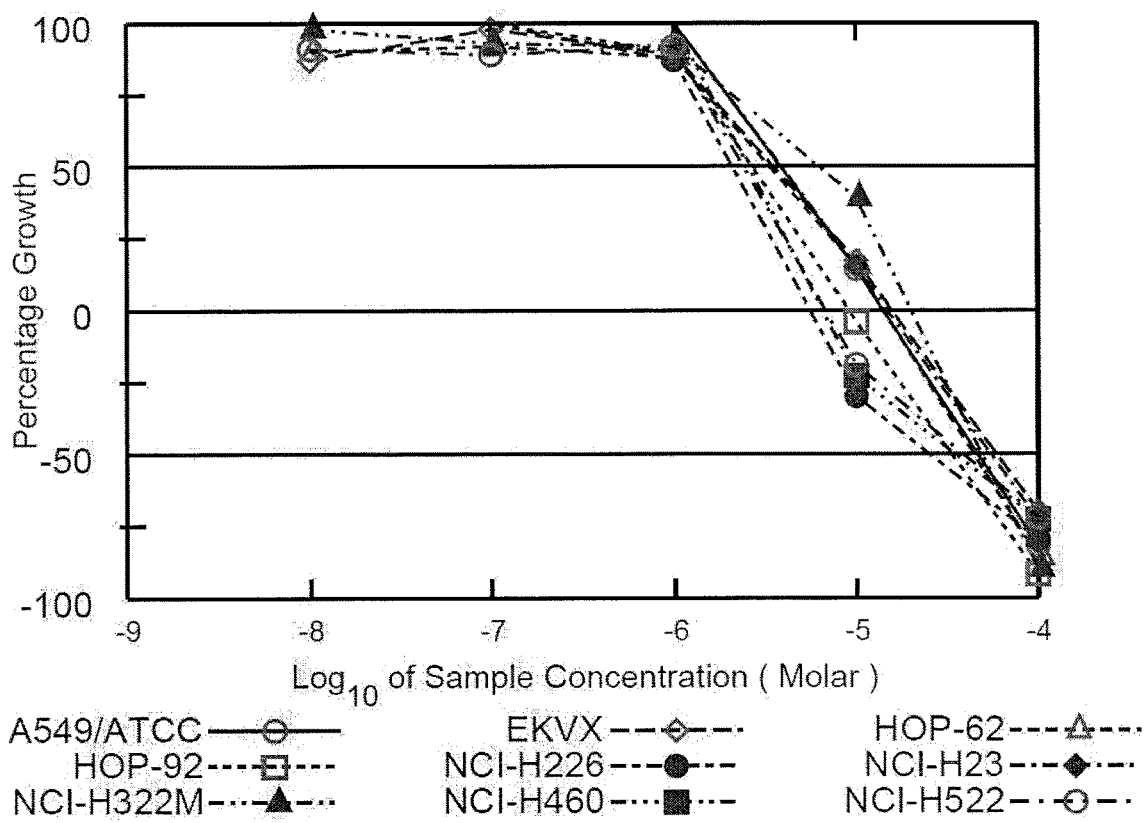
Figure 6C:
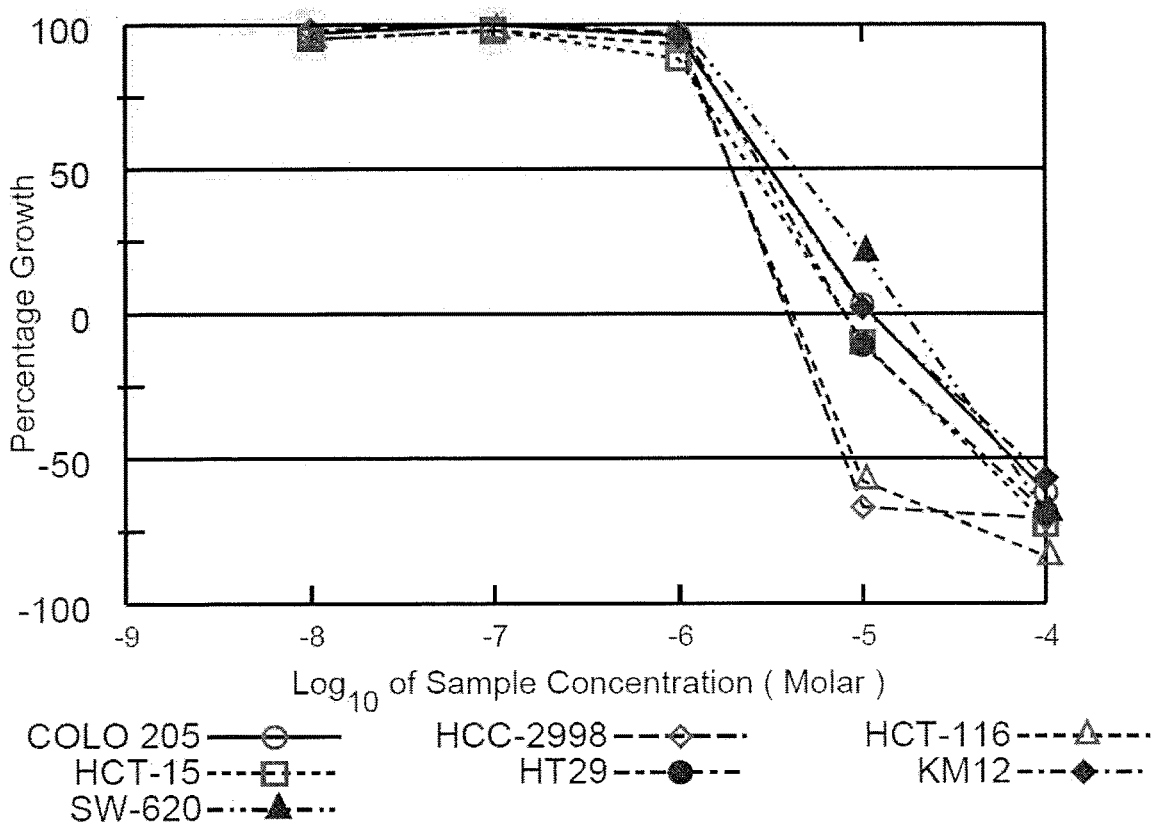
Figure 6D:
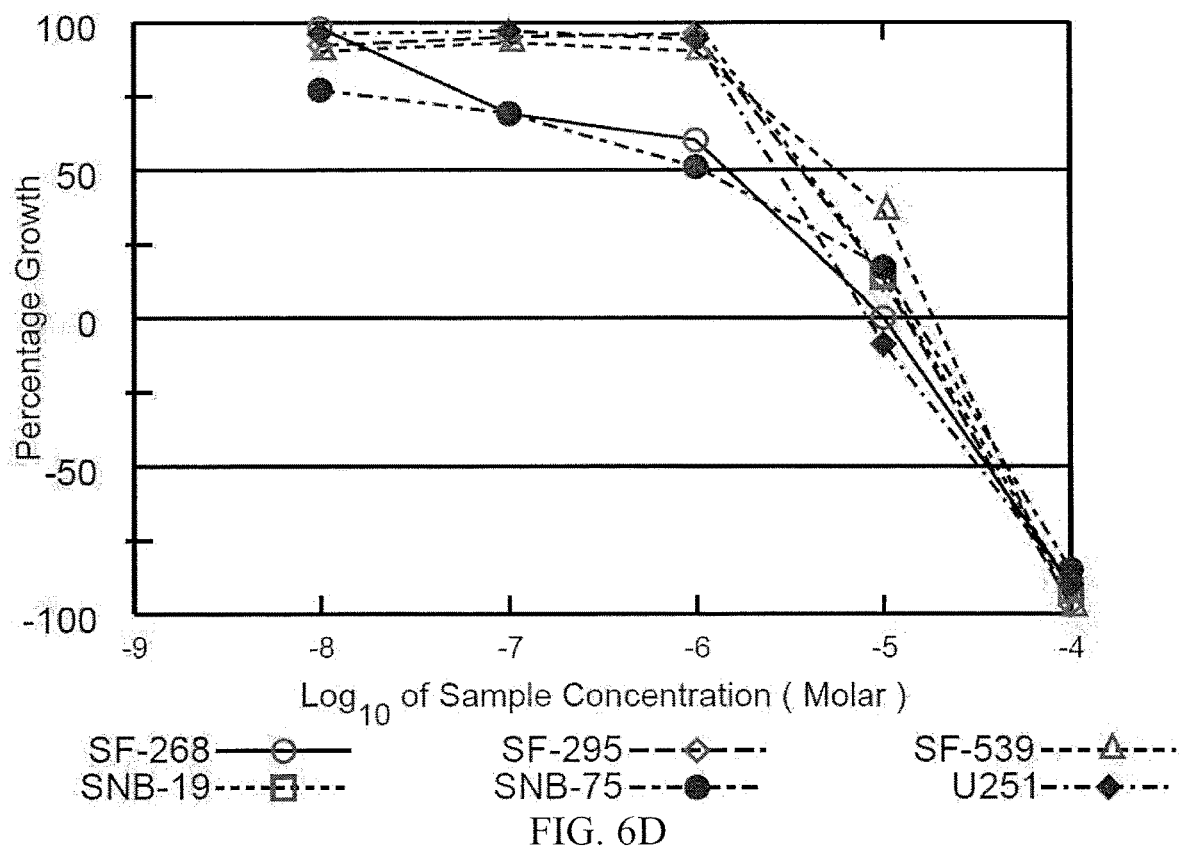
Figure 6E:
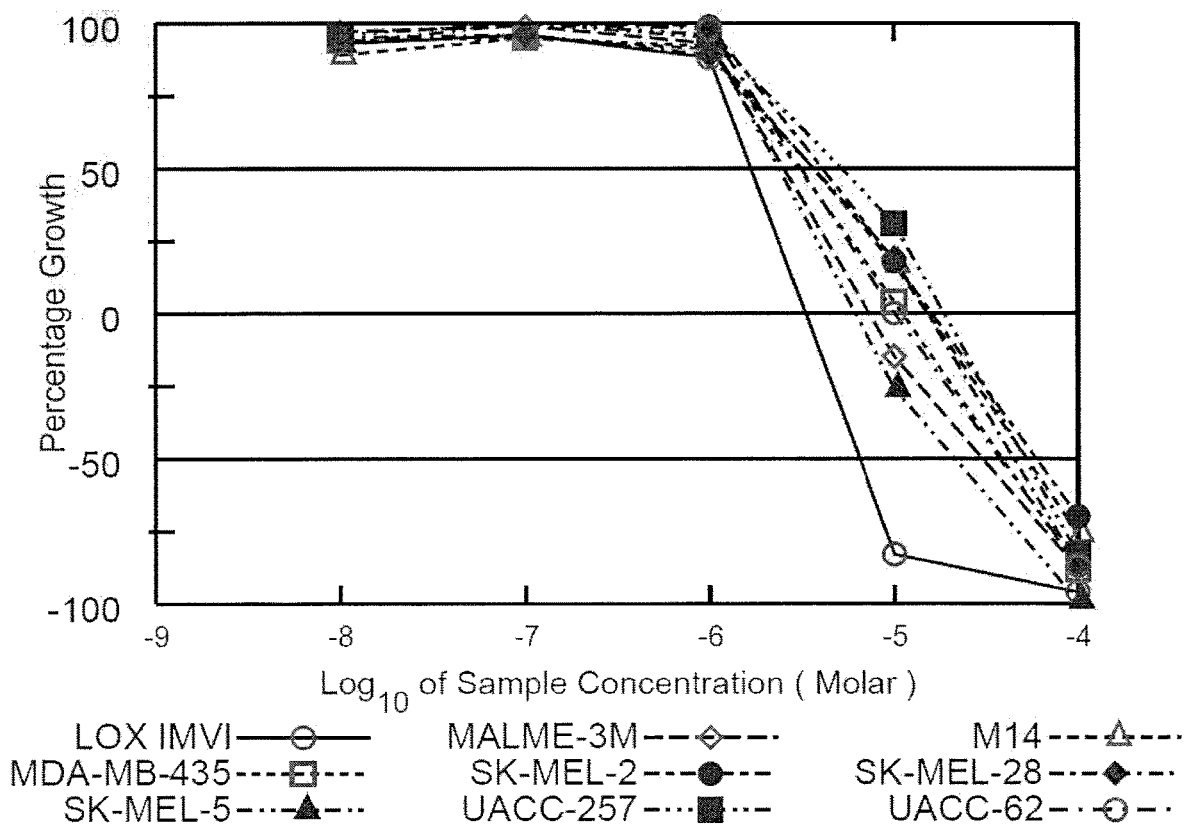
Figure 6F:
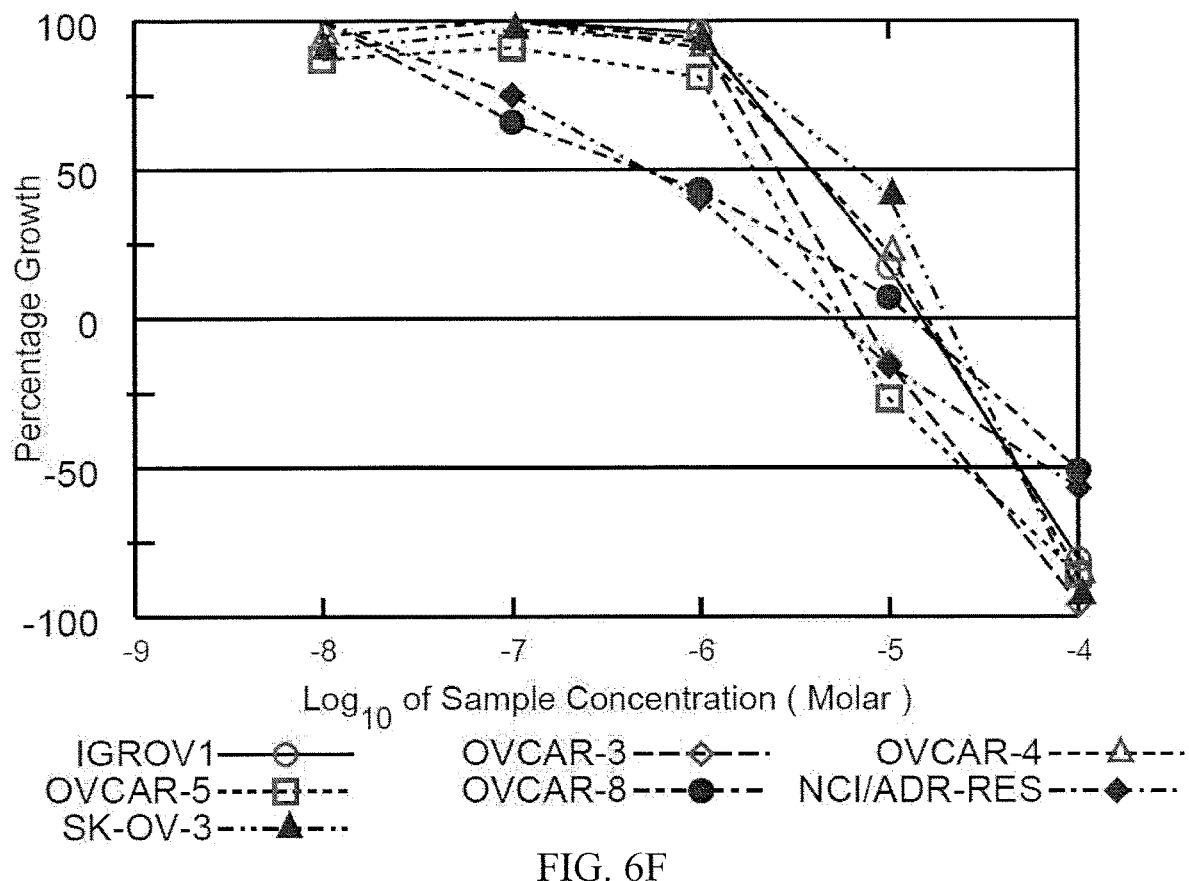
Figure 6G:
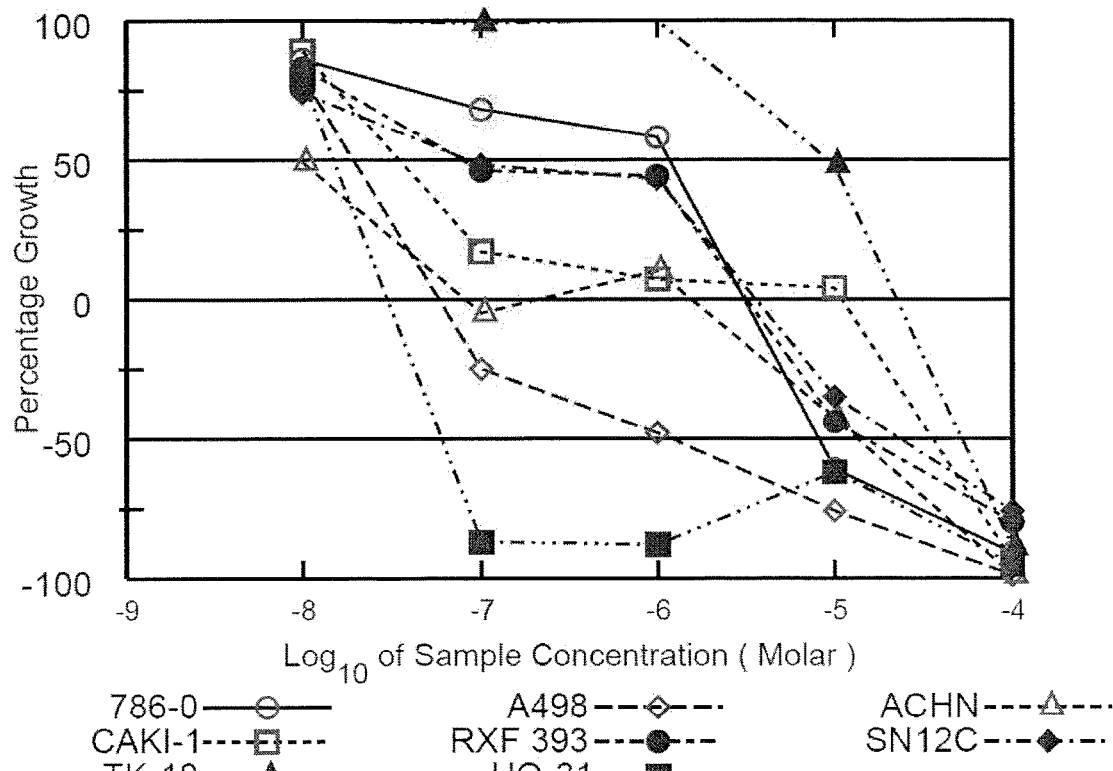
Figure 6H:
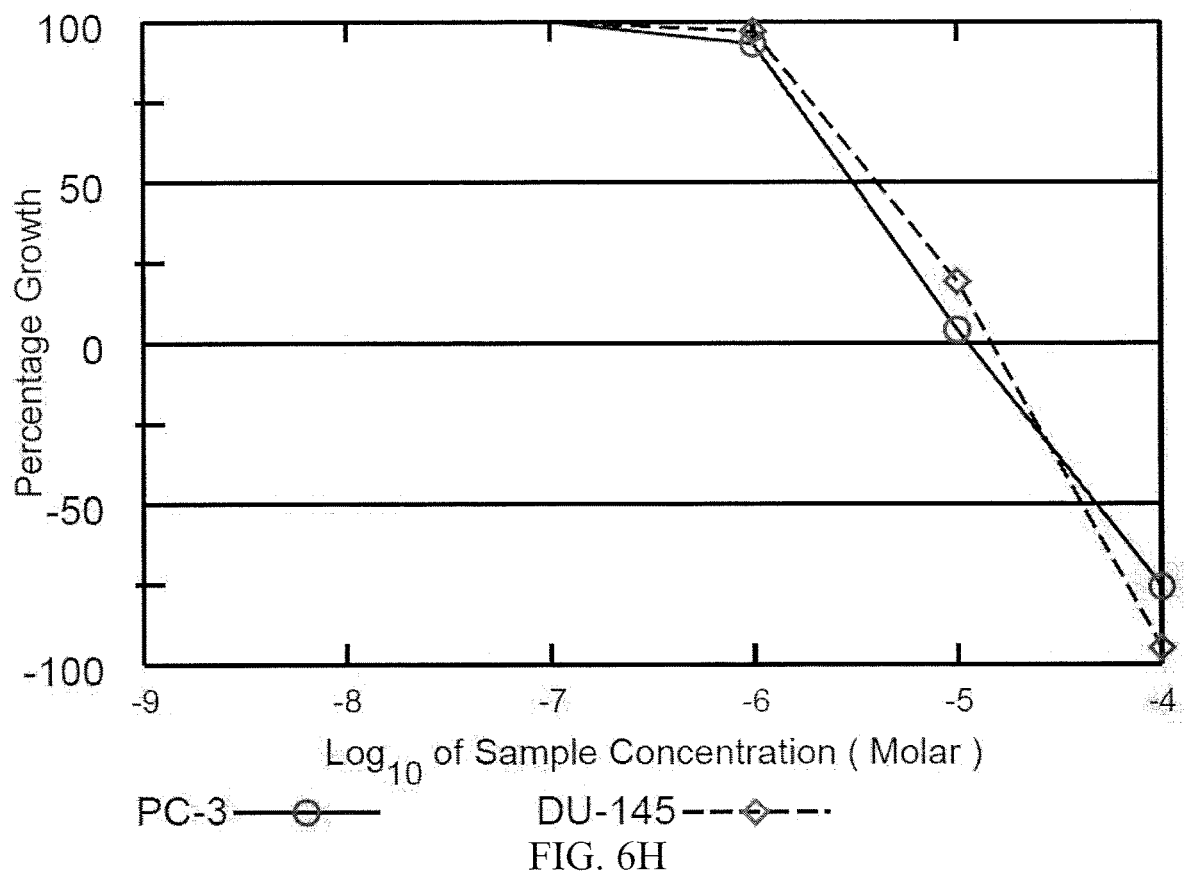
Figure 6I:
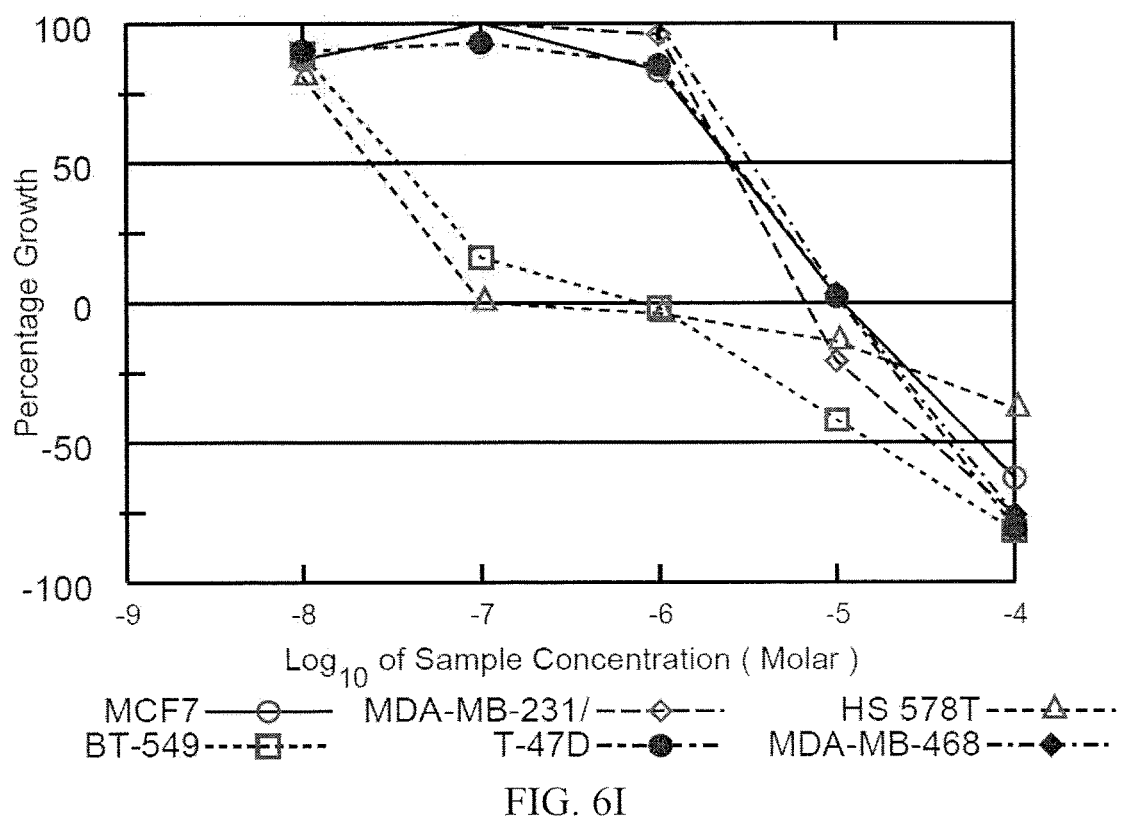
Figure 7A:
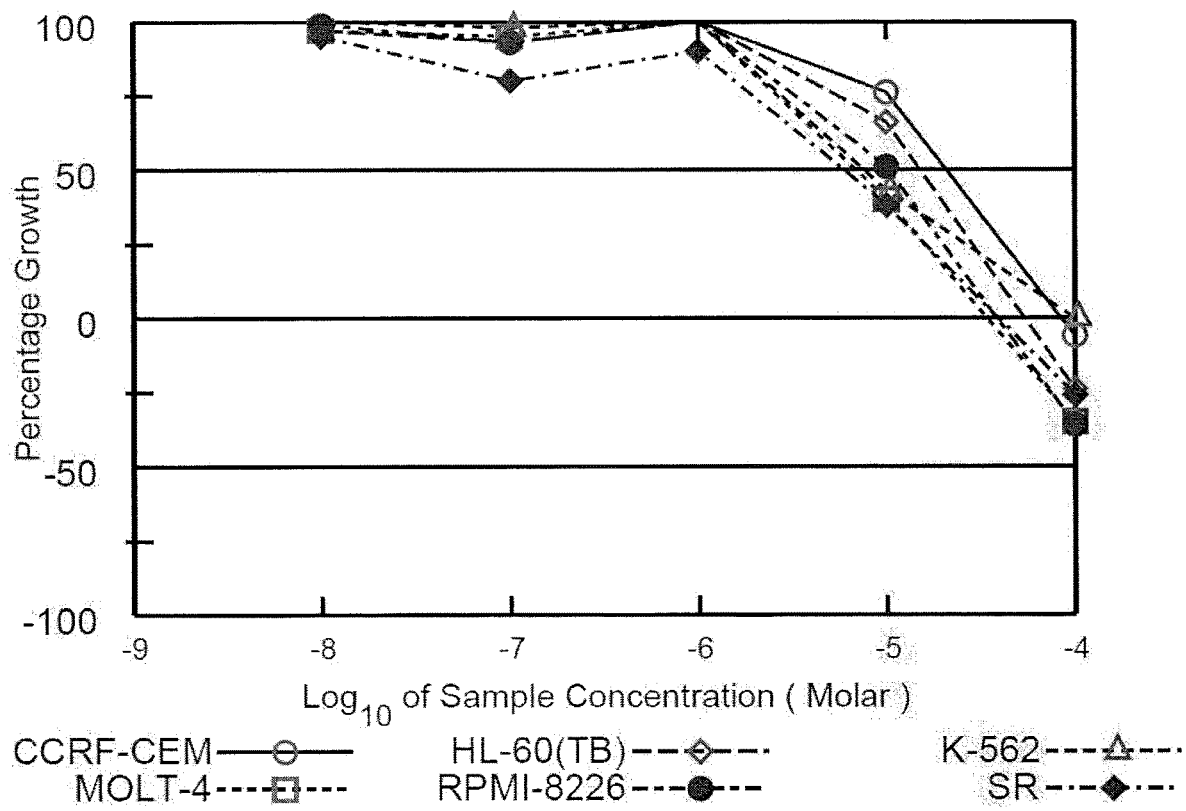
FIG. 7A-7I depict the dose response curves for a compound formula (I) (i.e., (Ic)) against various cancer cell lines in the NCI 60-cell test.
Figure 7B:
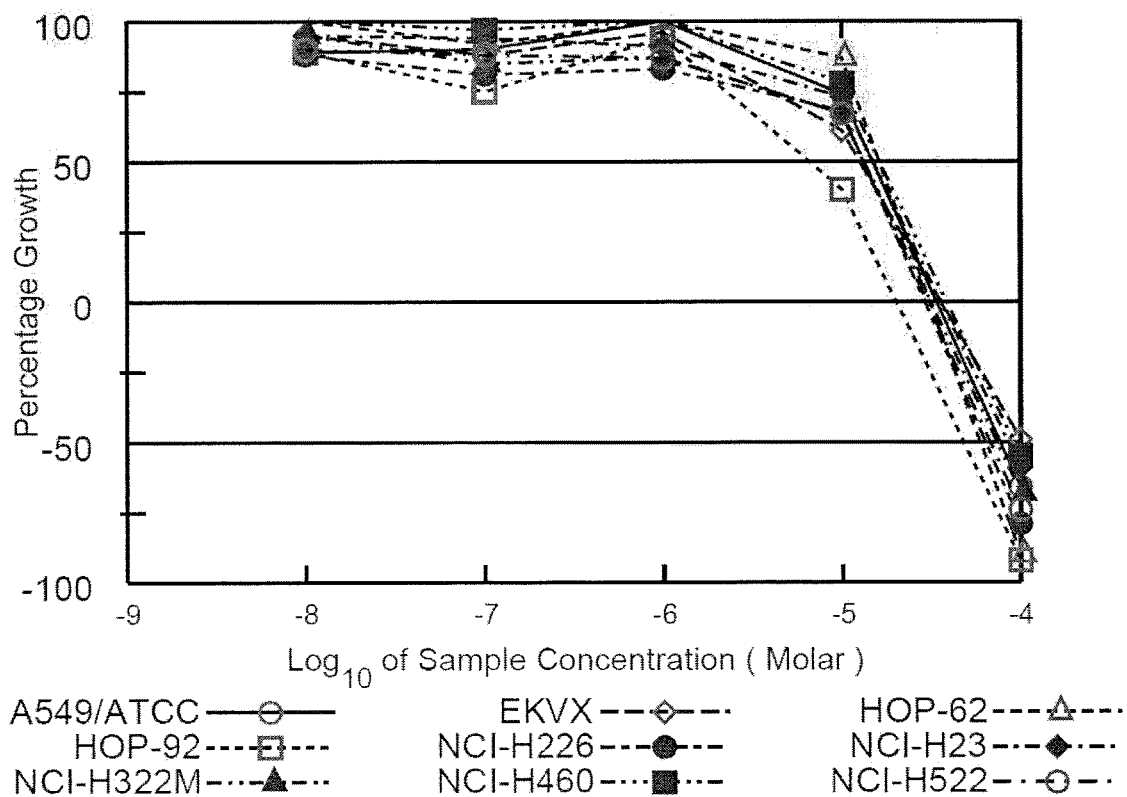
Figure 7C:
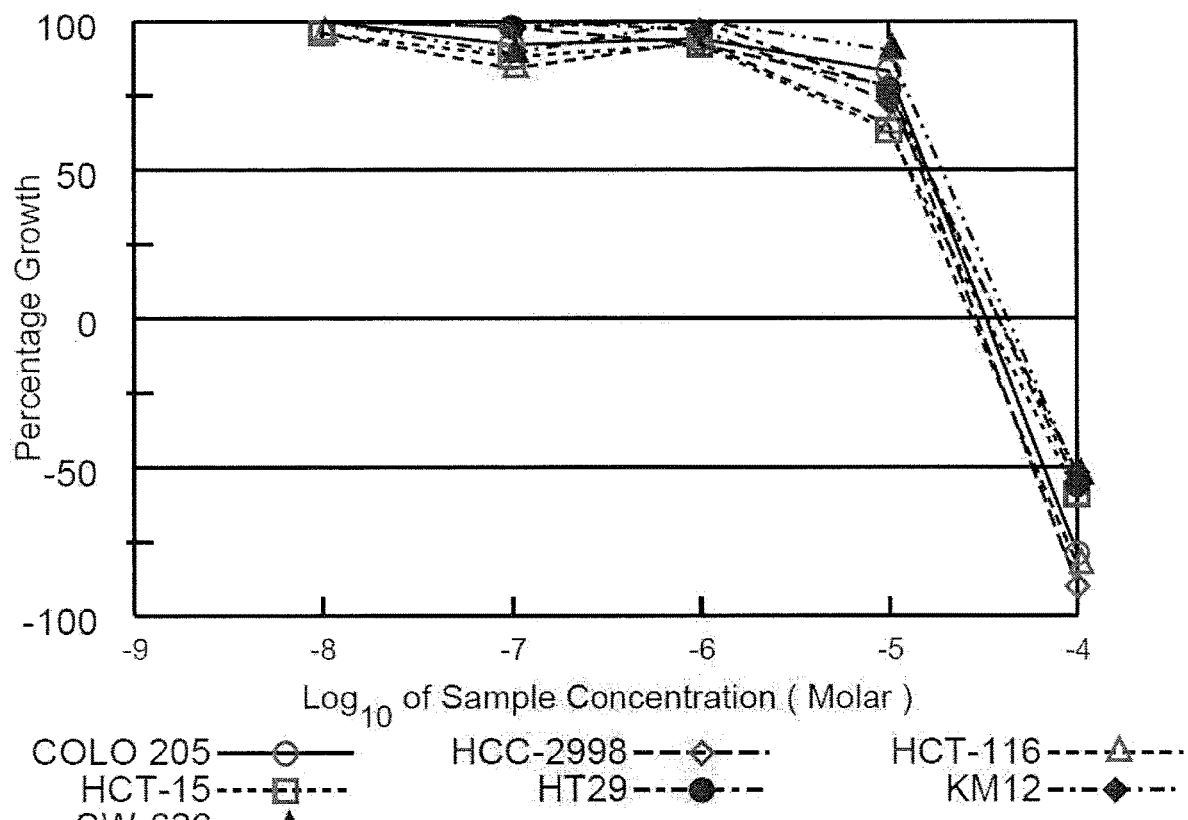
Figure 7D:
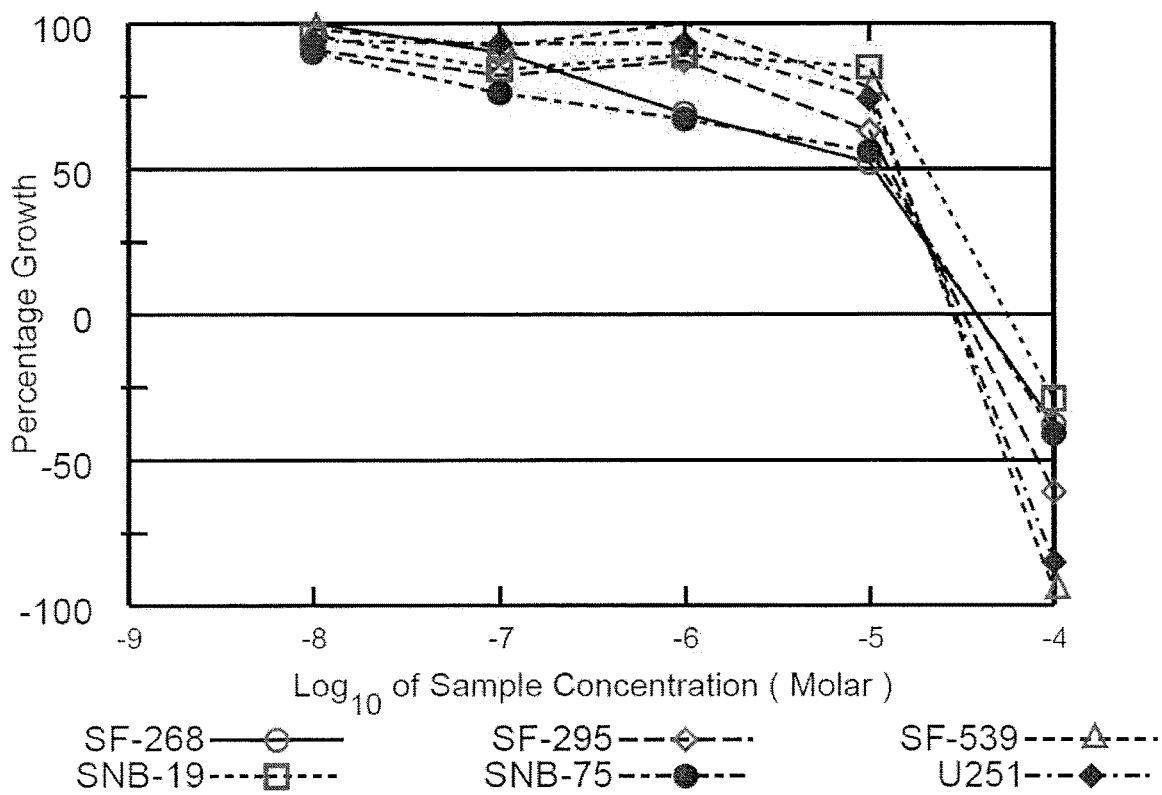
Figure 7E:
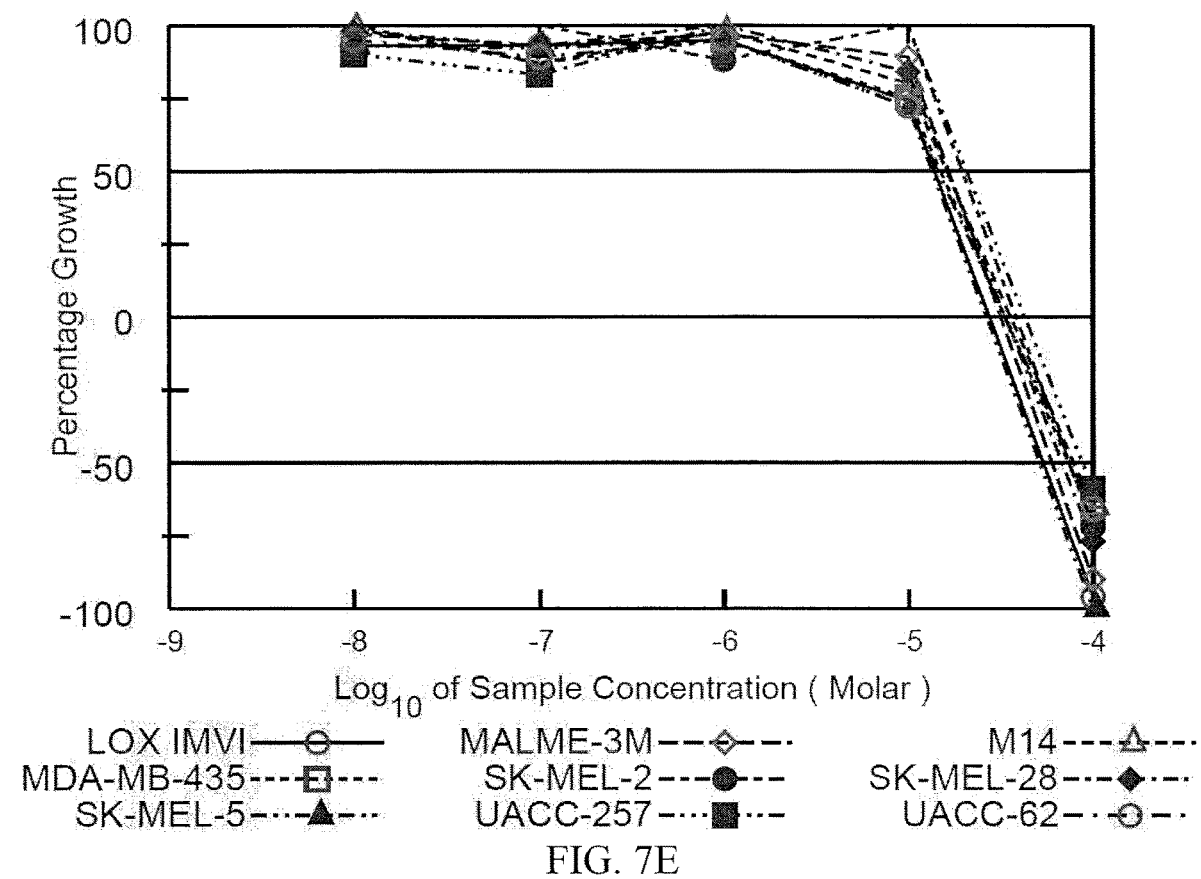
Figure 7F:
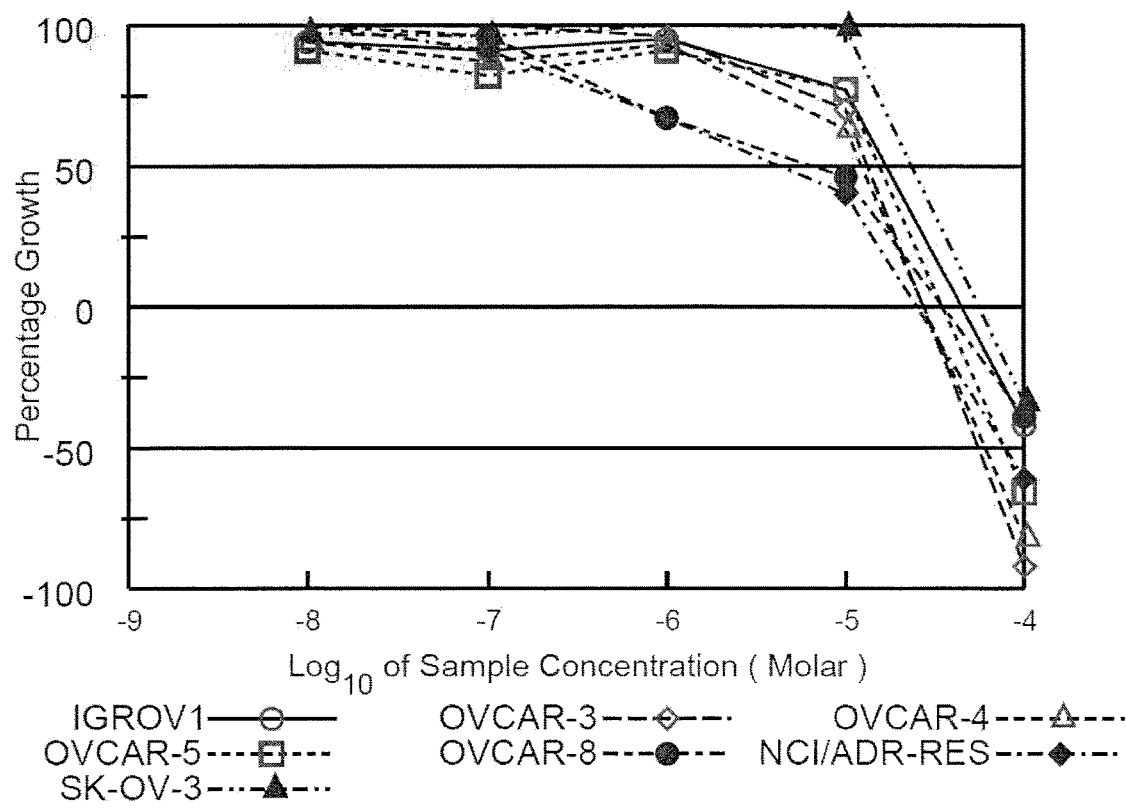
Figure 7G:
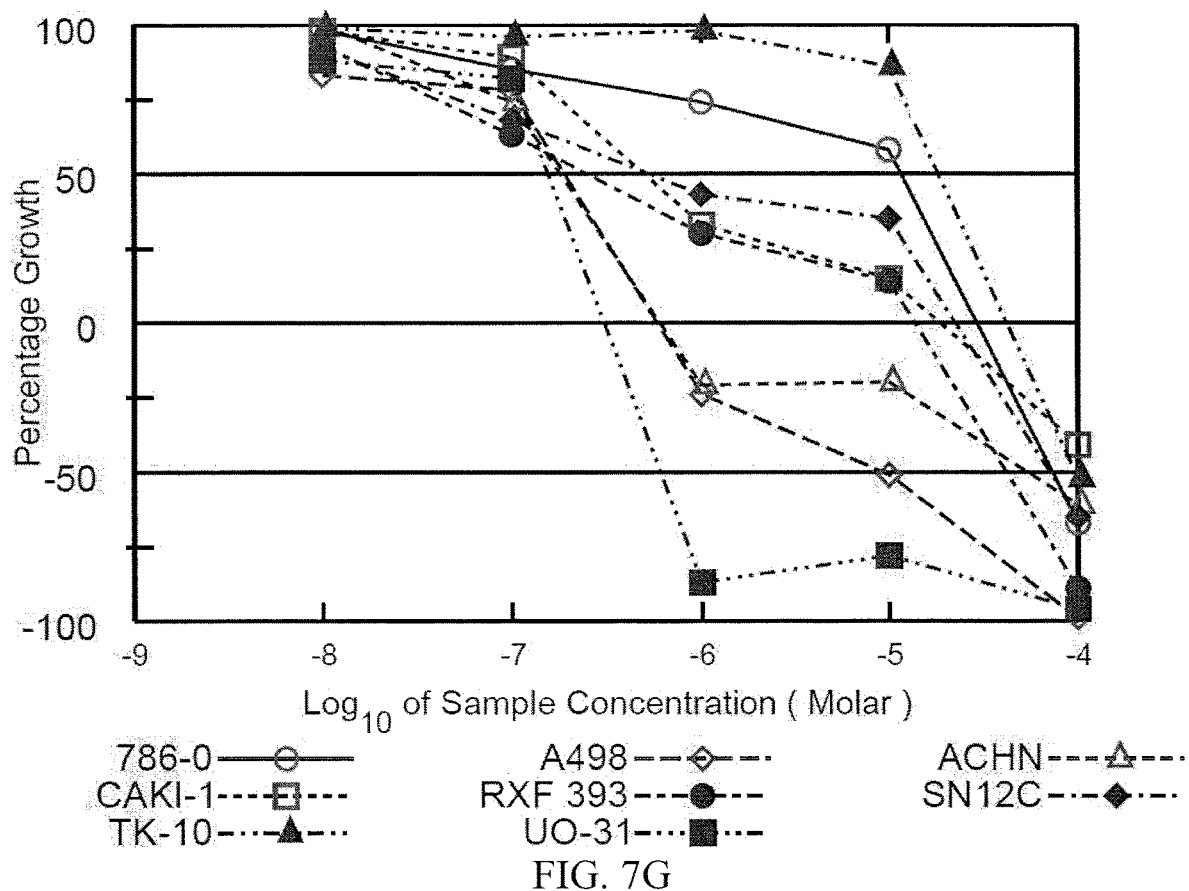
Figure 7H:
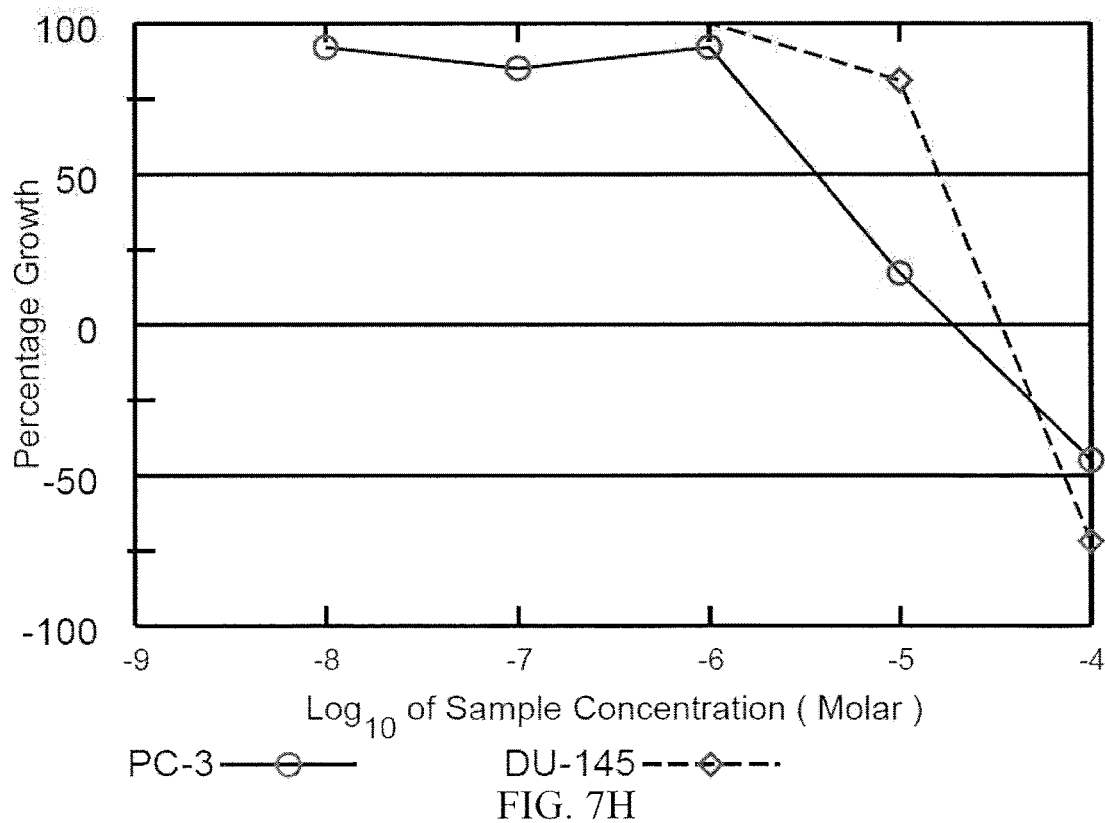
Figure 7I:
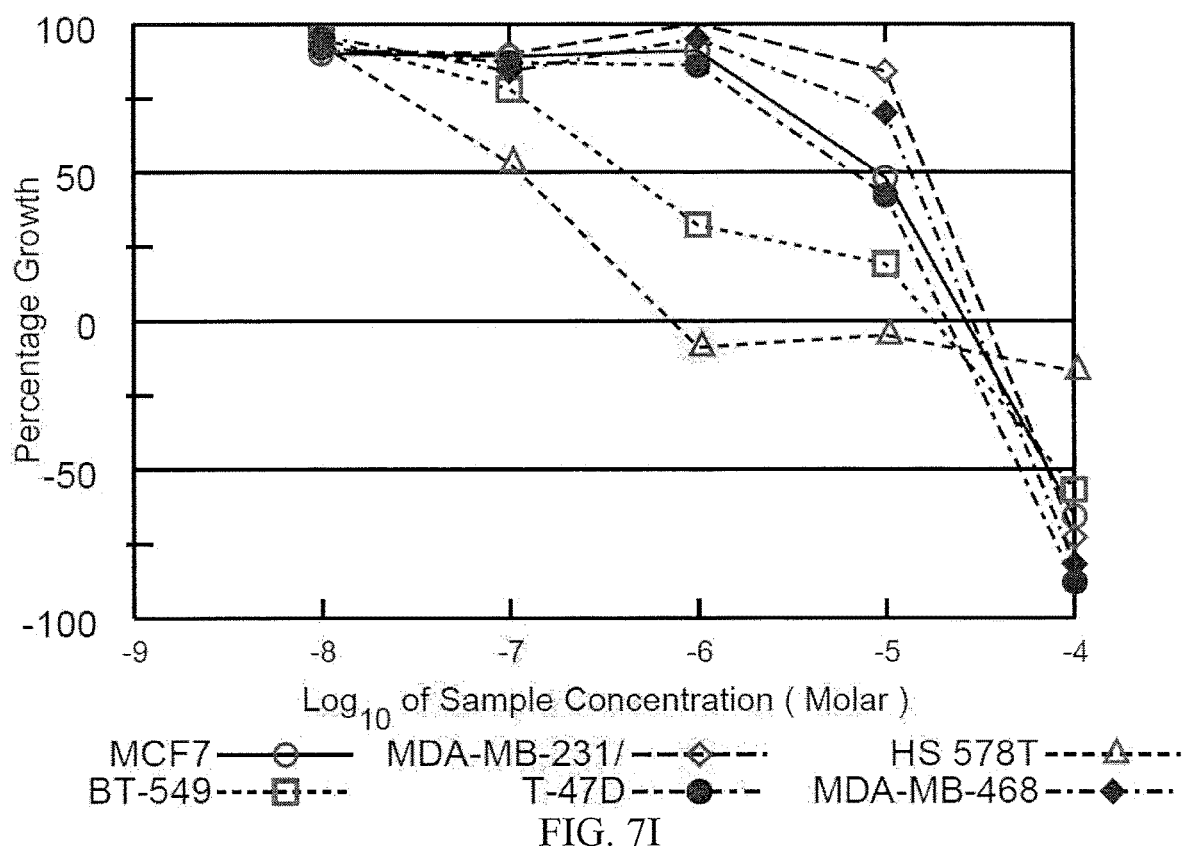
Figure 8A:
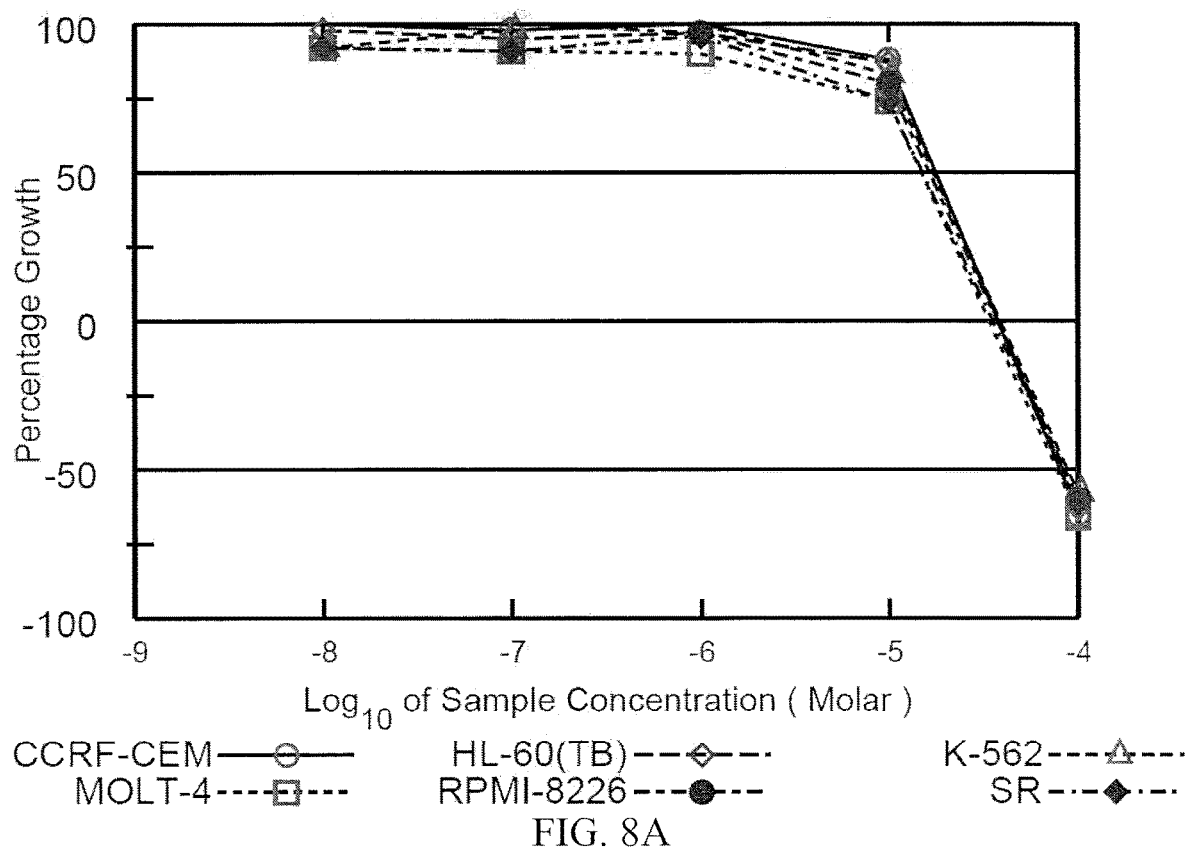
FIG. 8A-8I depict the dose response curves for a compound formula (I) (i.e., (Id)) against various cancer cell lines in the NCI 60-cell test.
Figure 8B:
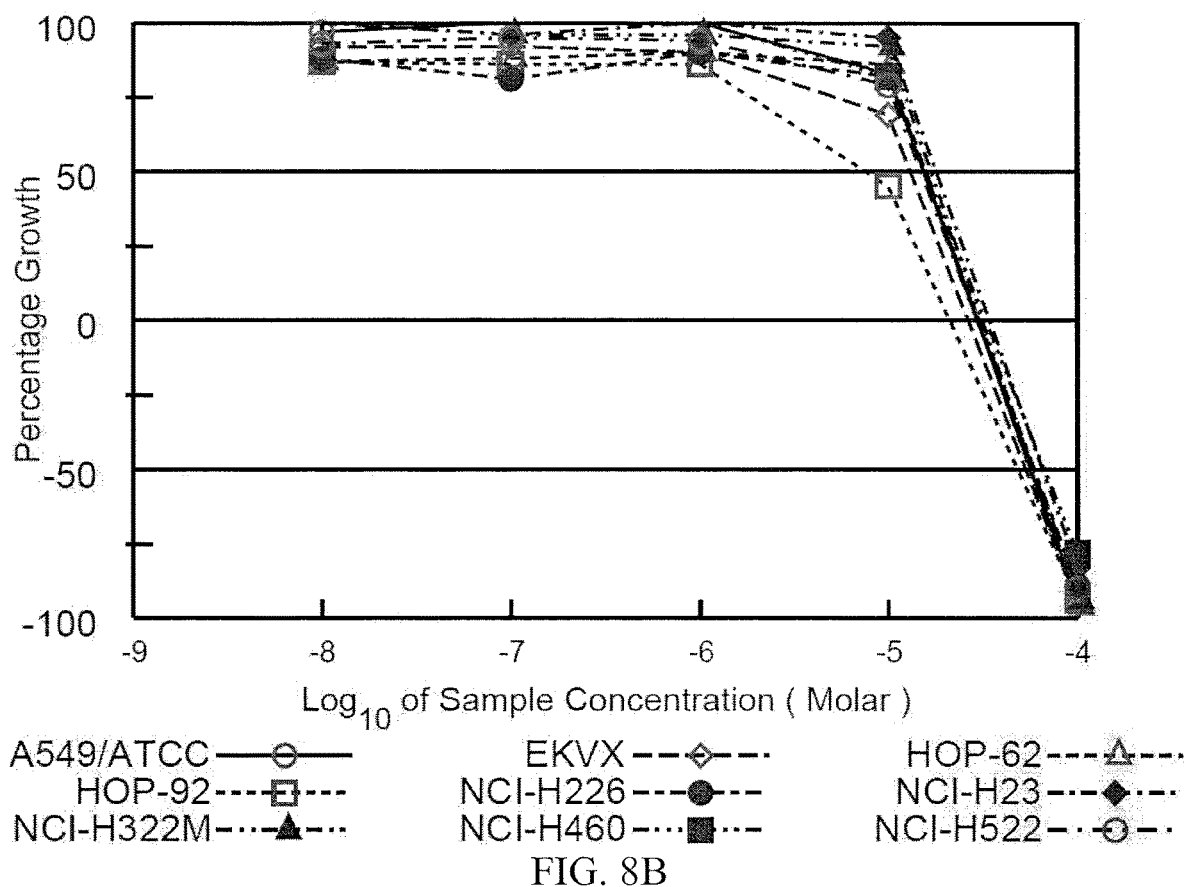
Figure 8C:
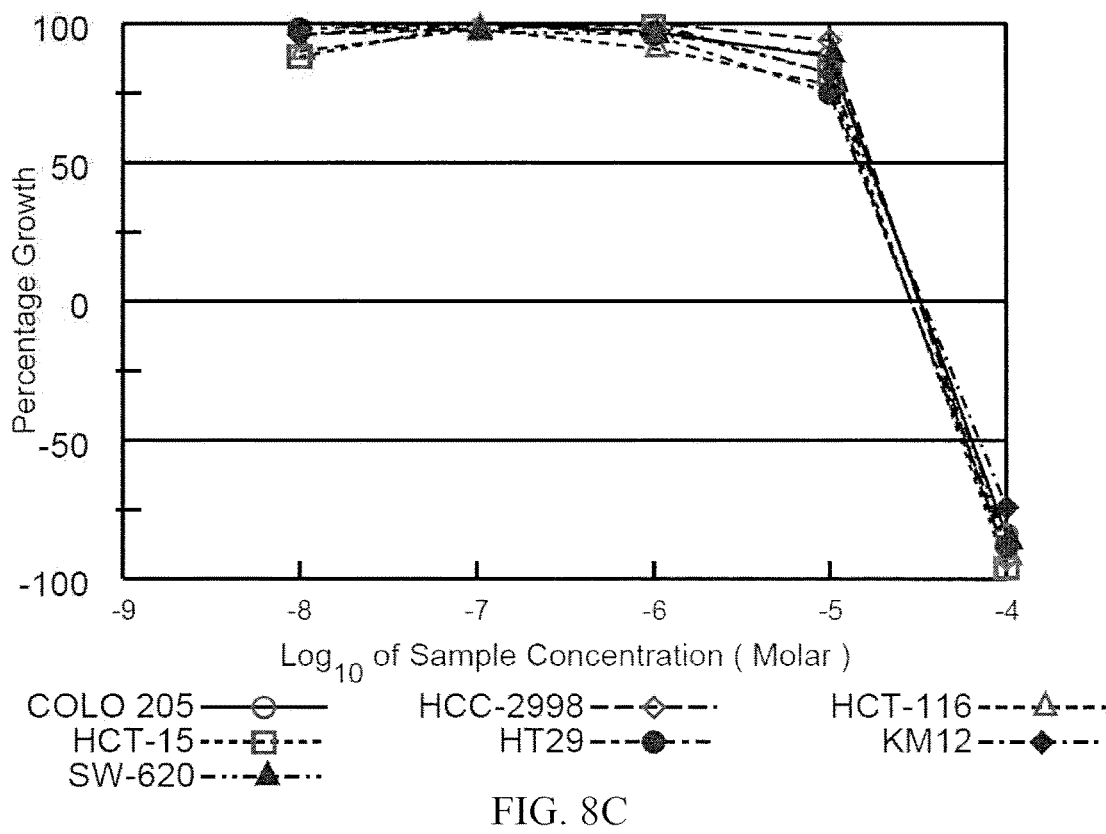
Figure 8D:
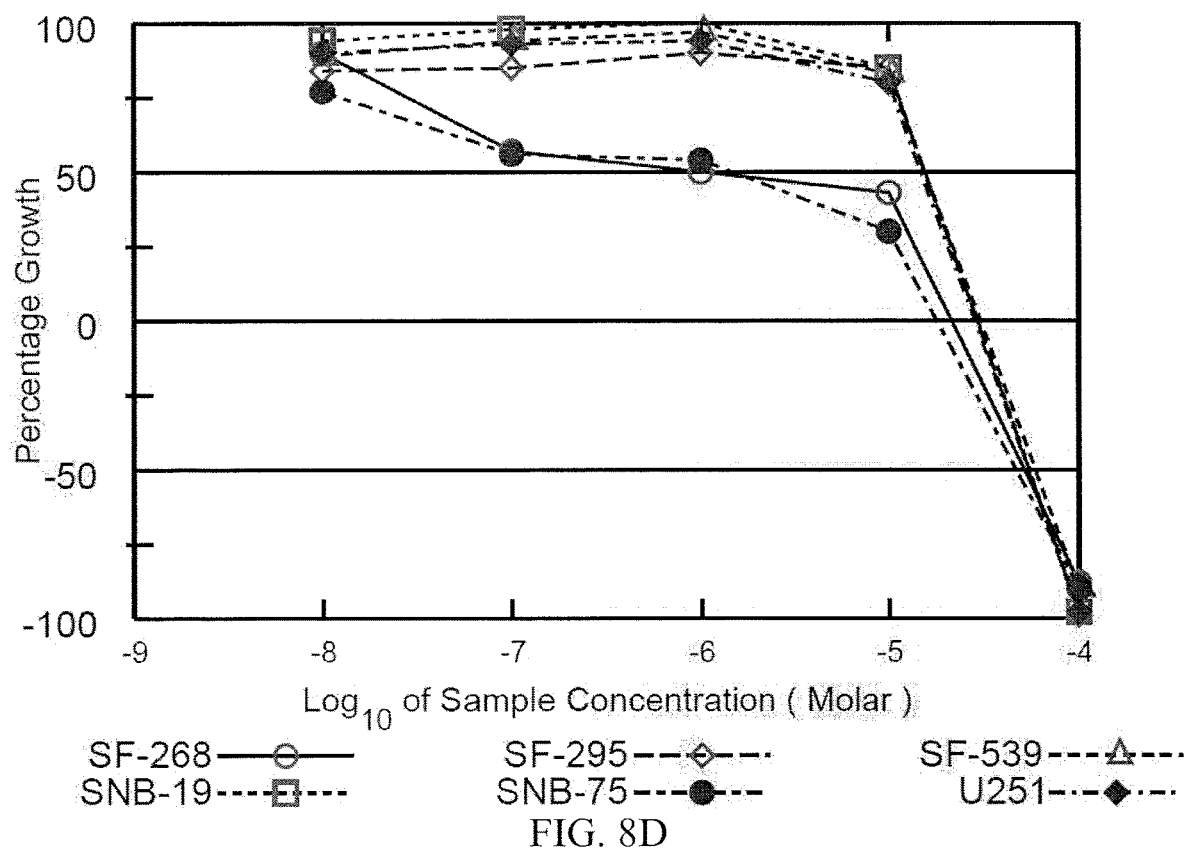
Figure 8E:
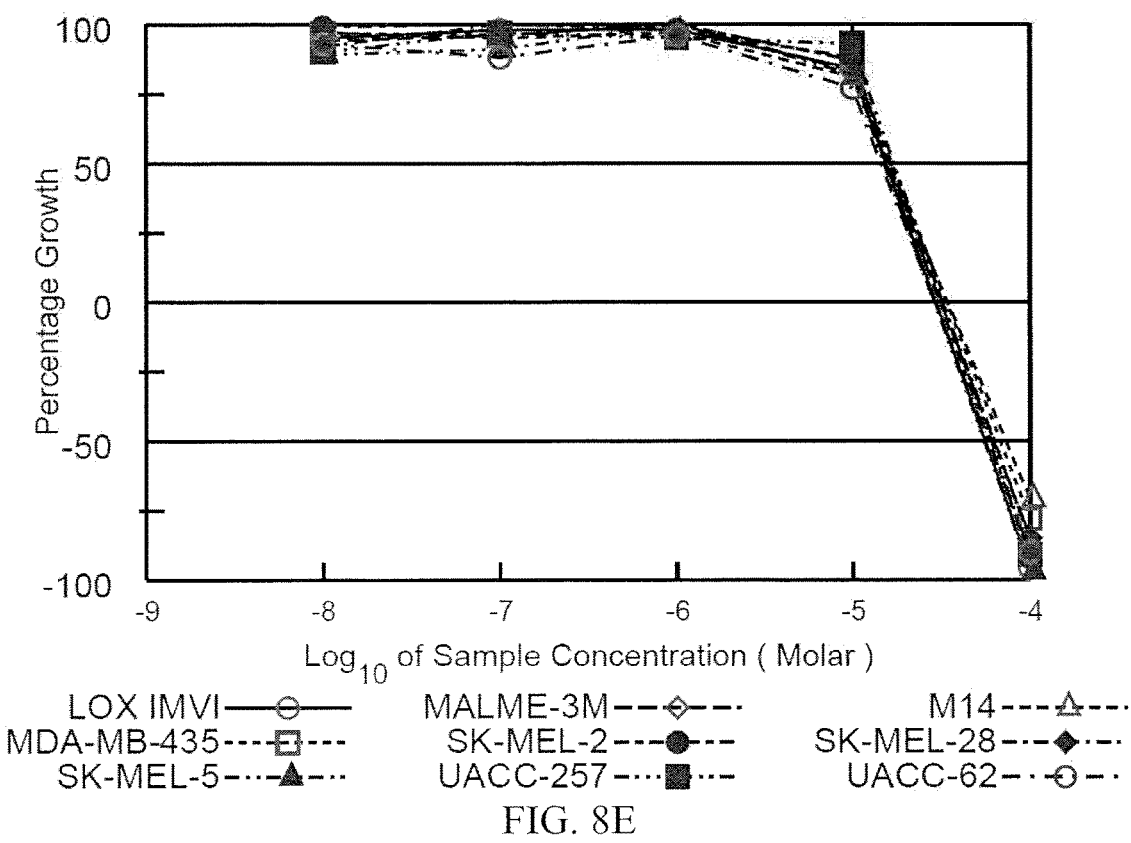
Figure 8F:
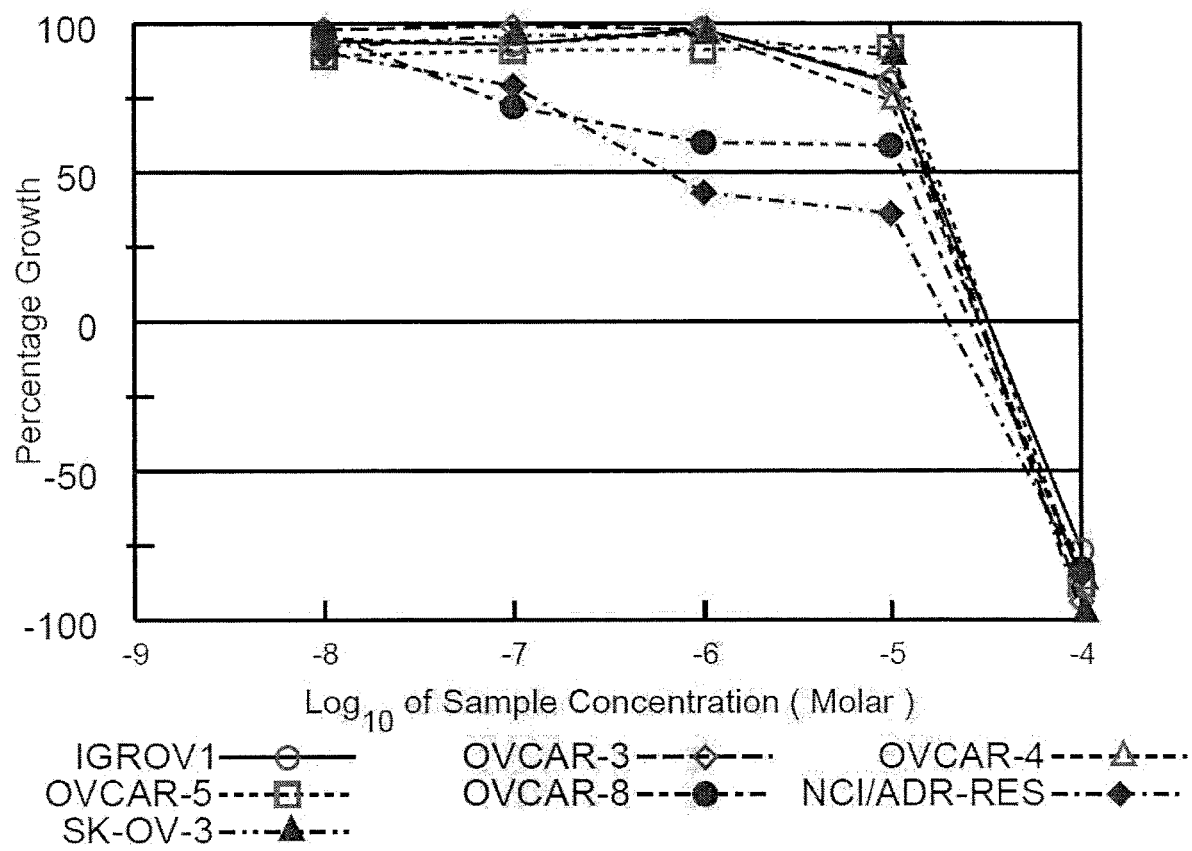
Figure 8G:
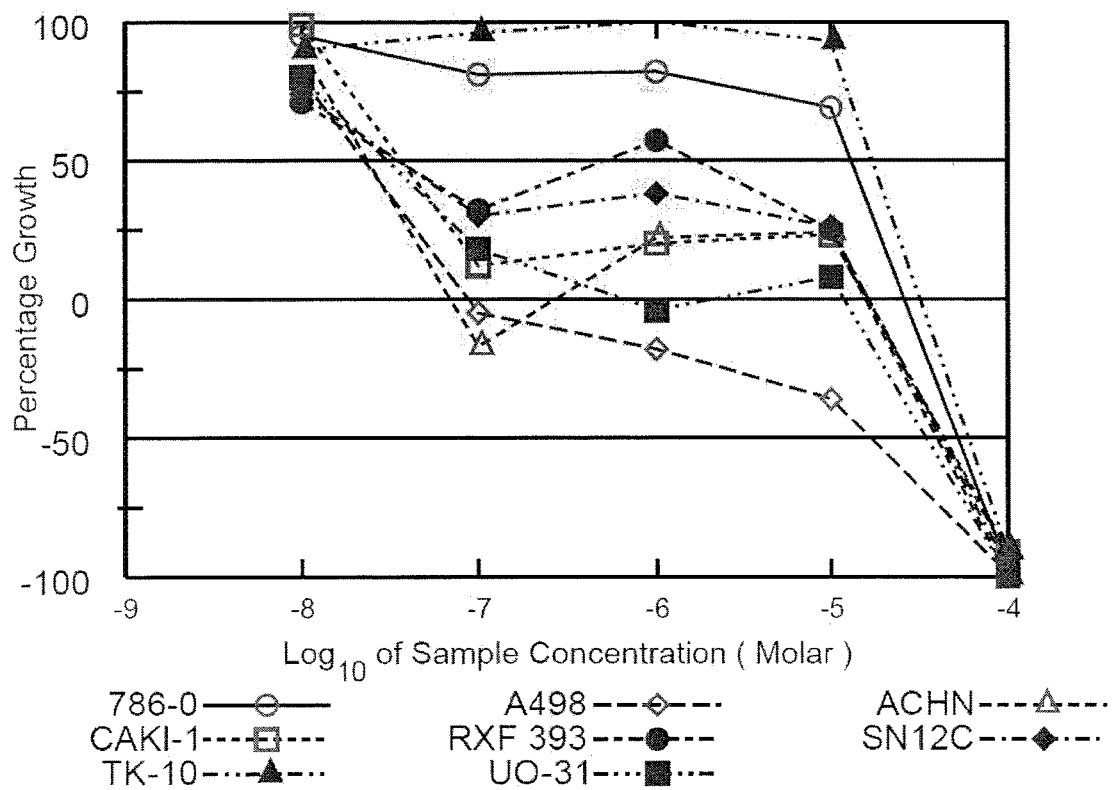
Figure 8H:
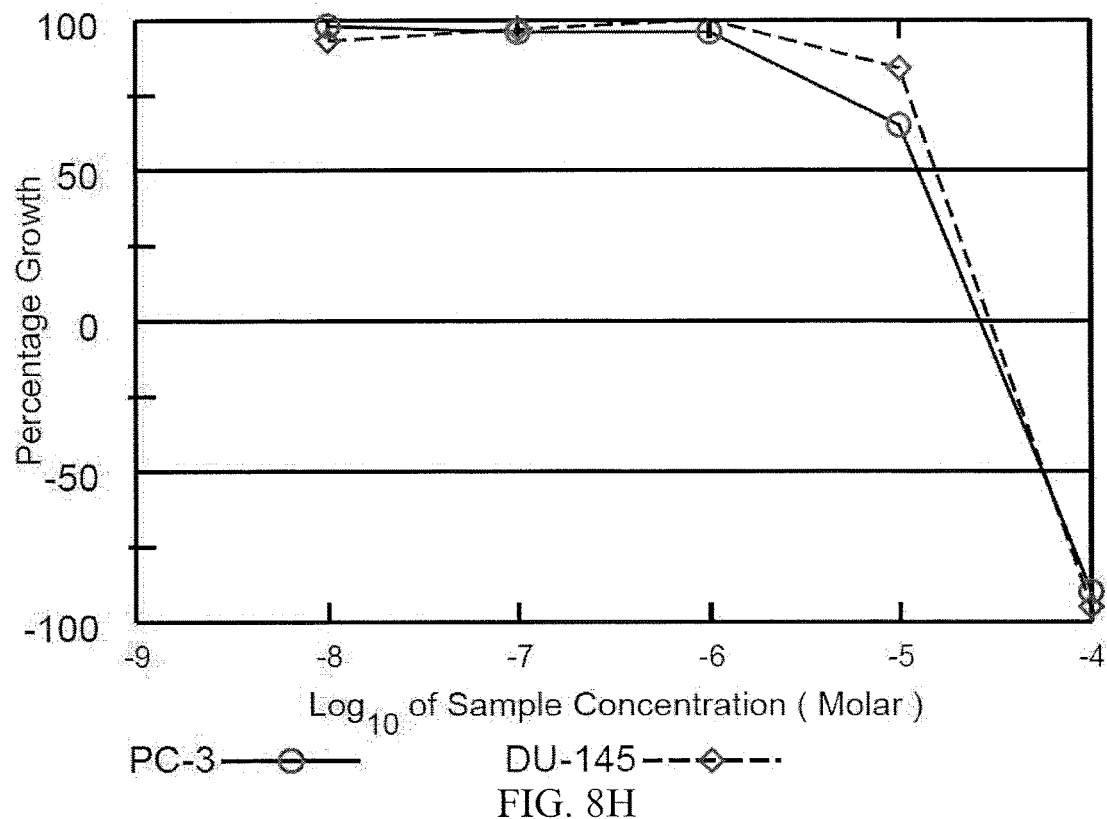
Figure 8I:
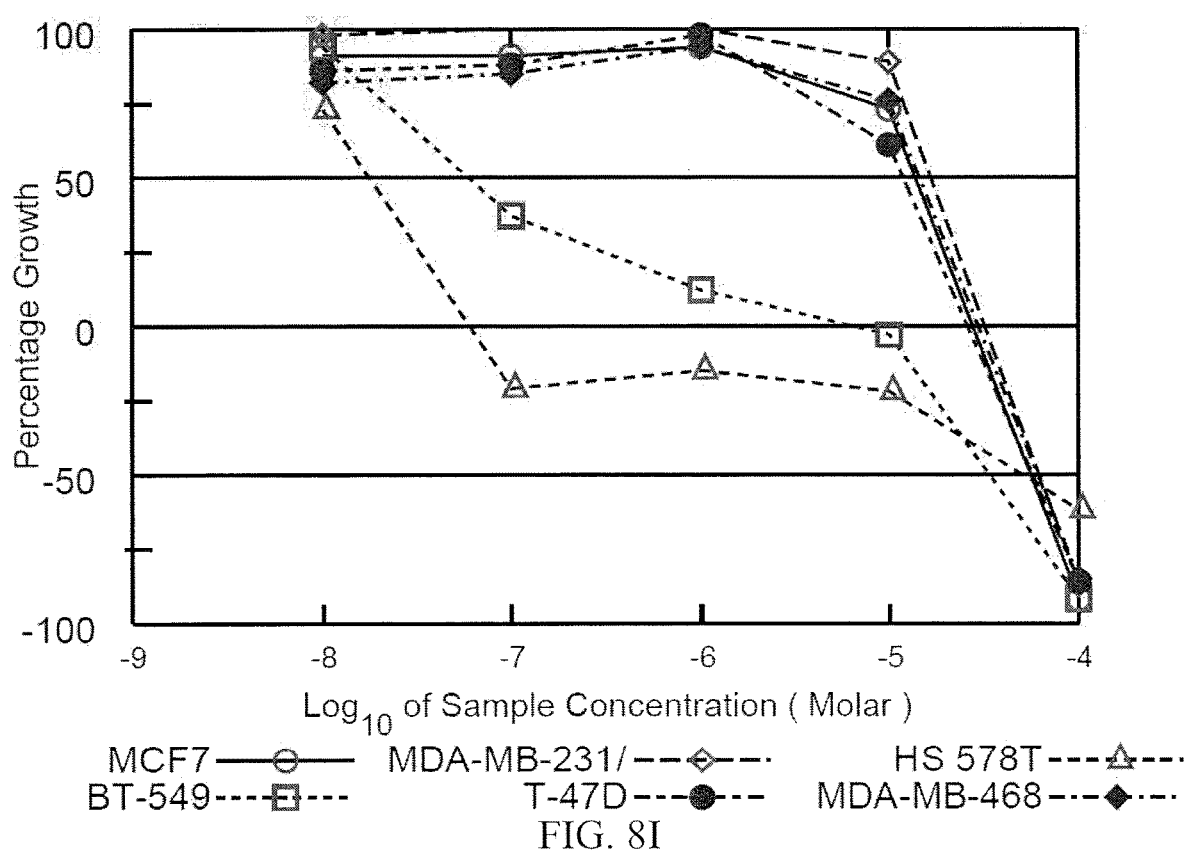
Figure 9A:
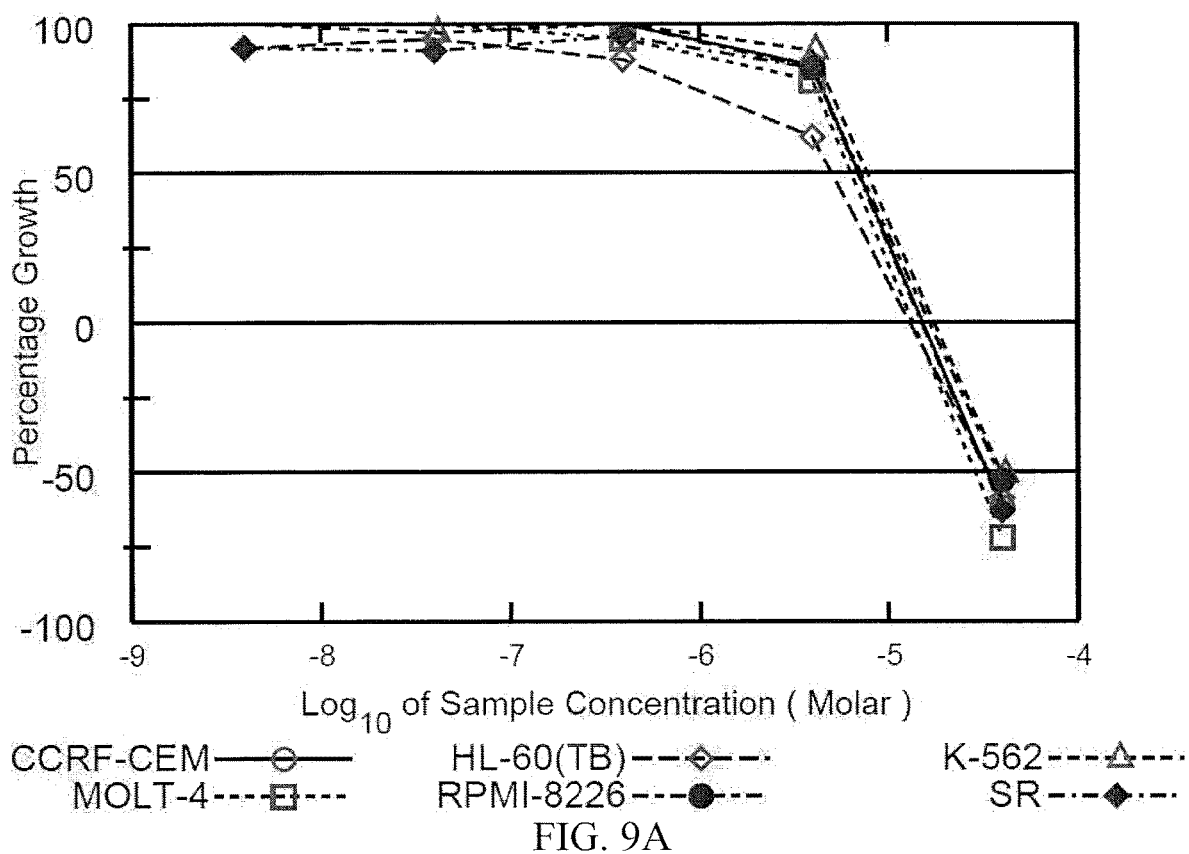
FIG. 9A-9I depict the dose response curves for a compound formula (I) (i.e., (Ie)) against various cancer cell lines in the standard NCI 60-cell test.
Figure 9B:
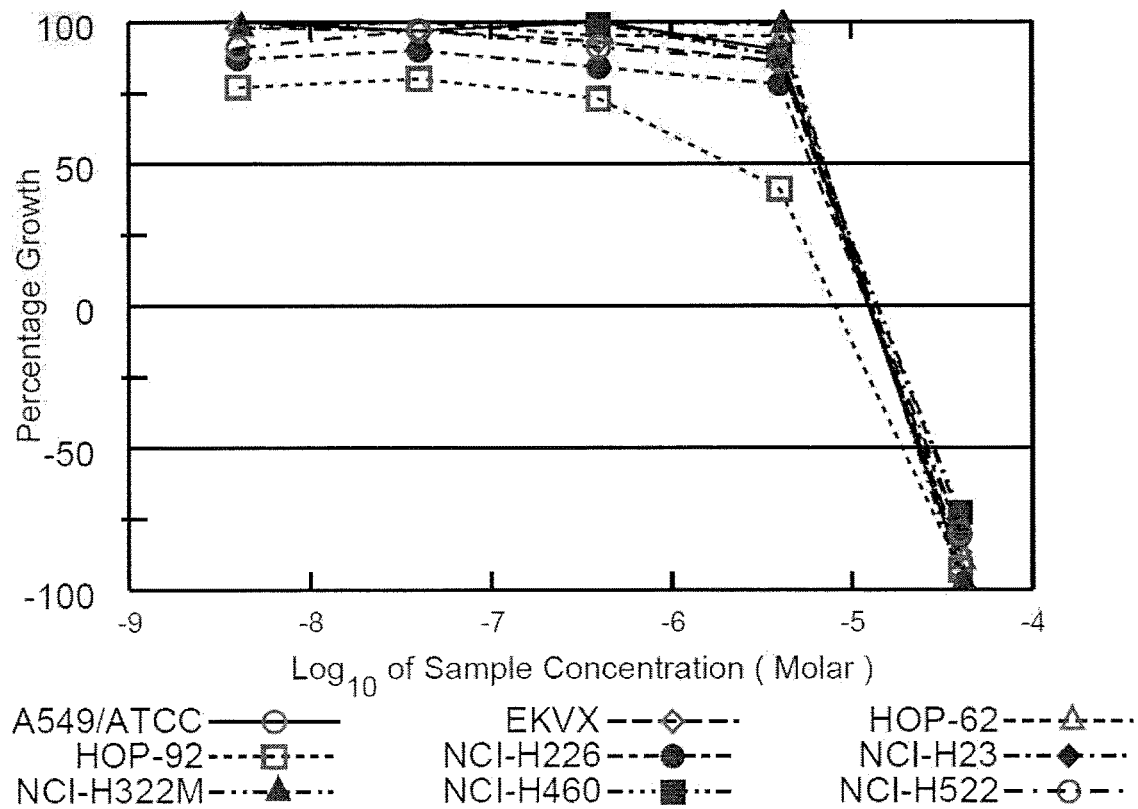
Figure 9C:
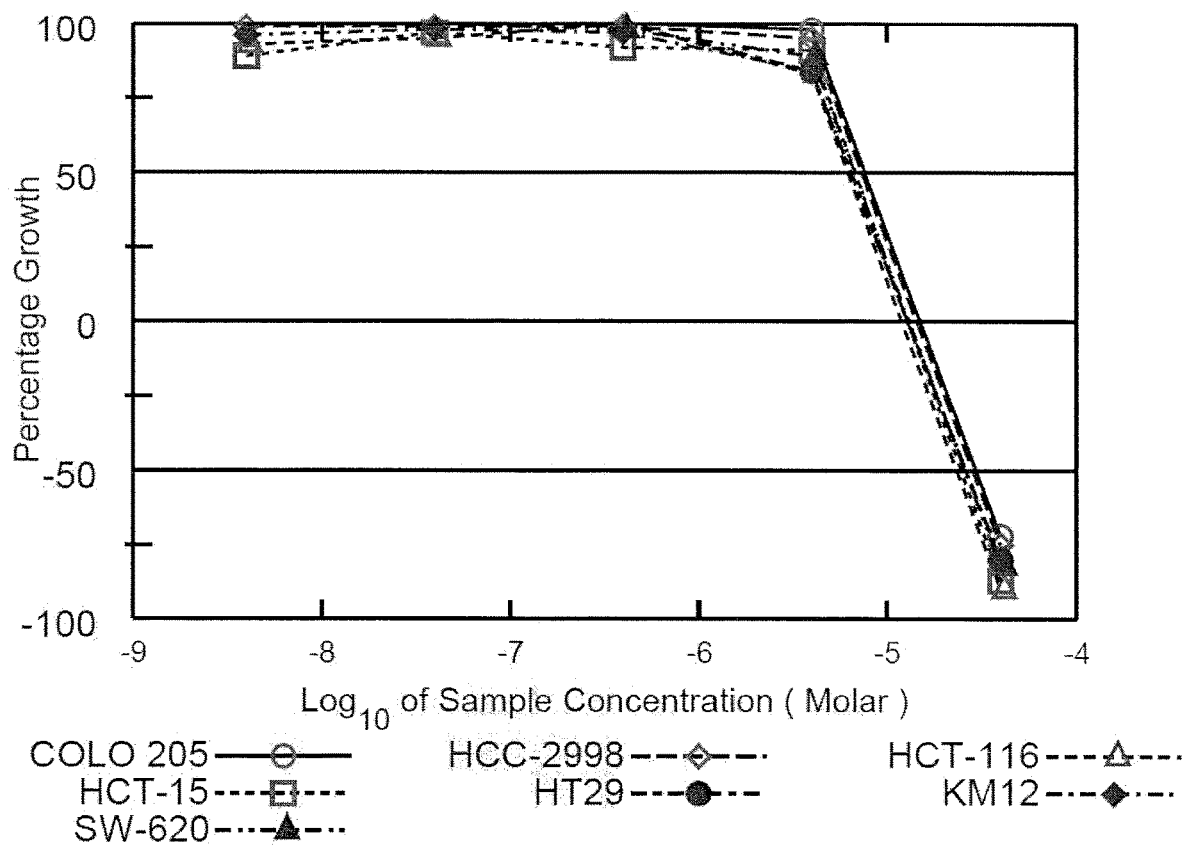
Figure 9D:
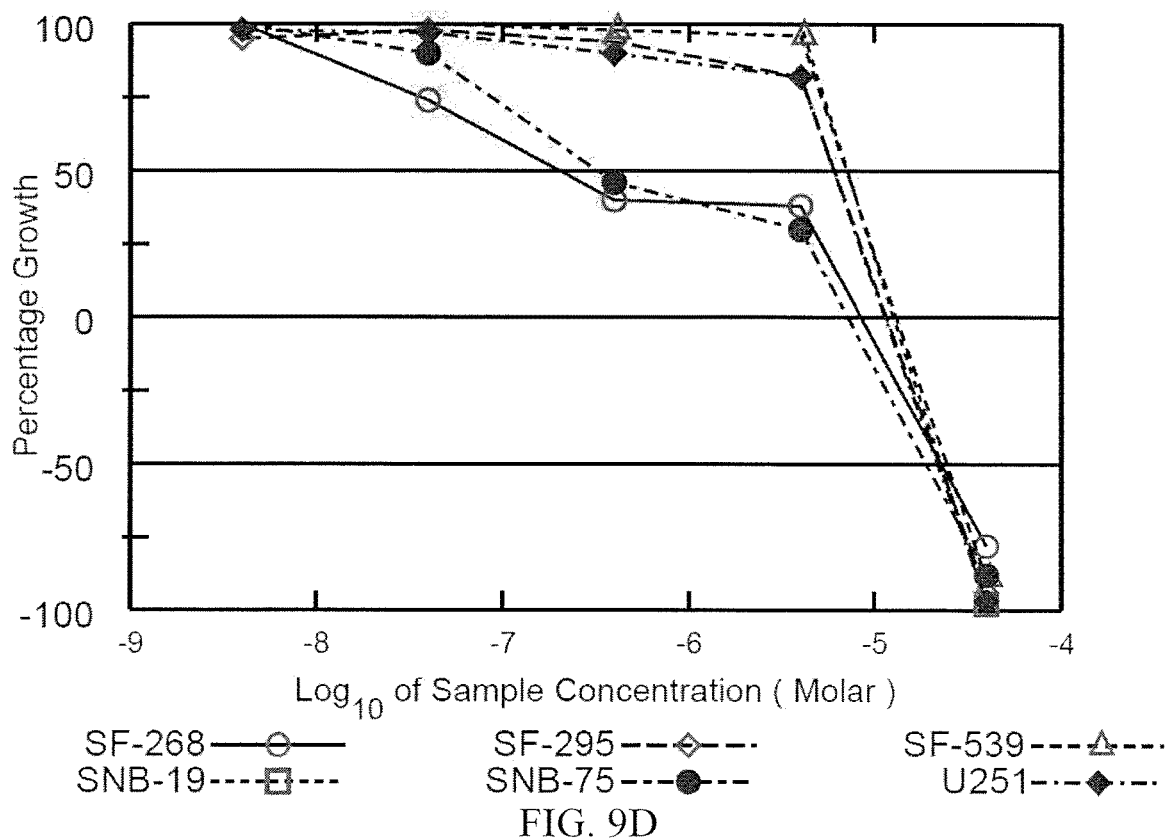
Figure 9E:
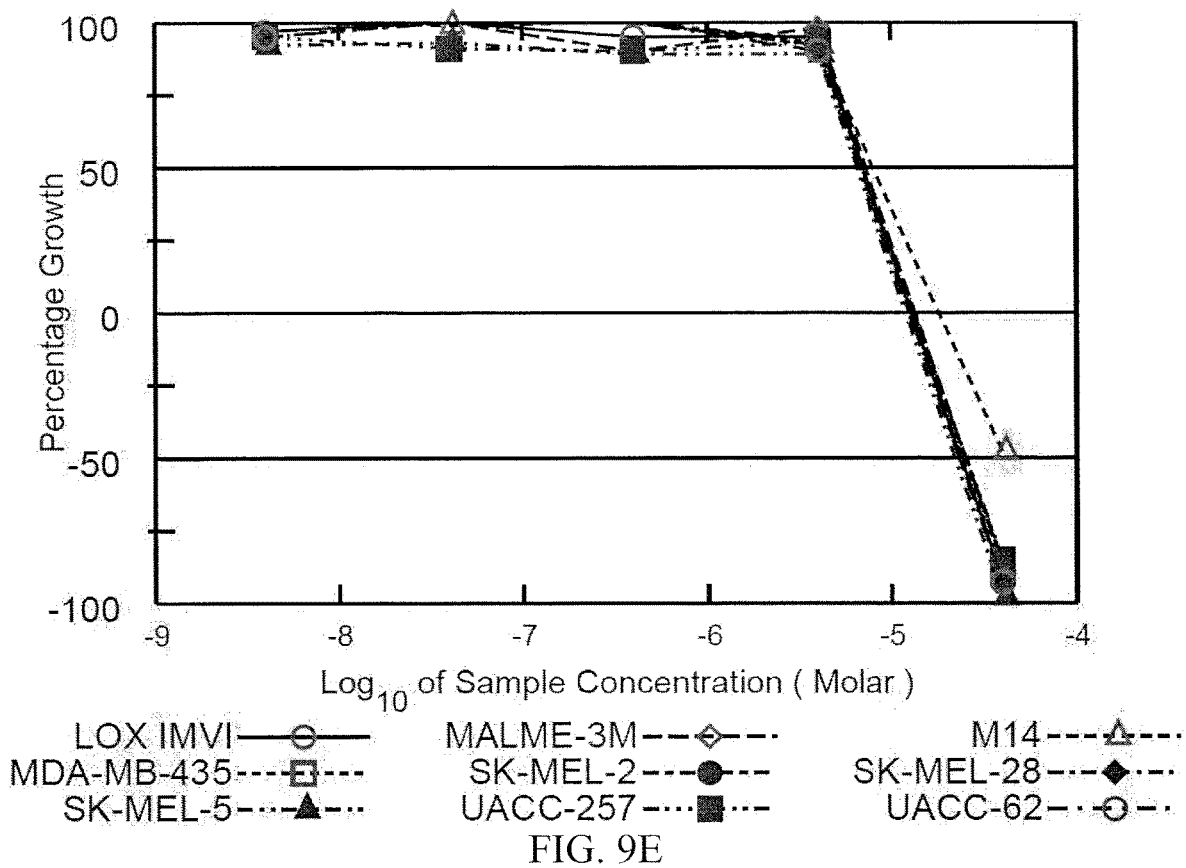
Figure 9F:
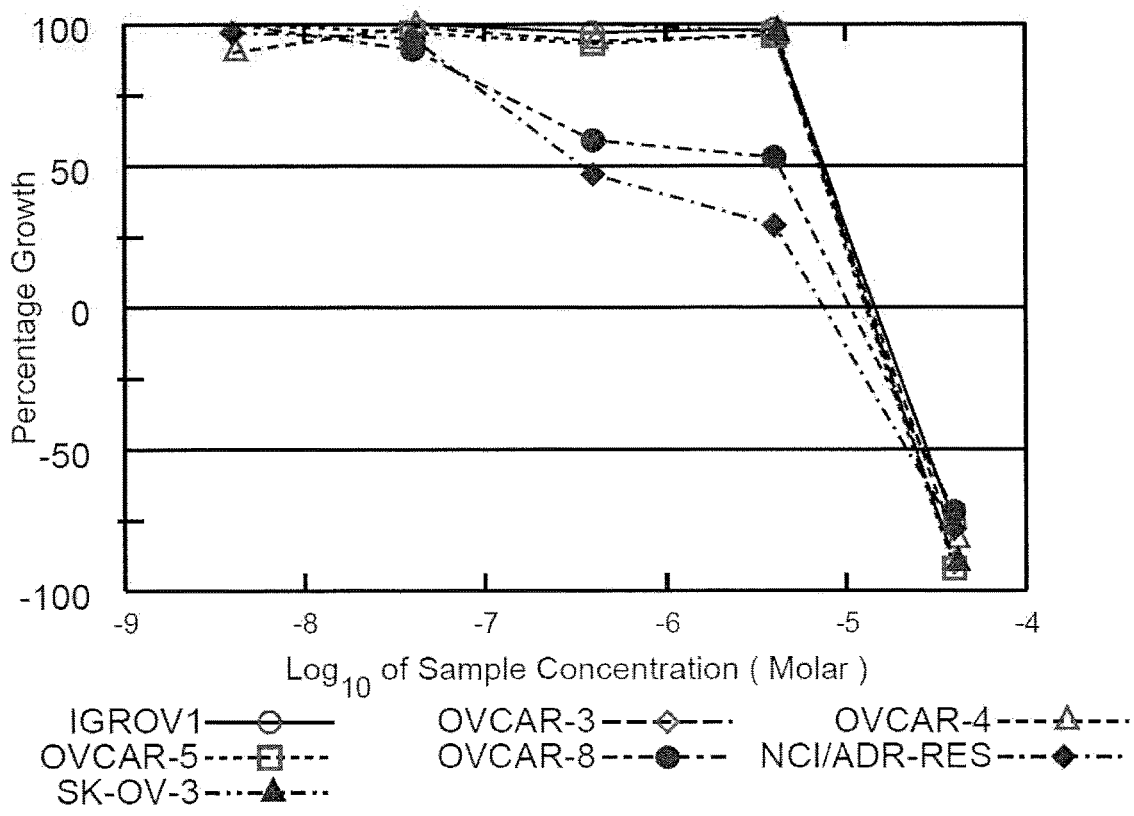
Figure 9G:
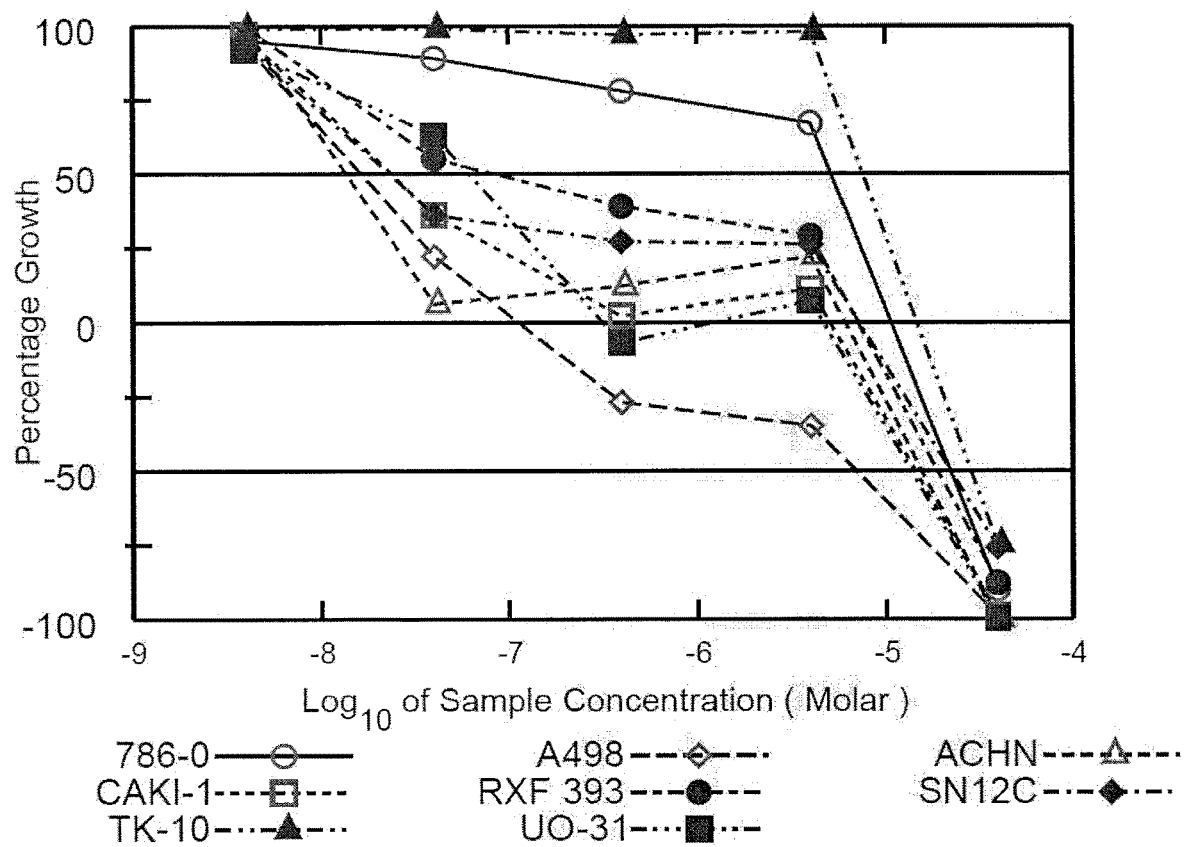
Figure 9H:
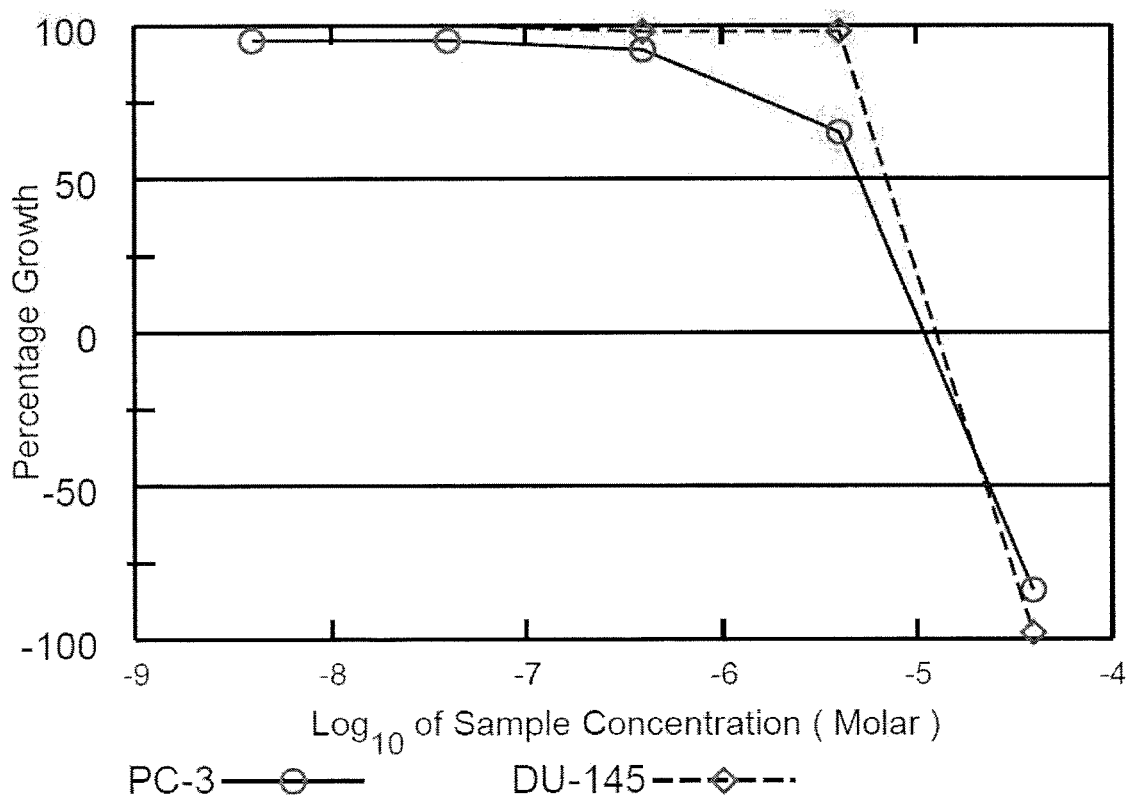
Figure 9I:
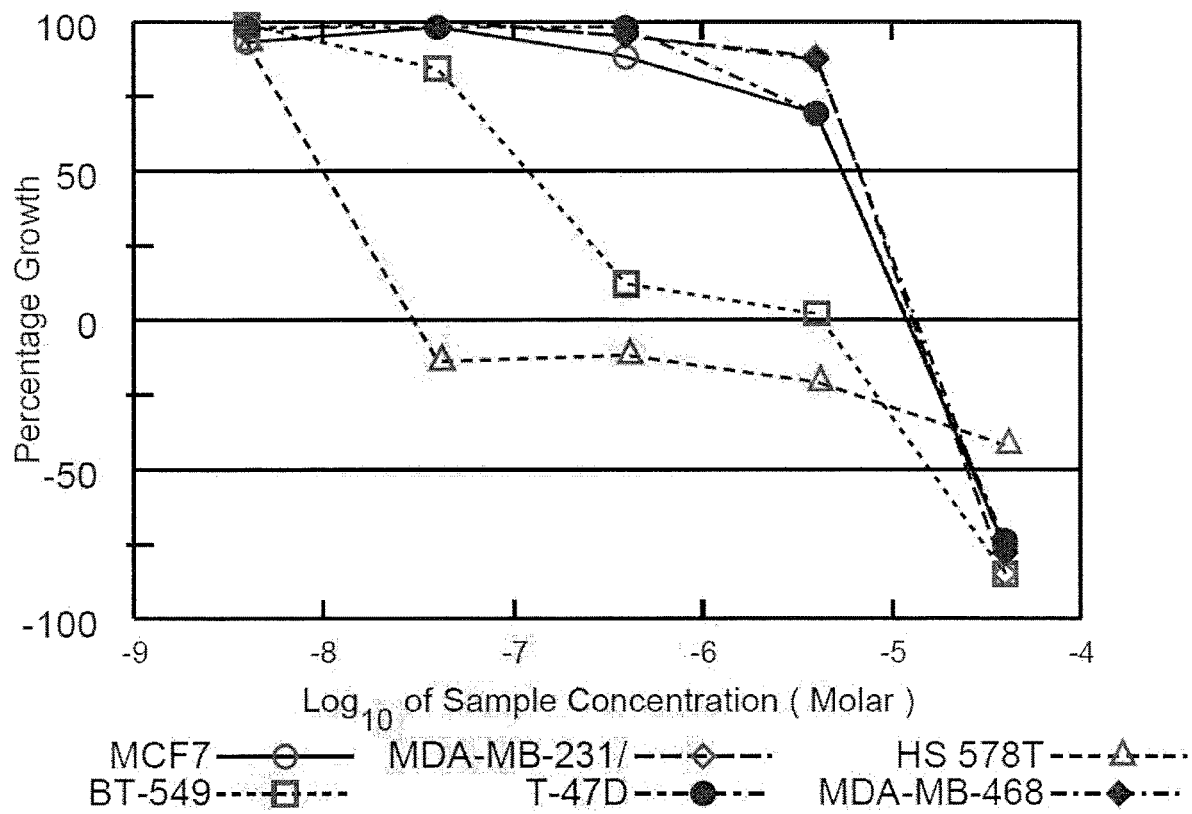
Figure 10A:
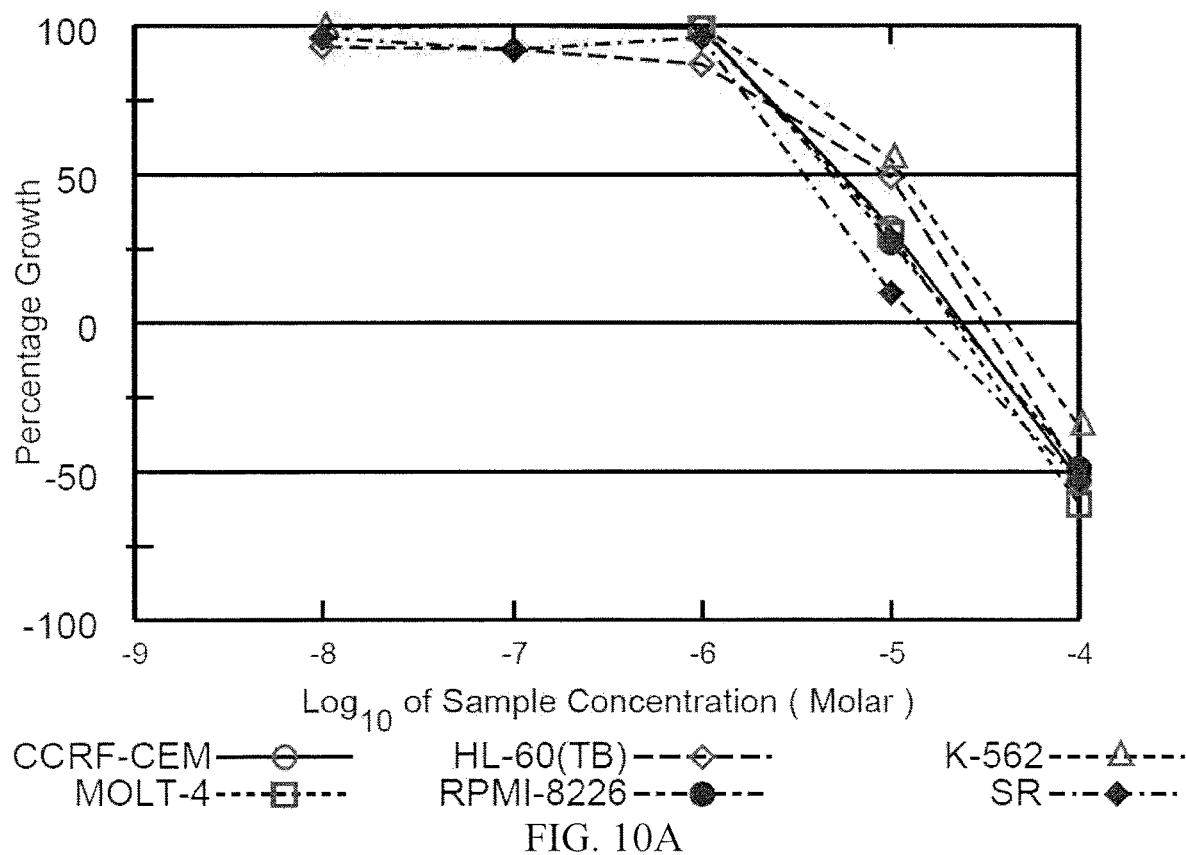
FIG. 10A-10I depict the dose response curves for a compound formula (I) (i.e., (If)) against various cancer cell lines in the NCI 60-cell test.
Figure 10B:
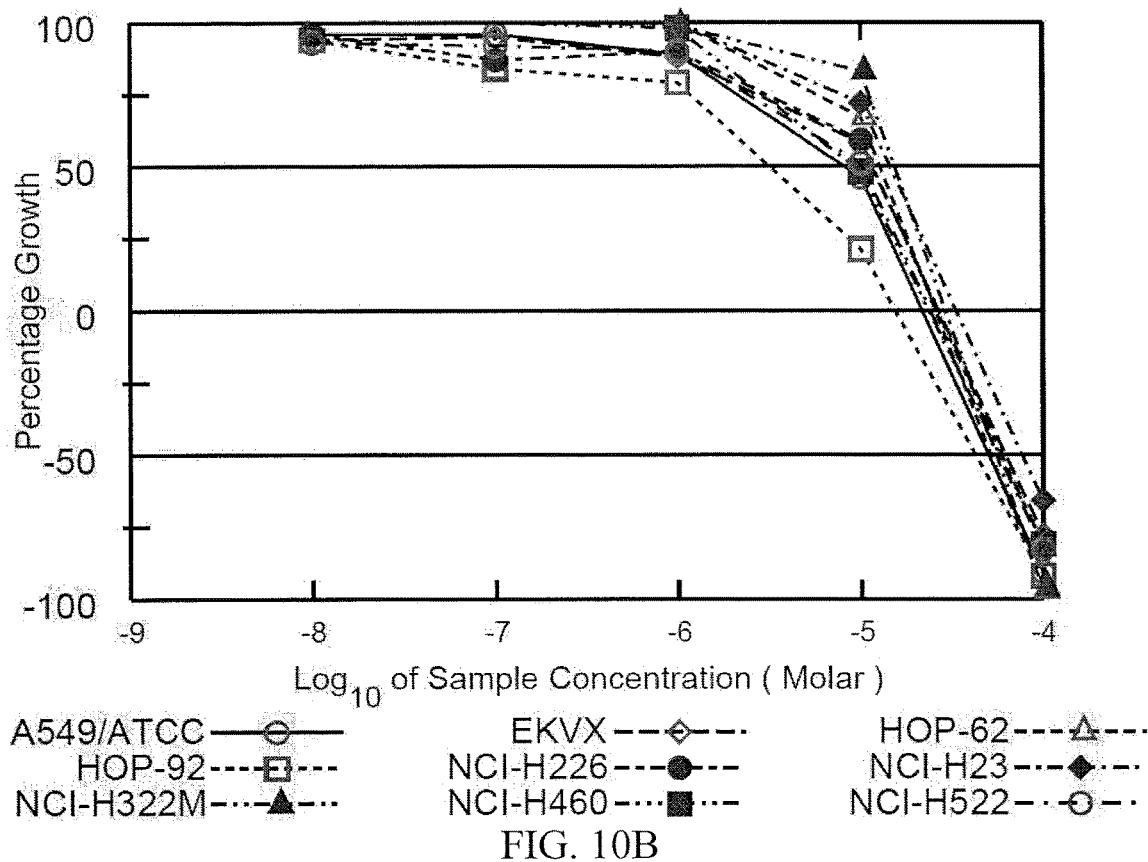
Figure 10C:
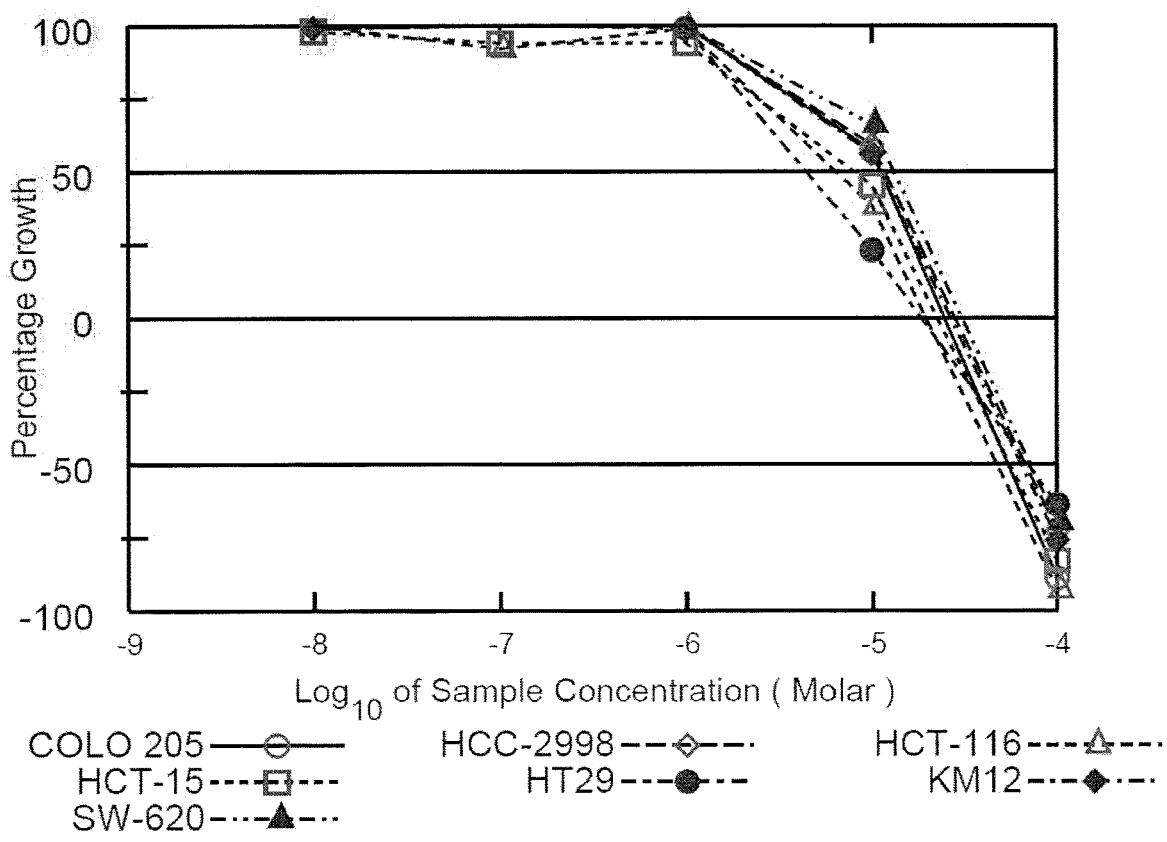
Figure 10D:
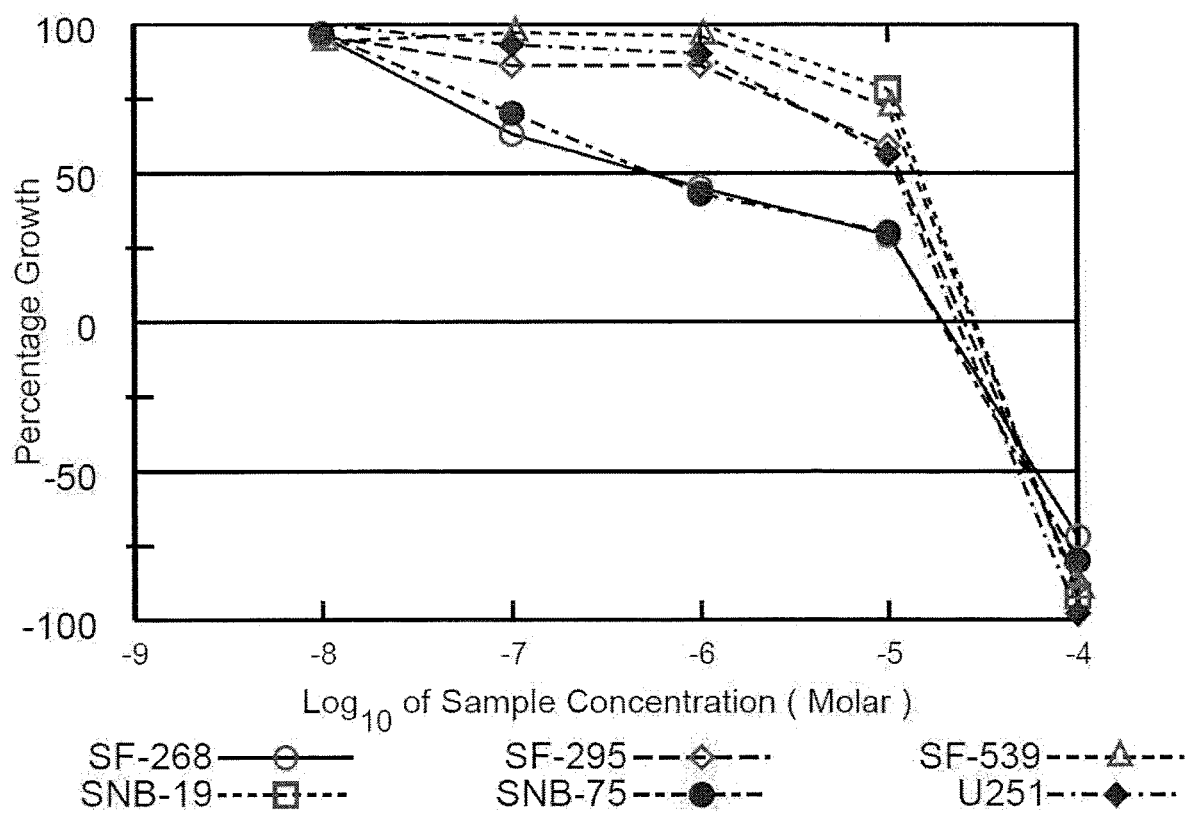
Figure 10E:
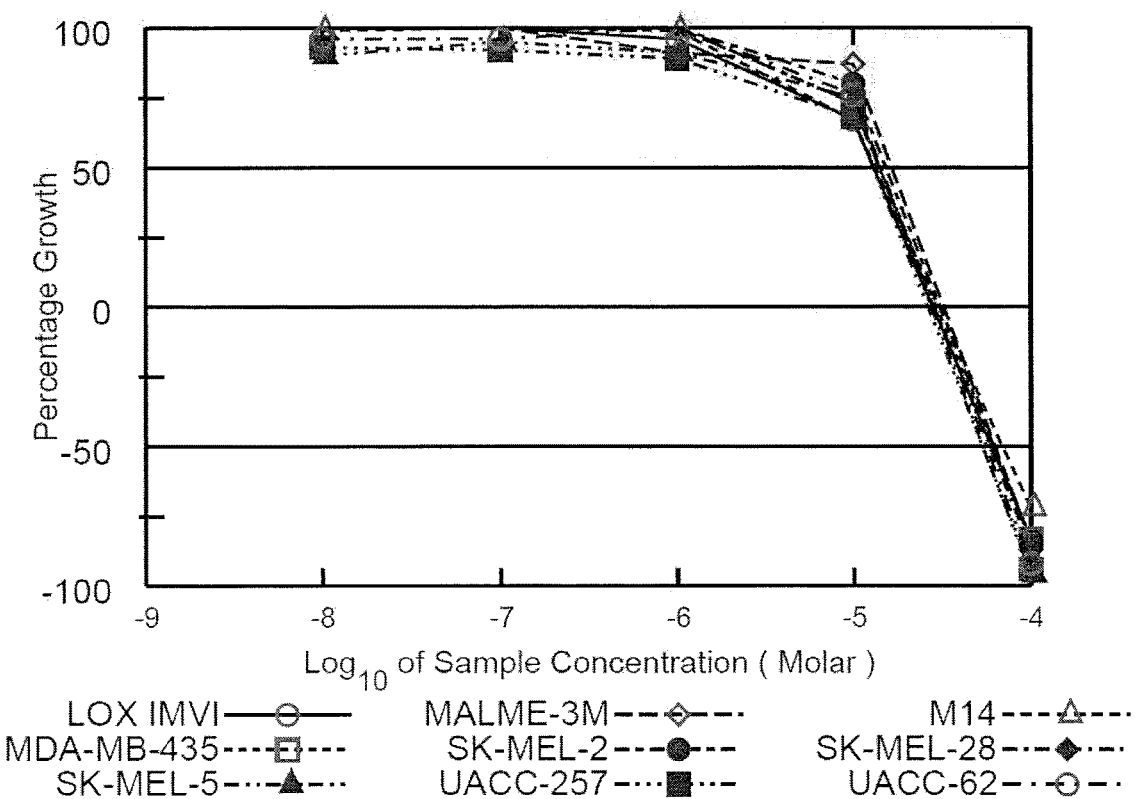
Figure 10F:
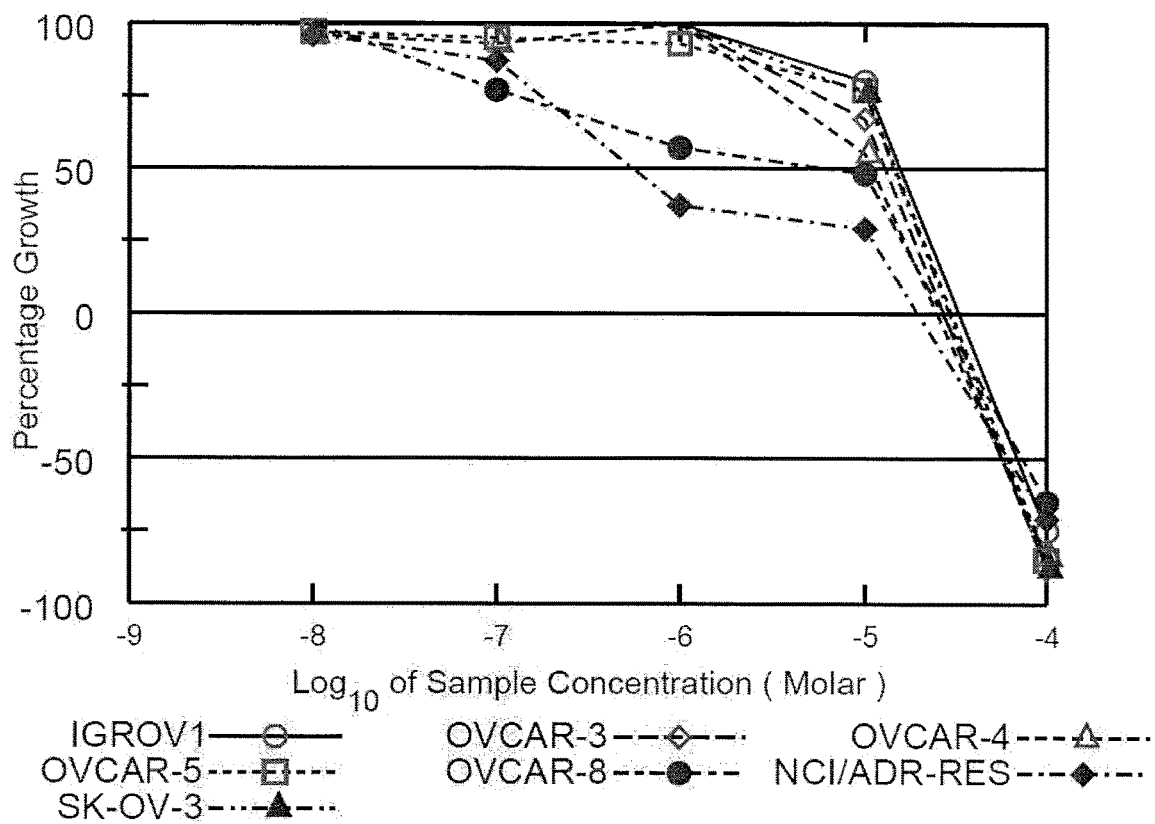
Figure 10G:
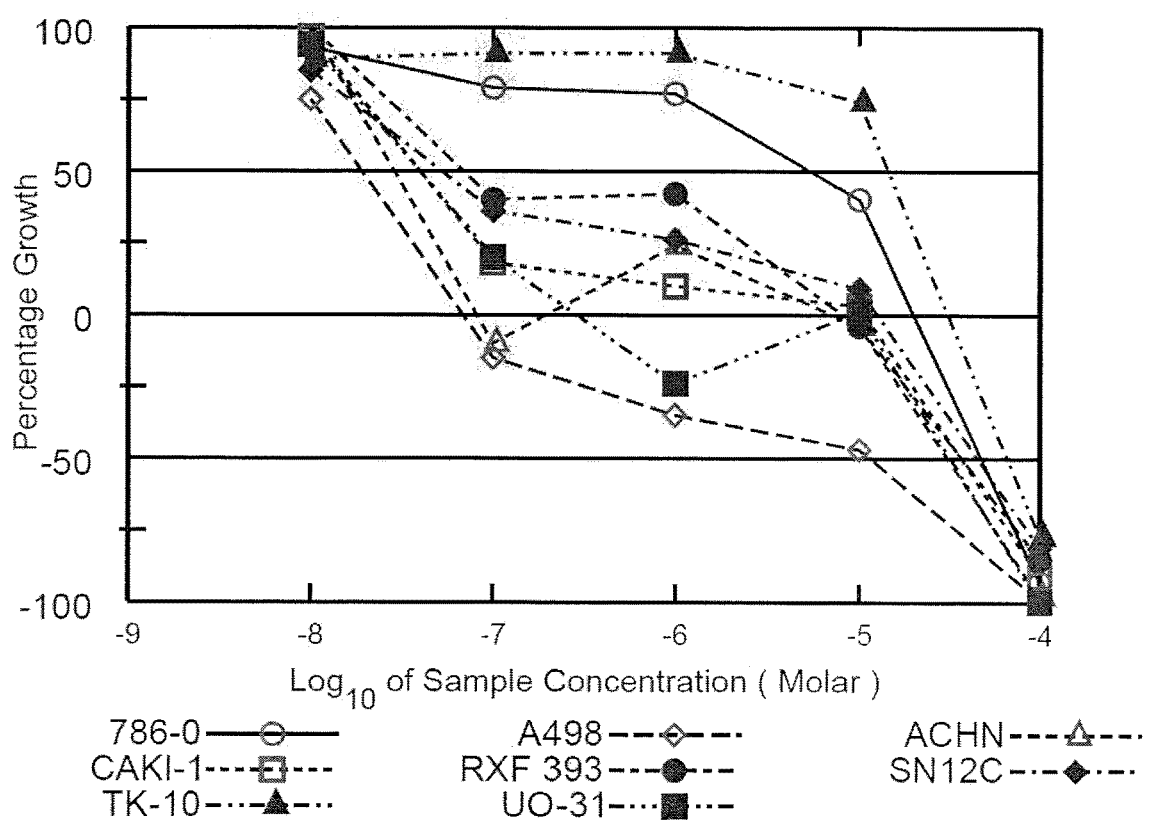
Figure 10H:
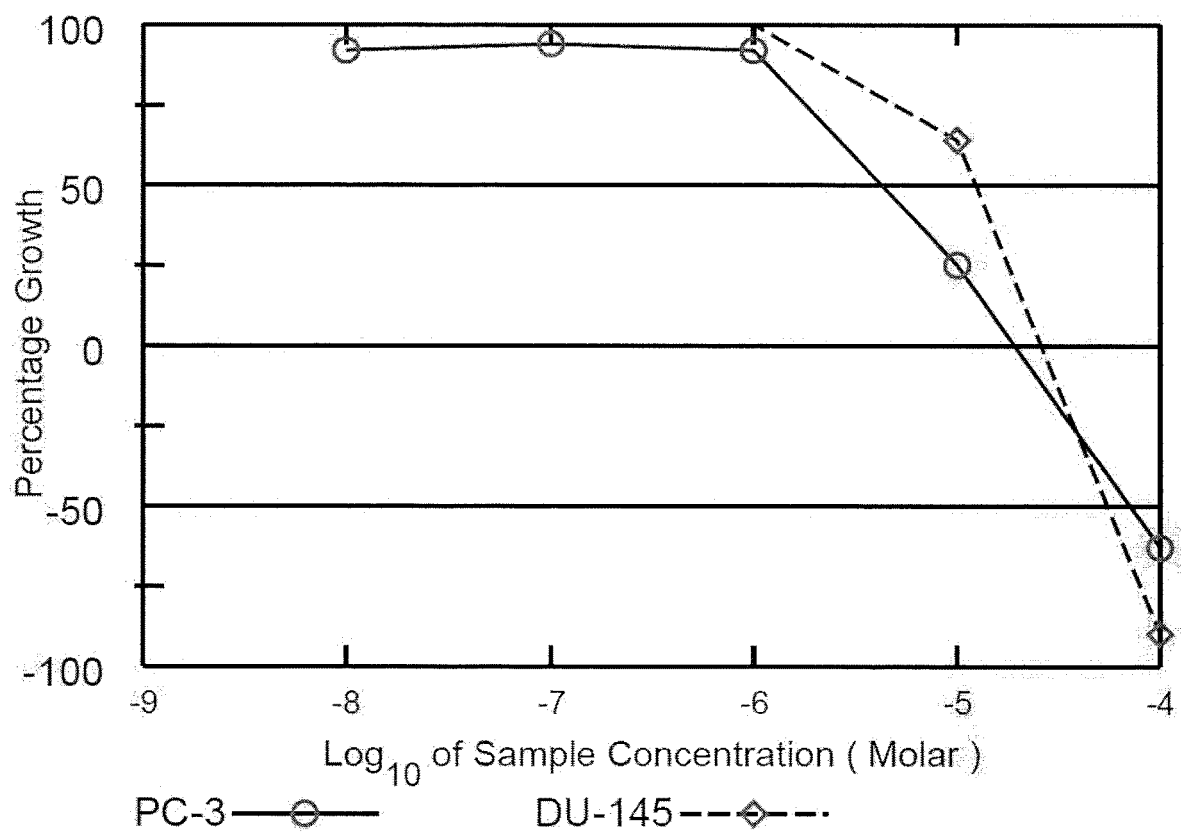
Figure 10I:
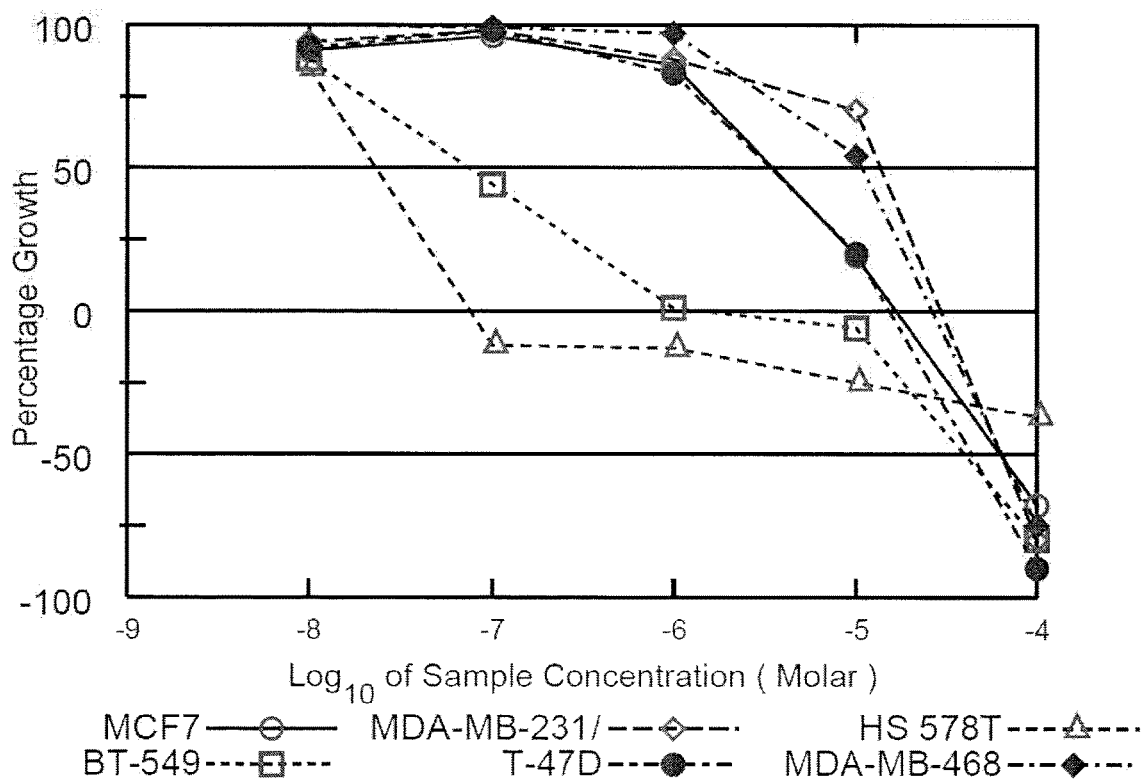
Figure 11A:
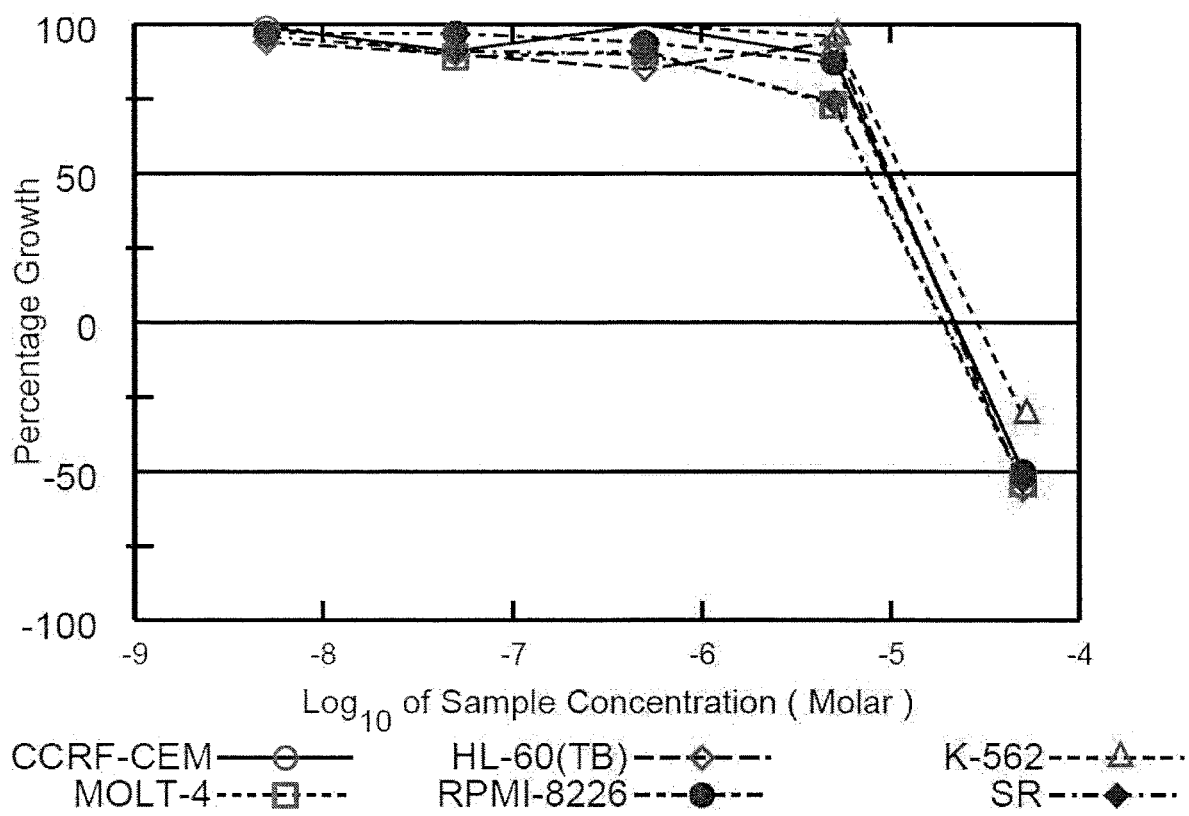
FIG. 11A-11I depict the dose response curves for a compound formula (I) (i.e., (Ig) against various cancer cell lines in the NCI 60-cell test.
Figure 11B:
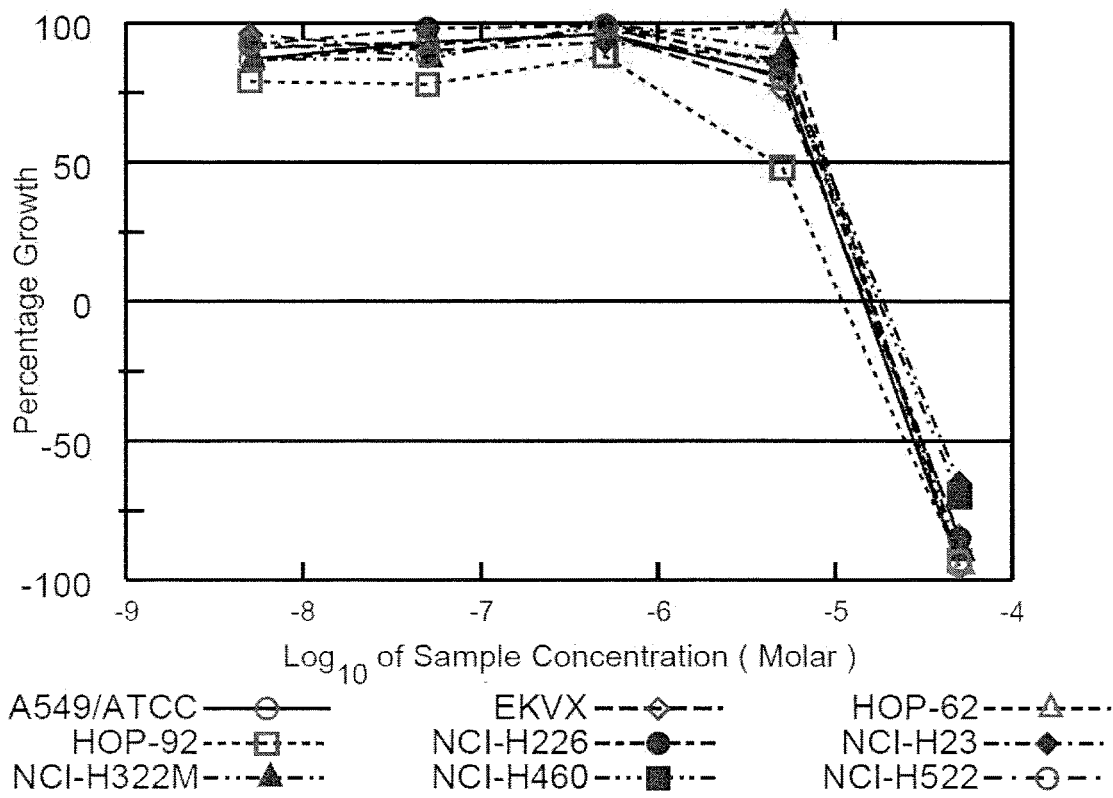
Figure 11C:
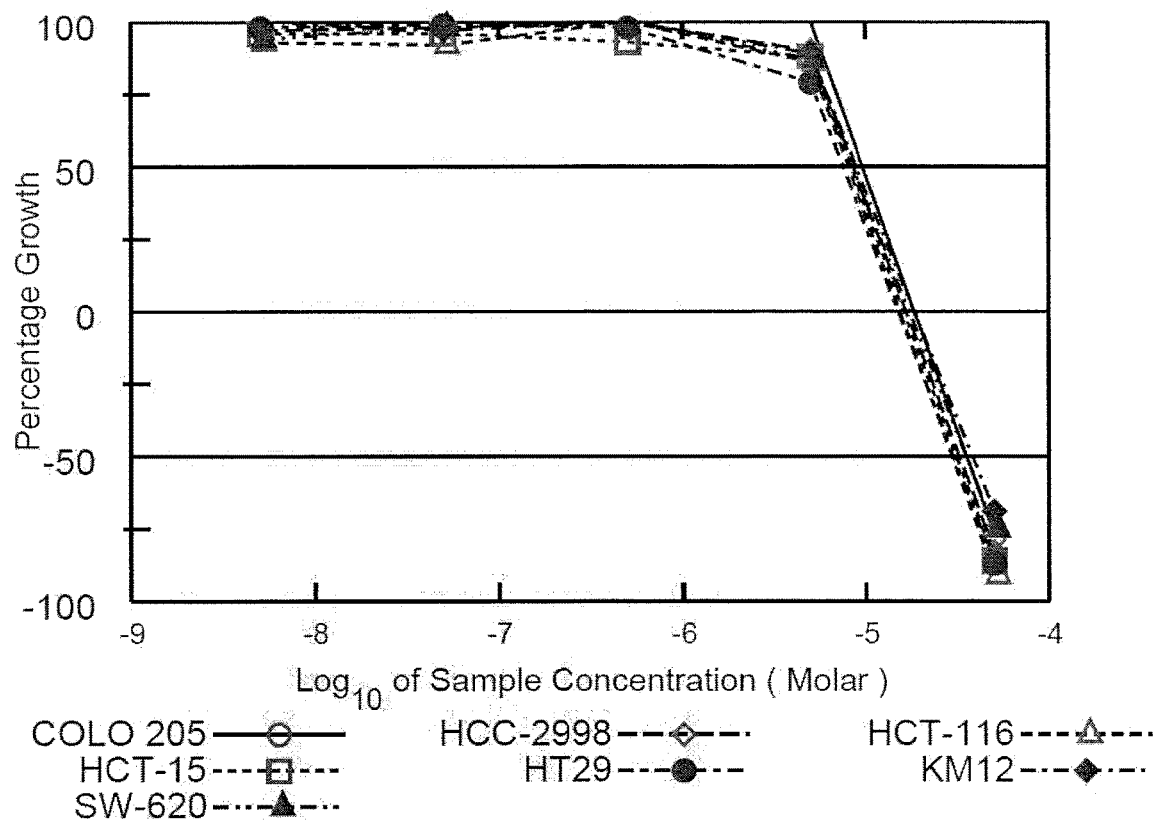
Figure 11D:
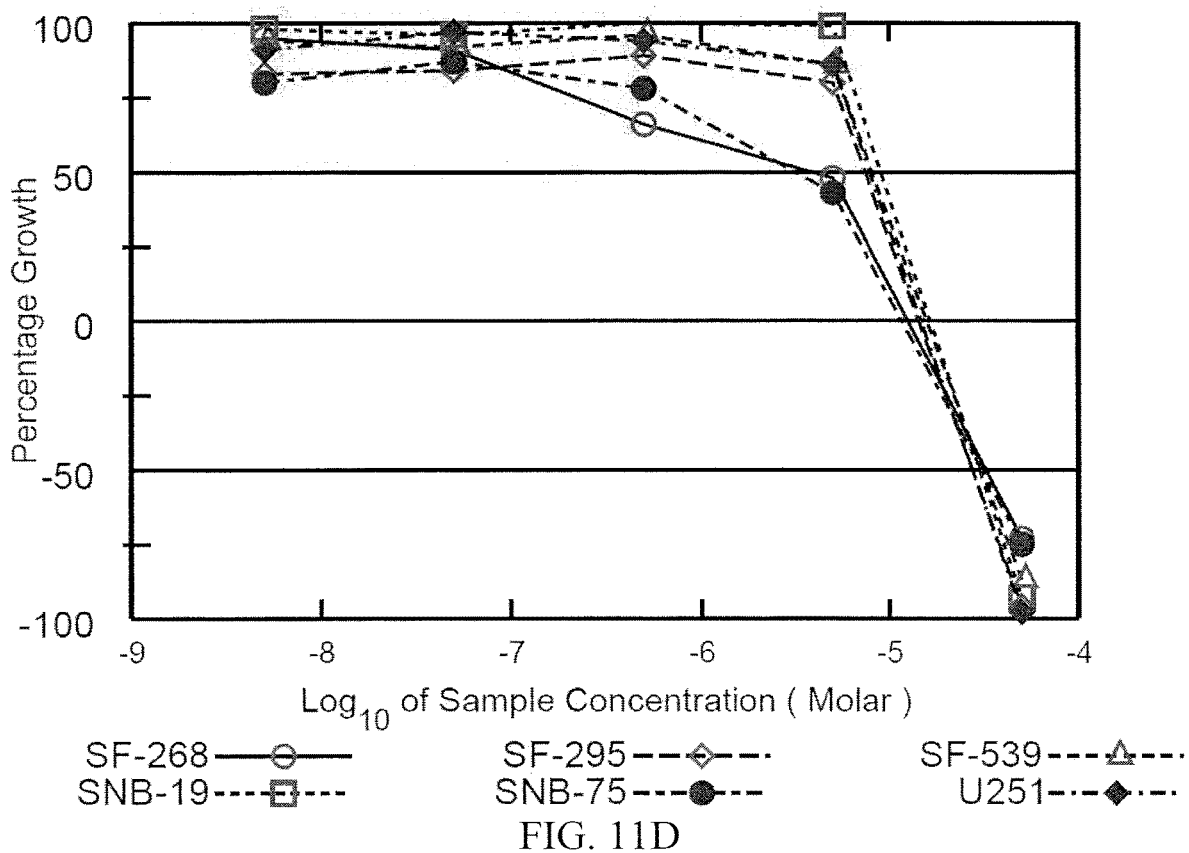
Figure 11E:
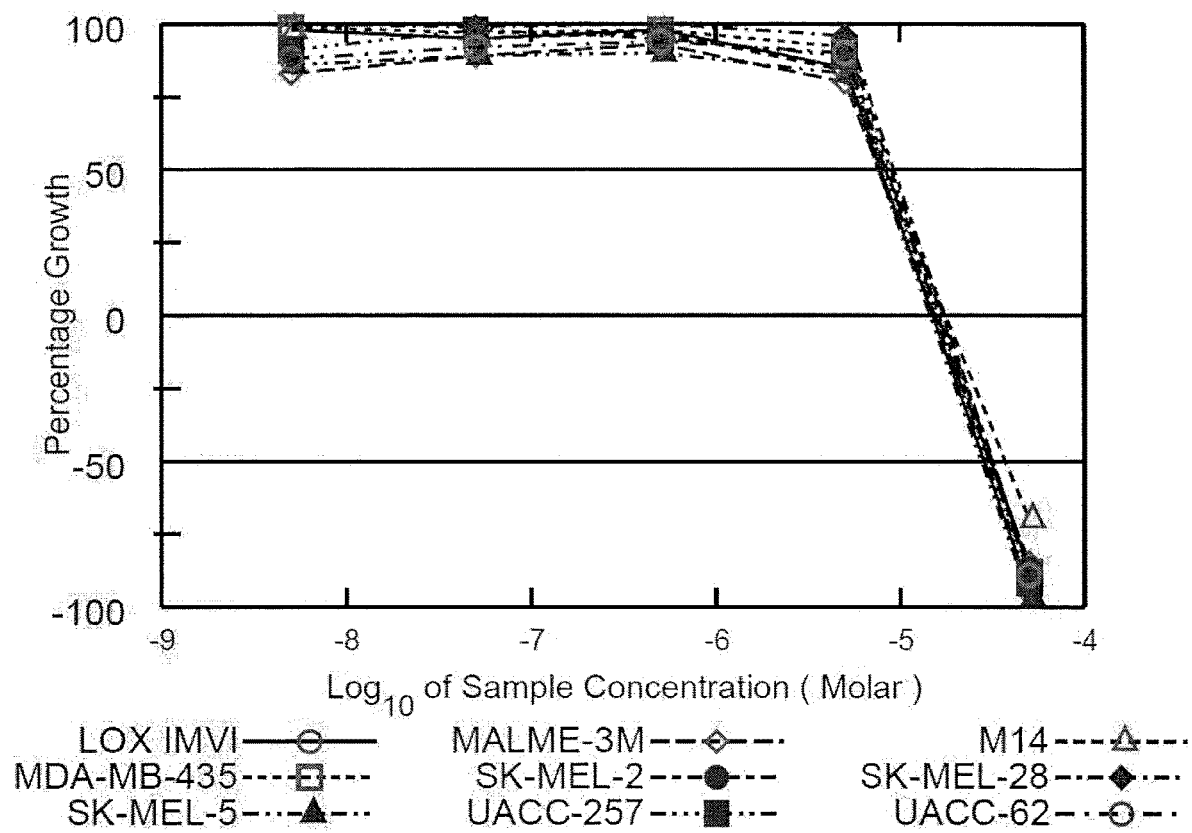
Figure 11F:
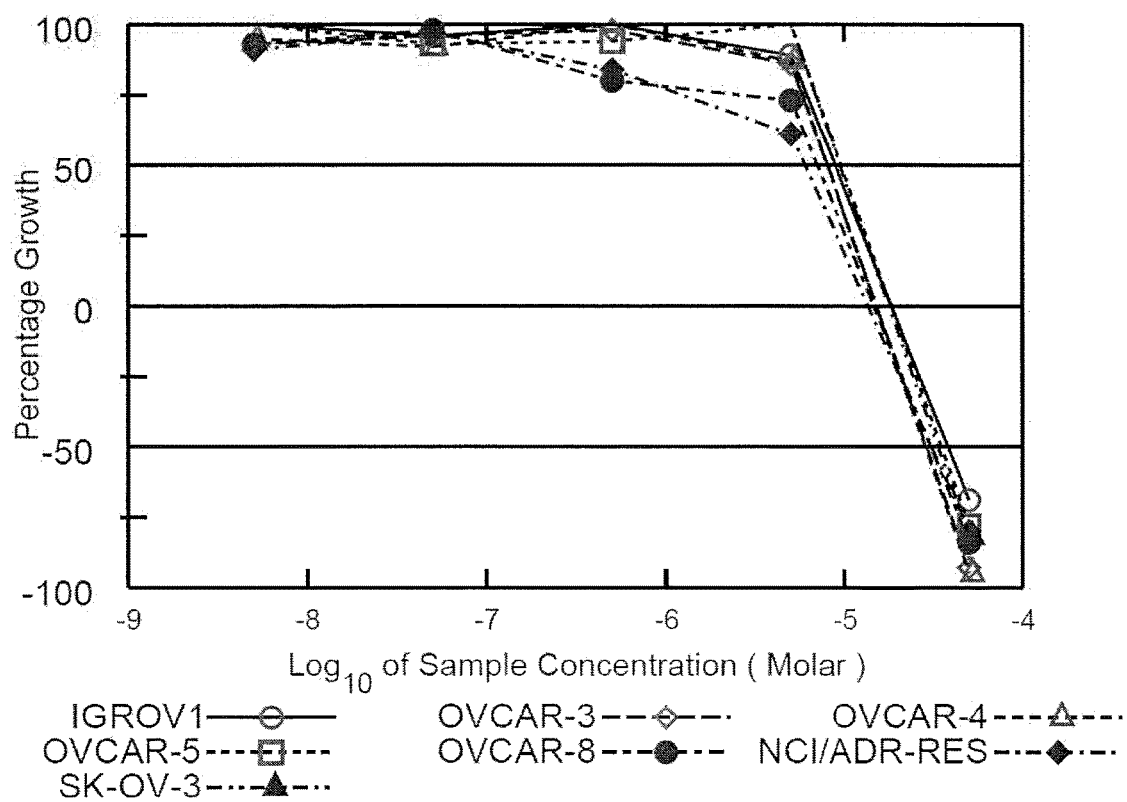
Figure 11G:
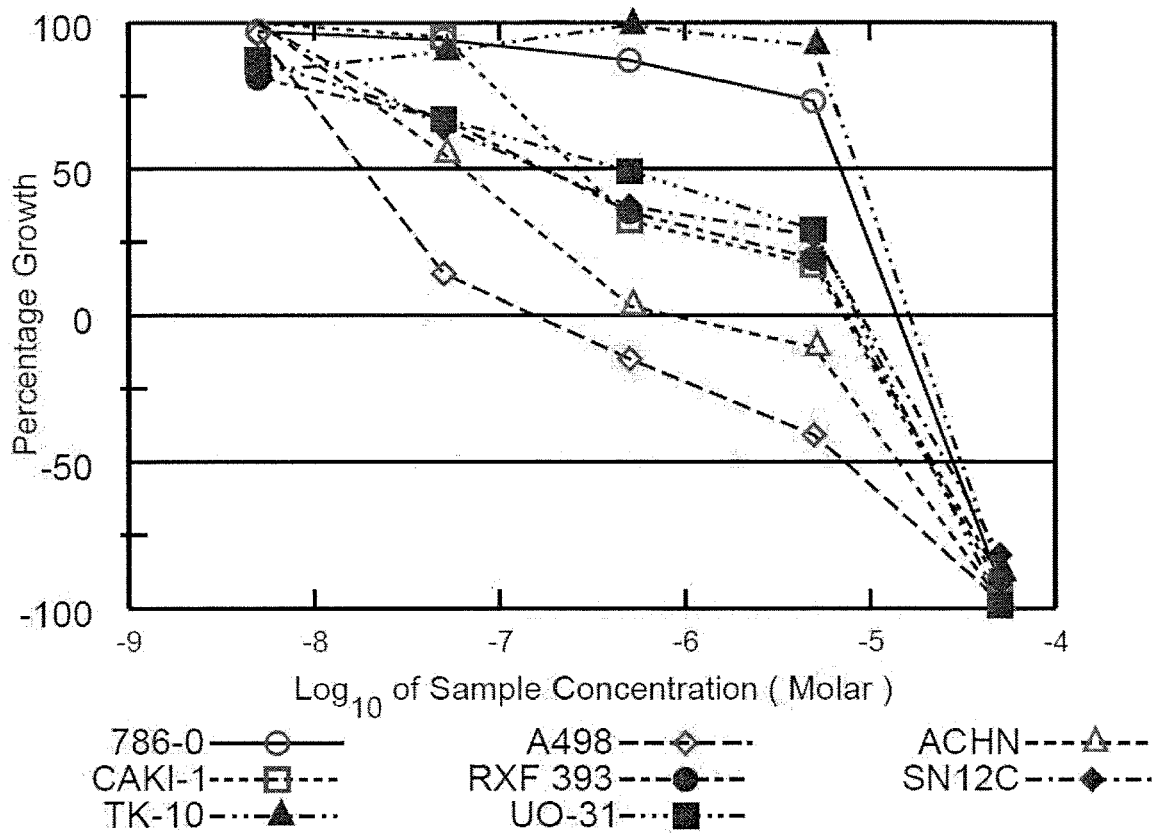
Figure 11H:
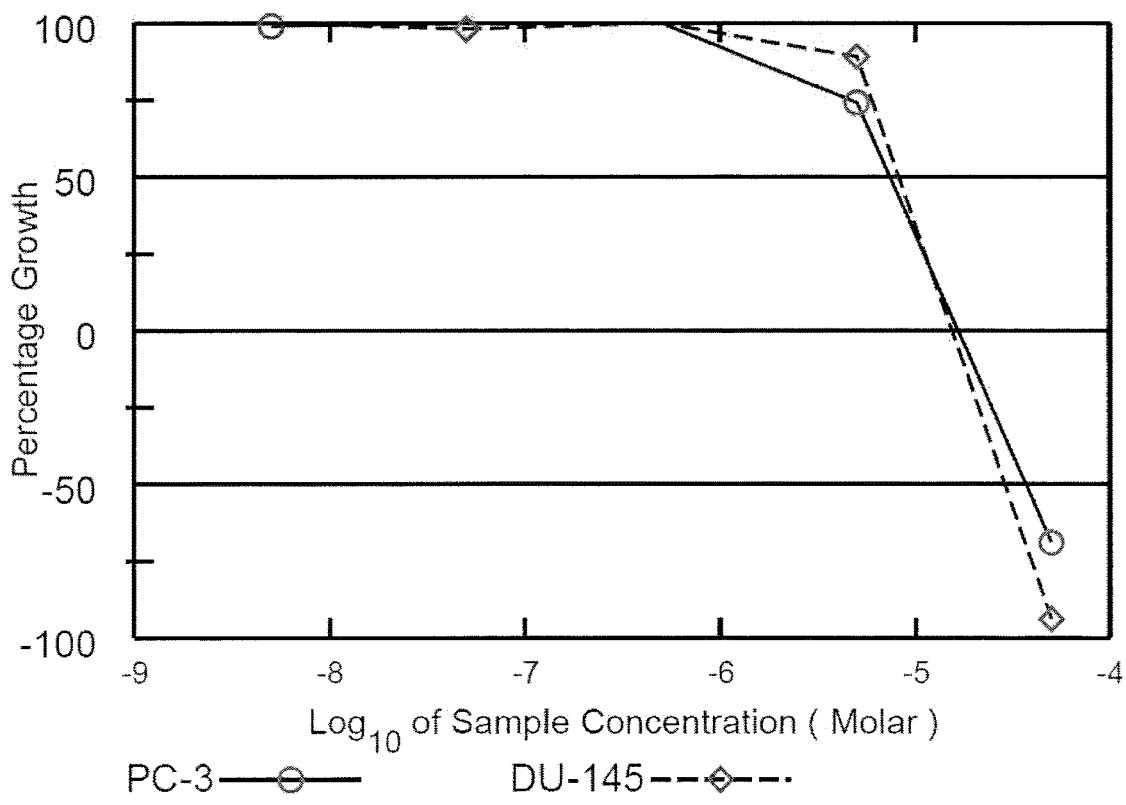
Figure 11I:
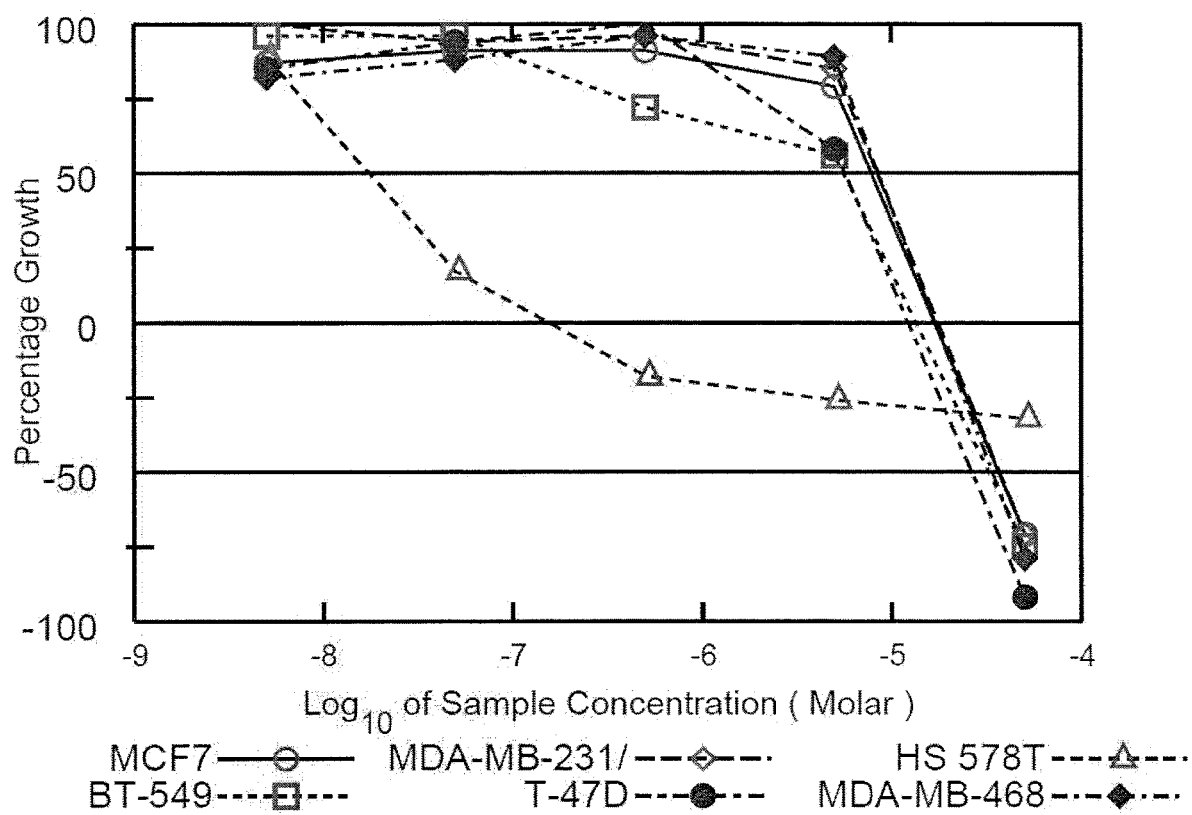

Steps a) through g), as shown in FIG. 2, are set forth in detail below.

Step a)

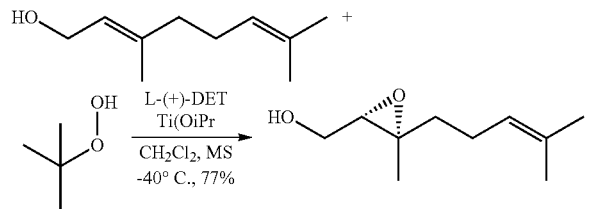

Dry CH$_2$Cl$_2$ was added to a flame-dried three-necked 1 L flask containing activated 4 Å molecular sieves (powder) and provided with an Argon inlet, an addition funnel and a thermometer. After cooling to −20° C., previously distilled L-(+)-diethyl tartrate was added dropwise through the addition funnel. Then, the addition funnel was rinsed with dry CH$_2$Cl$_2$ before being charged with previously distilled titanium (IV) isopropoxide. After its dropwise addition, the same operation was repeated with tert-butyl hydroperoxide (solution 5.5 M in decane). The mixture is stirred at this temperature for 20 min before being cooled to −40° C., then a solution of previously distilled geraniol in CH$_2$Cl$_2$ was slowly added by an addition funnel, and the final mixture was left reacting for 4 h or until TLC analysis shows no starting material left. Water was slowly added, and the reaction was left to reach room temperature. Then an aqueous solution containing NaOH (30%) and NaCl (5%) was added, the mixture was left stirring for 1 h before being filtered by a three layers bed of silica+CELITE™+silica eluting with extra CH$_2$Cl$_2$. The filtrated was transferred to a separation funnel and the layers separated. The aqueous layer was further extracted with CH$_2$Cl$_2$ (×3) and the combined organic layers washed with water and brine, then dried over anhydrous Na$_2$SO$_4$, filtered and concentrated under reduced pressure. The crude was purified through vacuum distillation (1.7 mbar, 80-82° C.) affording the pure product.

The enantiomeric ratio was determined by protection of the alcohol moiety with a tosyl group (following the procedure described by Nakatsuji et al. (*Org. Lett.* 2008, 10, 2131-2134) spectroscopic data of the product was in accordance with previously reported in Riou et al. (*J. Org. Chem.* 2008, 73, 7436-7439), its analysis by chiral HPLC showed an enantiomeric ratio of 9:1 (Agilent HPLC 1100, ChiralPack IA, room temperature 11.91 min (major), 14.57 min (minor) (Agilent Technologies, Santa Clara, Calif.)).

Step b)

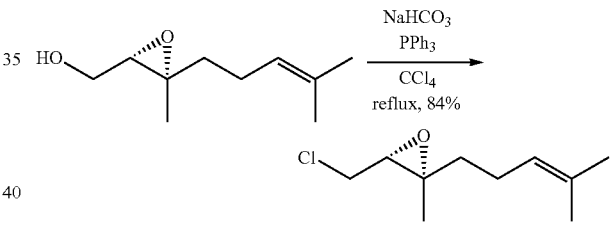

CCl$_4$ was added into a 3-necked 1 L flask connected to a refrigerant, an Argon inlet and a thermometer, containing ((2S, 3S)-3-methyl-3-(4-methylpen-3-en-1 yl)oxiran-2-yl) methanol. Triphenylphosphine and sodium hydrogen carbonate were added portionwise and the mixture was heated to reflux (82° C. internal temperature) over 5 h or until TLC analysis shows no starting material left. Cyclohexane was added, and the crude was filtered through a pad of CELITE™. Then the solvent was evaporated under reduced pressure and washed again with cyclohexane and filtered through CELITE™. After solvent evaporation, the pure product was afforded by vacuum distillation (0.9 mbar, 74-76° C.).

Step c)

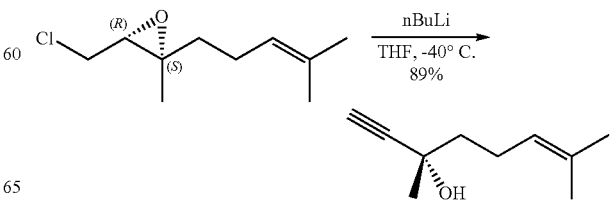

(2S,3R)-3-(chloromethyl)-2-methyl-2-(4-methylpent-3-en-1 yl)oxirane was dissolved in dry THF, and the solution was transferred to a 3-necked 1 L flask connected to an addition funnel. The flask was refrigerated to −40 OC and then nBuLi (1.3 M solution in hexanes) were added dropwise through the addition funnel. After the addition (ca. 1 h) the mixture was left stirring for 30 min. The reaction was quenched by careful addition of aqueous saturated NH$_4$Cl solution at −40° C. Then the mixture was allowed to reach room temperature and the layers were separated, the aqueous layer was further extracted with Et$_2$O (twice) and the combined organic layers washed with saturated NH$_4$Cl solution and brine, dried over anhydrous Na$_2$SO$_4$, filtered and concentrated under vacuum. The resulting crude was distilled under reduced pressure (72° C., 1.8 mbar).

Step d)

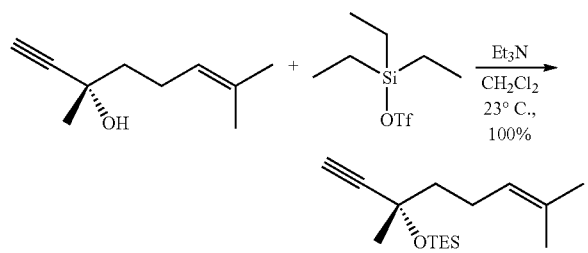

(S)-3,7-dimethyloct-6-en-1-yn-3-ol was dissolved in dry CH$_2$Cl$_2$, Et$_3$N was added and the solution was cooled to 0° C. in an ice bath. Then TESOTf was added dropwise through an addition funnel. After the addition, the reaction was left to reach room temperature (22° C.) and left stirring for 12 h. Aqueous saturated NH$_4$Cl solution (100 mL) was added and the layers separated. The aqueous layer was further extracted twice with CH$_2$Cl$_2$, the combined organic layers washed with brine, dried over Na$_2$SO$_4$, and concentrated in vacuo. The crude product was purified by filtration through a silica column eluting with cyclohexane.

Step e)

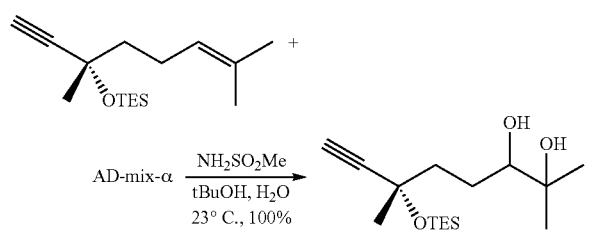

A solution of (S)-(3-7-dimethyloct-6-en-1-yn-3-yloxy)triethylsilane in tert-butanol was added at 0° C. to a stirring solution of AD-mix-α and methanesulfonamide in a mixture of tert-butanol and water. After the addition, the reaction was left stirring at room temperature (about 23° C.) for 12 h. Na$_2$SO$_3$ was added at 0° C., the mixture was left stirring for 3 additional hours, and then the two layers were separated. The aqueous layer was further extracted with EtOAc (×3) and the combined organic layers washed twice with KOH (2 M) solution and dried over anhydrous Na$_2$SO$_4$. After solvent evaporation, a crude product was obtained that can be used without further purification.

Steps f) and g)

Steps f) and g) for the synthesis of products 3a and 5a were described in Molawi et al. (*Angew. Chem. Int. Ed.* 2010, 122, 3595-3597).

Step h)

General procedure A (aldol reaction): a solution of diisopropylamine in THF was cooled to 0° C. in a water-ice bath. Then a solution of nBuLi in hexanes was added through a syringe pump over 30 minutes. The mixture was stirred in the water-ice bath for 30 extra min and then cooled to −78° C. At this temperature a solution of the methylketone of formula R$_1$COMe (1.5 equiv) in THF (0.25 M) was added dropwise over 30 min (syringe pump, internal temperature kept under −70° C. at all times). The solution was stirred at −78° C. for 2 h before a solution of (S,E)-2,6-dimethyl-6-(triethylsilyloxy)oct-2-en-7-ynal in THF (0.1 M) was added dropwise over 10 min. The resulting mixture was stirred 15 h at −78° C. and then quenched at the same temperature with saturated aqueous NH$_4$Cl solution, added slowly over 30 min, keeping temperature under −30° C. After complete addition, the mixture was allowed to reach room temperature. EtOAc was added, and the layers were separated. The aqueous layer was extracted twice with EtOAc, and the combined organic layers were dried over Na$_2$SO$_4$, filtered, and concentrated under vacuum. The crude oil obtained was purified by silica flash chromatography.

Step i)

The product prepared in step h) can be cyclized with a catalyst, such as a Au(I) catalyst. For example, [IPrAuN-CPh][SbF6] (Amijs et al., *J. Org. Chem.* 2008, 73, 7721-7730) was added at room temperature to a solution of the enynone in dry CH$_2$Cl$_2$ (0.1 M) (Molawi et al., *Angew. Chem. Int. Ed.* 2010, 122, 3595-3597) containing 3 Å molecular sieves under argon atmosphere. The reaction was stirred under completion (3-8 h) and then quenched with Et$_3$N. After solvent evaporation under vacuum, the crude was purified by silica chromatography (mixtures cyclohexane:EtOAc, 9:1 to 1:1) to obtain the pure tricycle compound as a single diastereoisomer.

Step j)

The product prepared in step i) was deprotected. For example, the 1-triethylsilyloxy tricyclic compound was dissolved in dry THF (0.1 M) under argon atmosphere, and the solution was cooled to 0° C. in an ice bath, then TBAF solution was added dropwise (1 M in THF). After the addition, the reaction was left stirring at room temperature (about 23° C.) for 12 h before being quenched with a saturated NH$_4$Cl solution. EtOAc was added and the layers separated, then the aqueous layer was further extracted with EtOAc twice. The combined organic layers were dried with anhydrous Na$_2$SO$_4$, filtered, and concentrated under vacuum. The crude was purified by silica flash chromatography using a mixture of cyclohexane:EtOAc 1:1 as eluent.

Step k)

Next, the product prepared in step j) was deprotected. For example, the product of step j) was dissolved in dry CH$_2$Cl$_2$ (0.05 M), N,N-dimethylpyridin-4-amine, and 1H-imidazole were added followed by tert-butylchlorodimethylsilane. The mixture was left stirring at 23° C. under N$_2$ atmosphere between 6 and 10 h until full conversion was observed by TLC. Then, the reaction was stopped by addition of HCl (1 M) solution followed by extractive work up with CH$_2$Cl$_2$. The combined organic layers were dried with anhydrous Na$_2$SO$_4$ and concentrated in vacuo. Purification of the crude by silica gel chromatography affords the pure product.

Step l)

The product of step k) was then catalytically oxidized. For example, chromium (VI) oxide was added to a solution of pyridine in dry CH$_2$Cl$_2$ (0.05 M) at 0° C. and then warmed to room temperature. Then a solution of the alcohol prepared in step k) compound in CH$_2$Cl$_2$ was added at once and the reaction was left stirring for 1 h at room temperature (about 23° C.). After this time, the crude was diluted with Et$_2$O and filtered through a pad of silica and evaporated to dryness. The crude was purified through a silica column, eluting with cyclohexane:EtOAc from 98:2 to 95:5. Two fractions were obtained corresponding to the ketone and the desired epoxy-alcohol. The ketone was dissolved in MeOH (0.1 M), CeCl$_3$.(H$_2$O)$_7$ was added followed by NaBH$_4$. The reaction was vigorously stirred for 5 min before being quenched with water. After extractive work up with EtOAc and purification by flash chromatography on silica (cyclohexane:EtOAc, 95:5) the desired epoxyalcohol was obtained and combined with the previous obtained fraction.

Step m)

Next, the epoxide formed in step 1) was deoxygenated. In particular, nBuLi (1.2 M in hexanes) was added dropwise to a solution of WCl$_6$ (2 equiv) in dry THF at −78° C. The solution was left to slowly reach room temperature for 1 h, then left 10 extra min stirring at room temperature before being cooled down again at 0° C. A solution of the epoxy-alcohol in THF (0.1 M final concentration) was then slowly added, and the reaction was allowed to reach room temperature (about 23° C.) and then heated at 50° C. between 2-4 h until full conversion was achieved. The reaction was poured into a Rochelle salt:NaOH solution (1.5 M:2 M, 200 mL×mmol of substrate) and vigorously stirred for 10 min. Then Et$_2$O was added and the layers separated. The aqueous layer was further extracted with Et$_2$O twice, the combined organic layers washed with brine solution, dried over Na$_2$SO$_4$, filtered and concentrated under vacuum. The crude was purified by silica chromatography to provide the pure product.

Step n)

The product of step m) next undergoes ester formation and deprotection. In particular, a solution of the free alcohol, the compound of formula R$_5$COCl, DMAP, and NEt$_3$ in dry CH$_2$Cl$_2$ (0.2 M) was stirred at reflux at 80° C. in a capped pressure tube for 4 h. After cooling to room temperature, the crude product was filtered through a pad of silica eluting with cyclohexane:EtOAc 9:1. After concentration, the obtained material was used directly in the deprotection of the tert-butyldimethylsilyl group. A TBAF solution (1.0 M in THF) was added to a solution of the TBS-protected analogue in THF (0.1 M) at 0° C. Then, the reaction was allowed to stir at 23° C. for 10 h before being quenched with water. EtOAc was added to the mixture and the two layers separated, the aqueous layer was further extracted twice with EtOAc and then the combined organic layers were dried over Na$_2$SO$_4$, filtered and concentrated under vacuum. The crude was purified by silica chromatography.

Step o)

Next, the product of step n) undergoes a Yamaguchi esterification. For example, Et$_3$N and 2,4,6-trichlorobenzoyl chloride were added to a stirred solution containing the tricyclic alcohol free product, an acid of formula R$_5$CO$_2$H and DMAP in toluene (0.03 M) at 0° C. The resulting white suspension was stirred at room temperature (about 23° C.) for 1 h before being quenched by adding a saturated aqueous NH$_4$Cl solution. Et$_2$O was added and the layers separated. The aqueous layer was further extracted twice with Et$_2$O. The combined organic layers were washed with brine, dried over Na$_2$SO$_4$, filtered, and concentrated in vacuo. The crude was purified by flash chromatography on silica.

If the acid contained a protecting group (e.g., TBDPS-protected glycolic acid, TBDPS-protected lactic acid) the final product was obtained by deprotection of the crude with acid. For example, acetic acid and a TBAF solution (1 M in THF) were added to a stirred solution of the TBDPS-protected analogue in THF (0.1 M) at 0° C. After stirring for 4 h at room temperature (about 23° C.), the reaction was quenched with a saturated aqueous NH$_4$Cl solution, followed by an extractive work up with EtOAc. The combined organic layers were dried over Na$_2$SO$_4$, filtered, and concentrated under vacuum. The final compounds were obtained after chromatographic purification on silica.

Example 3

This example illustrates that compounds of the invention inhibit human cancer cell growth.

Samples containing exemplary compounds of formulas (Ia)-(Ig) were tested in the standard National Cancer Institute 60-cell line protocol. First, they were tested against all 60 cell lines in a single final concentration of 10 micromolar. Then, they were separately tested in five 10-fold dilutions. The drug exposure was two days, with an SRB endpoint. The results are set forth in Table 1.

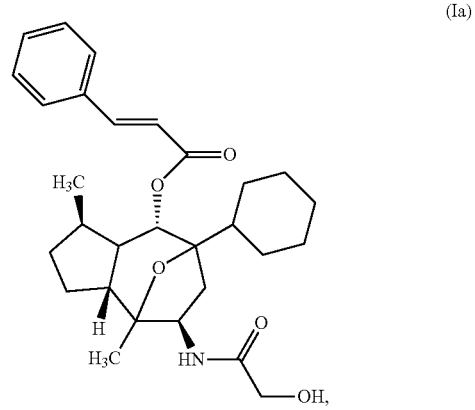

(Ia)

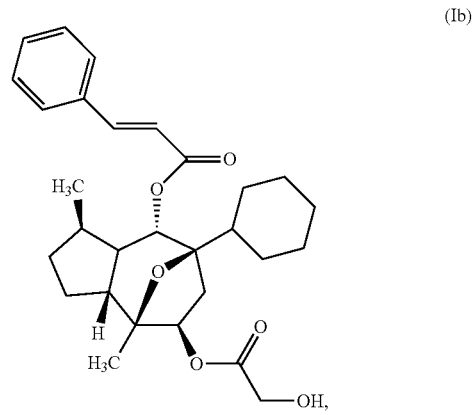

(Ib)

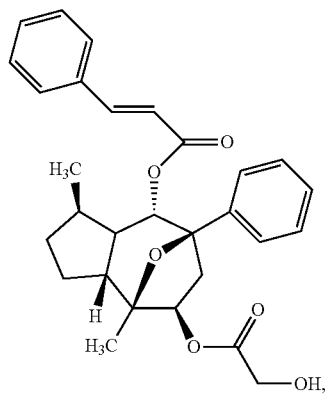
(Ic)
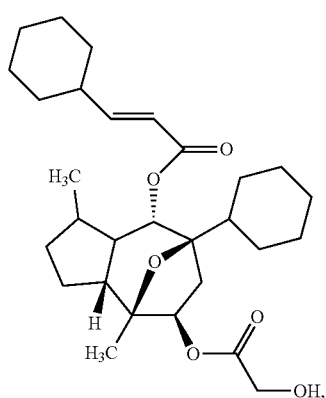
(Id)
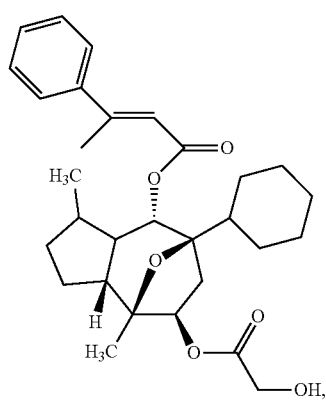
(Ie)
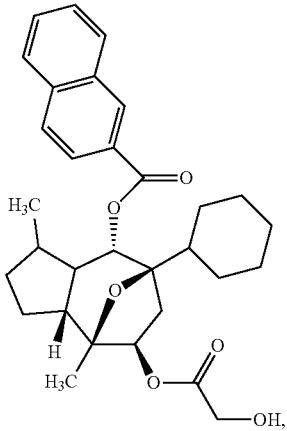
(If)
and
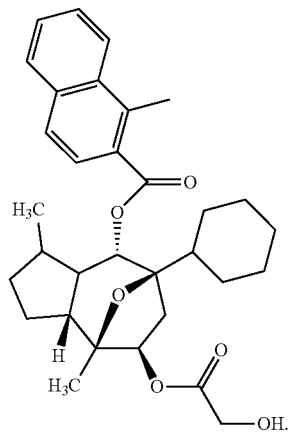
(Ig)
TABLE 1
Potency of several compounds of formula (I) in cancer cell lines within the NCI 60 cell assay (GI$_{50}$ values μM).
| Cell Line | (Ia) GI-50 value μM | (Ib) GI-50 value μM | (Ic) GI-50 value μM | (Id) GI-50 value μM | (Ie) GI-50 value μM | (If) GI-50 value μM | (Ig) GI-50 value μM | Englerin A GI-50 value μM |
|---|---|---|---|---|---|---|---|---|
| OVARIAN | | | | | | | | |
| OVCAR-8 | 16.218 | 0.513 | 6.761 | 10.715 | 4.266 | 5.623 | 6.607 | 0.032 |
| RENAL | | | | | | | | |
| 786-0 | 14.791 | 1.175 | 11.749 | 12.023 | 5.129 | 5.370 | 6.457 | 1.072 |
| A498 | 2.188 | 0.019 | 0.191 | 0.021 | 0.016 | 0.019 | 0.017 | 0.010 |
| ACHN | 3.467 | 0.010 | 0.178 | 0.022 | 0.015 | 0.019 | 0.059 | 0.017 |

TABLE 1-continued

Potency of several compounds of formula (I) in cancer cell lines within the NCI 60 cell assay ($GI_{50}$ values μM).

| Cell Line | Compound | | | | | | | |
|---|---|---|---|---|---|---|---|---|
| | (Ia) GI-50 value μM | (Ib) GI-50 value μM | (Ic) GI-50 value μM | (Id) GI-50 value μM | (Ie) GI-50 value μM | (If) GI-50 value μM | (Ig) GI-50 value μM | Englerin A GI-50 value μM |
| RXF 393 | 3.311 | 0.078 | 0.251 | 0.034 | 0.079 | 0.071 | 0.166 | 0.059 |
| SN12C | 11.482 | 0.085 | 0.537 | 0.032 | 0.023 | 0.052 | 0.158 | 1.047 |
| UO-31 | 4.786 | 0.015 | 0.155 | 0.029 | 0.062 | 0.040 | 0.407 | 0.015 |
| BREAST | | | | | | | | |
| HS 578T | 2.818 | 0.024 | 0.112 | 0.016 | 0.010 | 0.023 | 0.017 | 0.010 |
| BT-549 | 13.183 | 0.034 | 0.407 | 0.055 | 0.120 | 0.071 | 5.248 | 0.107 |
| Average GI-50 | 8.027 | 0.217 | 2.260 | 2.550 | 1.080 | 1.254 | 2.126 | 0.263 |

Example 4

This example illustrates some of the properties of the compounds of formula (I) in accordance with an embodiment of the invention.

FIG. 5-11 depict the dose response curves for certain compounds of formula (I) (i.e., compounds (Ia)-(Ig)) against various cancer cell lines in a 60-cell test, showing that compounds of formula (I) are active against a number of leukemia, non-small cell, colon cancer, CNS cancer, melanoma, ovarian, renal, prostate, and breast, cell lines.

FIG. 5A-5I are the dose response curves for (Ia).
FIG. 6A-6I are the dose response curves for (Ib).
FIG. 7A-7I are the dose response curves for (Ic).
FIG. 8A-8I are the dose response curves for (Id).
FIG. 9A-9I are the dose response curves for (Ie).
FIG. 10A-10I are the dose response curves for (If).
FIG. 11A-11I are the dose response curves for (Ig).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I)

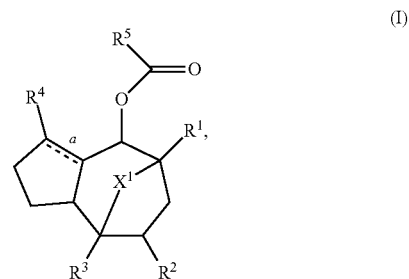

wherein
"a" represents a single bond or double bond;
$R^1$ is $C_3$-$C_6$ cycloalkyl, heterocycloalkyl, aryl, or heteroaryl, each of the foregoing is optionally substituted;
$R^2$ is selected from hydroxy, —$X^2$—(C=$^3$)—($CR^6R^7)_m$—$X^2$—(C=$X^3$)—$R^8$, —$X^2$—(C=$X^3$)—($CR^6R^7)_m$—$R^8$, and —$X^2$—(C=$X^3$)—($CR^6R^7)_m$—$X^2$—$R^{18}$;
$R^6$ and $R^7$ are independently selected from hydrogen, hydroxy, fluorine, chlorine, and $C_1$-$C_6$ alkyl;
$R^8$ is selected from optionally substituted $C_1$-$C_6$ alkyl, optionally substituted fluoro $C_1$-$C_6$ alkyl, optionally substituted heterocycloalkyl, optionally substituted aryl, optionally substituted heteroaryl, optionally substituted alkoxy, optionally substituted aryloxy, hydroxy, and —NR$^{15}$R$^{16}$;

R$^{15}$ is selected from hydrogen and C$_1$-C$_6$ alkyl;

R$^{16}$ is selected from hydrogen, C$_1$-C$_6$ alkyl, and COOR$^{17}$;

R$^{17}$ is C$_1$-C$_6$ alkyl;

R$^{18}$ is selected from C$_1$-C$_6$ alkyl, fluoro C$_1$-C$_6$ alkyl, aryl, and heteroaryl, each of which is optionally substituted;

each X$^2$ is independently selected from O, S and NR$^{15}$;

each X$^3$ is independently selected from O and S;

R$^3$ and R$^4$ are independently a C$_1$-C$_6$ alkyl;

R$^5$ is selected from —(CR$^9$R$^{10}$)$_n$—R$^{11}$ and —(CR$^{12}$=CR$^{13}$)$_n$—R$^{14}$;

R$^9$ and R$^{10}$ are independently selected from hydrogen and C$_1$-C$_6$ alkyl; or alternatively R$^9$ and R$^{10}$, together with the carbon to which they are attached, form a C$_3$-C$_6$ cycloalkyl;

R$^{11}$ and R$^{14}$ are independently selected from C$_1$-C$_6$ alkyl, C$_3$-C$_6$ cycloalkyl, aryl, and heteroaryl, each of which is optionally substituted;

R$^{12}$ and R$^{13}$ are independently selected from hydrogen, halogen, and C$_1$-C$_6$ alkyl;

X$^1$ is selected from O, NR$^{15}$, and S; and n and m are independently selected from 0 and an integer of 1-3, provided that when "a" is a double bond, R$^1$ is heterocycloalkyl, which is optionally substituted;

or a pharmaceutically acceptable salt thereof.

2. The compound of claim 1, wherein X$^1$ is O, or a pharmaceutically acceptable salt thereof.

3. The compound of claim 1, wherein R$^2$ is —OC(O)CH$_2$OH or —NHC(O)CH$_2$OH, or a pharmaceutically acceptable salt thereof.

4. The compound of claim 1, wherein R$^3$ is methyl, or a pharmaceutically acceptable salt thereof.

5. The compound of claim 1, wherein R$^4$ is methyl, or a pharmaceutically acceptable salt thereof.

6. The compound of claim 1, wherein R$^5$ is —(CR$^{12}$=CR$^{13}$)$_n$—R$^{14}$, R$^{12}$ and R$^{13}$ are each hydrogen or C$_1$-C$_6$ alkyl, R$^{14}$ is C$_3$-C$_6$ cycloalkyl or phenyl, and n is 1-3, or a pharmaceutically acceptable salt thereof.

7. The compound of claim 1, wherein "a" is a double bond and R$^1$ is heterocycloalkyl, which is optionally substituted, or a pharmaceutically acceptable salt thereof.

8. The compound of claim 7, wherein the heterocycloalkyl is aziridinyl, oxiranyl, thiazolinyl, imidazolidinyl, piperazinyl, homopiperazinyl, pyrrolinyl, pyrrolidinyl, tetrahydrofuranyl, tetrahydrothiofuranyl, pyranyl, tetrahydropyranyl, piperidinyl, morpholinyl, or thiomorpholinyl, each of the foregoing is optionally substituted, or a pharmaceutically acceptable salt thereof.

9. The compound of claim 8, wherein the heterocycloalkyl is piperidinyl of the formula

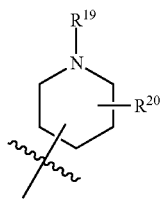

wherein

R$^{19}$ is hydrogen, C$_1$-C$_6$ alkyl or C$_1$-C$_6$ alkylcarbonyl, each of which, other than hydrogen, is optionally substituted; and R$^{20}$ is hydrogen, halo, C$_1$-C$_6$ alkyl, C$_2$-C$_6$ alkenyl, C$_2$-C$_6$ alkynyl, hydroxy, nitro, cyano, amino, C$_1$-C$_6$ alkylamino, C$_1$-C$_6$ alkoxy, aryloxy, C$_1$-C$_6$ aralkoxy, carboxyl, carboxy-C$_1$-C$_6$ alkyl, carboxy-C$_1$-C$_6$ alkyloxy, amido, C$_1$-C$_6$ alkylamido, halo-C$_1$-C$_6$ alkylamido, aryl, heteroaryl, or heterocycloalkyl, or a pharmaceutically acceptable salt thereof.

10. The compound of claim 9 that is selected from the group consisting of

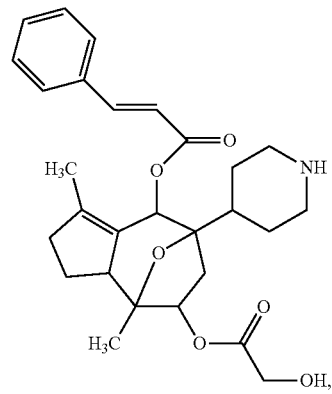

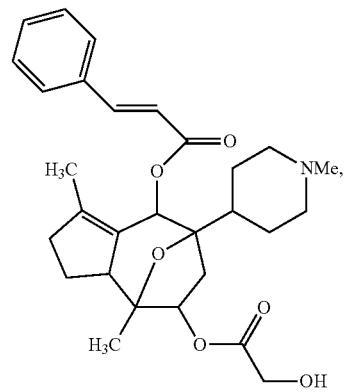

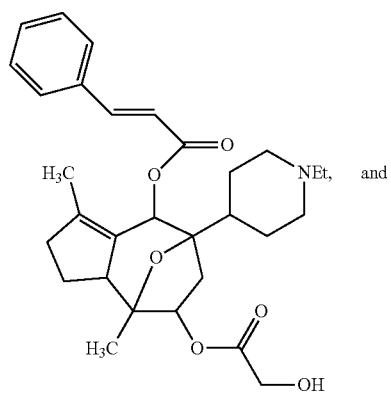

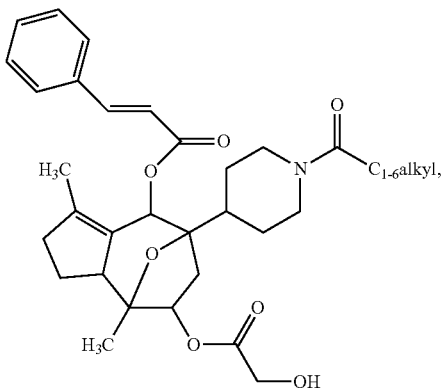
or a pharmaceutically acceptable salt thereof.
11. The compound of claim 1, wherein "a" is a single bond, or a pharmaceutically acceptable salt thereof.
12. The compound of claim 11, wherein $R^1$ is $C_3$-$C_6$ cycloalkyl or phenyl, or a pharmaceutically acceptable salt thereof.
13. The compound of claim 1 that is selected from the group consisting of
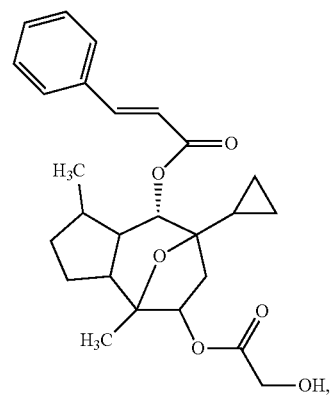
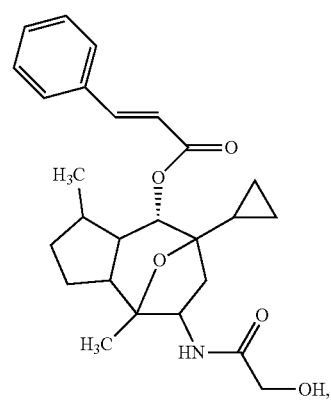
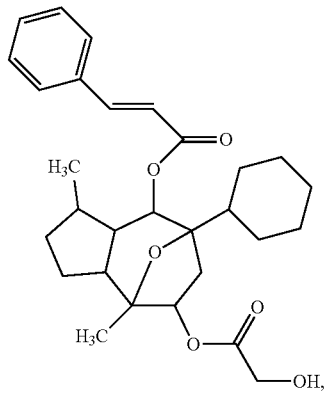
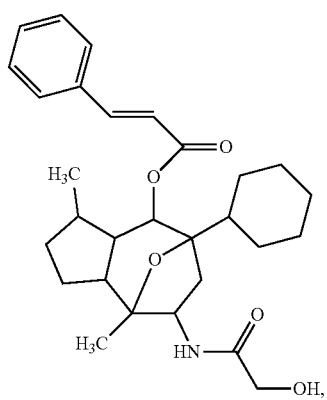
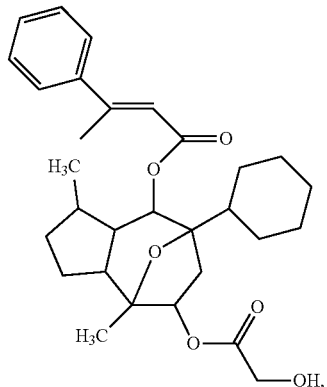
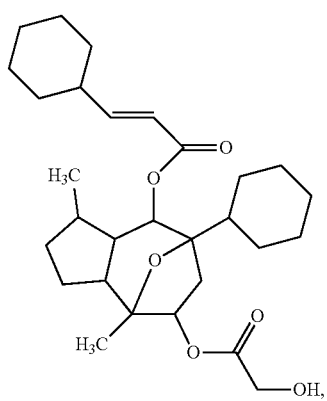

-continued

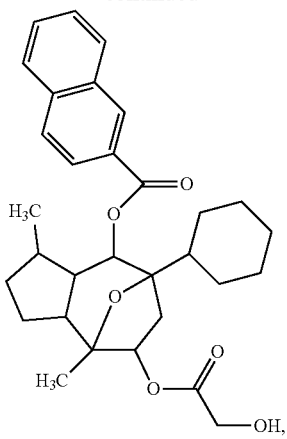

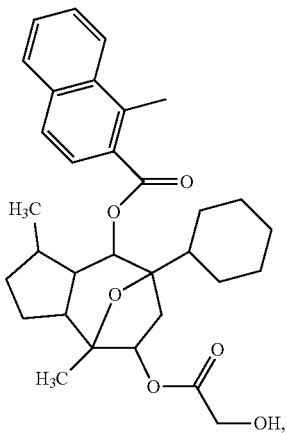

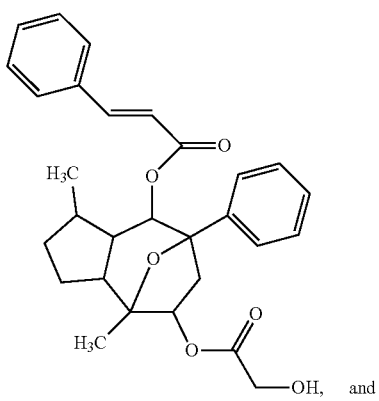

-continued

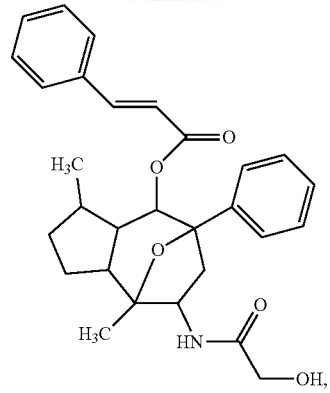

or a pharmaceutically acceptable salt thereof.

14. A pharmaceutical composition comprising a pharmaceutically acceptable carrier and the compound or a pharmaceutically acceptable salt thereof of claim 1.

15. The compound of claim 1 or a pharmaceutically acceptable salt thereof, wherein
   $R^1$ is optionally substituted $C_3$-$C_6$ cycloalkyl, optionally substituted aryl, optionally substituted heteroaryl, or piperidinyl;
   $R^2$ is selected from hydroxy, $-X^2-(C=X^3)-(CR^6RH^7)_m-X^2-(C=X^3)-R^8$, and $-X^2-(C=X^3)-(CR^6R^7)_m-R^8$;
   $R^8$ is selected from hydroxy and $-NH_2$; and
   $X^1$ is O;
   provided that when "a" is a double bond, $R^1$ is piperidinyl.

16. A method of treating cancer in a subject comprising administering to the subject a therapeutically effective amount of a compound or a pharmaceutically acceptable salt of claim 15, wherein the cancer is leukemia, non-small cell lung cancer, colon cancer, melanoma, prostate cancer, renal cancer, bladder cancer, breast cancer, central nervous system (CNS) cancer, ovarian cancer, or Ewing's sarcoma.

17. The method according to claim 16, wherein the cancer is renal cancer.

18. The method according to claim 16, wherein the cancer is prostate cancer.

19. The method according to claim 16, wherein the cancer is Ewing's sarcoma.

20. The method according to claim 16, wherein the cancer is bladder cancer or breast cancer.

21. A pharmaceutical composition comprising a pharmaceutically acceptable carrier and the compound or a pharmaceutically acceptable salt thereof of claim 15.

\* \* \* \* \*